US008821887B2

(12) United States Patent
Larche et al.

(10) Patent No.: US 8,821,887 B2

(45) **Date of Patent: *Sep. 2, 2014**

(54) T-CELL ANTIGEN PEPTIDE FROM ALLERGEN FOR STIMULATION OF IL-10 PRODUCTION

(75) Inventors: Mark Larche, Ontario (CA); Roderick Peter Hafner, Oxford (GB); Paul Laidler, Oxford (GB)

(73) Assignee: Circassia Limited, Oxford (GB)

( * ) Notice: Subject to any disclaimer, the term of this patent is extended or adjusted under 35 U.S.C. 154(b) by 298 days.

This patent is subject to a terminal disclaimer.

(21) Appl. No.: 13/057,377

(22) PCT Filed: Aug. 14, 2009

(86) PCT No.: PCT/GB2009/001995

§ 371 (c)(1), (2), (4) Date: May 6, 2011

(87) PCT Pub. No.: WO2010/018384

PCT Pub. Date: Feb. 18, 2010

(65) Prior Publication Data

US 2011/0206709 A1 Aug. 25, 2011

(30) Foreign Application Priority Data

| | | |
|---|---|---|
| Aug. 15, 2008 | (GB) | 0814986.6 |
| Aug. 15, 2008 | (GB) | PCT/GB08/002778 |
| Aug. 15, 2008 | (GB) | PCT/GB08/002779 |
| Aug. 15, 2008 | (GB) | PCT/GB08/002780 |
| Aug. 15, 2008 | (GB) | PCT/GB08/002781 |
| Aug. 20, 2008 | (GB) | 0815218.3 |
| Feb. 5, 2009 | (GB) | 0901927.4 |
| May 1, 2009 | (EP) | 09251252 |
| Jul. 20, 2009 | (GB) | 0912578.2 |

(51) Int. Cl.

| | |
|---|---|
| ***A61K 39/00*** | (2006.01) |
| ***A61K 39/35*** | (2006.01) |
| ***A61K 39/36*** | (2006.01) |
| ***A61K 38/00*** | (2006.01) |

(52) U.S. Cl.

USPC .................... 424/185.1; 424/275.1; 514/1.1

(58) Field of Classification Search

None

See application file for complete search history.

(56) References Cited

U.S. PATENT DOCUMENTS

| | | | |
|---|---|---|---|
| 5,736,507 A | 4/1998 | Boots et al. | |
| 5,820,862 A | 10/1998 | Garman et al. | |
| 6,335,019 B1 | 1/2002 | Rogers et al. | |
| 6,441,157 B1 | 8/2002 | Singh et al. | |
| 7,112,333 B1 | 9/2006 | Griffith et al. | |
| 2002/0146759 A1 | 10/2002 | Albani et al. | |
| 2004/0265342 A1 | 12/2004 | Larche et al. | |
| 2006/0008873 A1* | 1/2006 | Thomas et al. | 435/69.1 |
| 2006/0024334 A1 | 2/2006 | Larche et al. | |
| 2007/0092532 A1 | 4/2007 | Root-Bernstein | |

FOREIGN PATENT DOCUMENTS

| | | | |
|---|---|---|---|
| EP | 1958645 | A1 | 8/2008 |
| EP | 2042193 | A1 | 4/2009 |
| WO | 90/11293 | A1 | 10/1990 |
| WO | 93/08279 | A1 | 4/1993 |
| WO | 93/21321 | A2 | 10/1993 |
| WO | 94/01560 | A1 | 1/1994 |
| WO | 94/24281 | A1 | 10/1994 |
| WO | 95/28424 | A1 | 10/1995 |
| WO | 96/13589 | A1 | 5/1996 |
| WO | 99/34826 | A1 | 7/1999 |
| WO | 02/081512 | A1 | 10/2002 |
| WO | 03/082924 | A1 | 10/2003 |
| WO | 03/088997 | A2 | 10/2003 |
| WO | 03/094957 | A2 | 11/2003 |
| WO | 2004/005334 | A2 | 1/2004 |
| WO | 2004/092210 | A2 | 10/2004 |
| WO | 2006/075253 | A2 | 7/2006 |
| WO | 2006/132607 | A1 | 12/2006 |
| WO | 2007/063075 | A | 6/2007 |
| WO | 2008/098749 | A2 | 8/2008 |
| WO | 2008/139163 | A1 | 11/2008 |
| WO | 2008/145998 | A1 | 12/2008 |
| WO | 2009/022154 | A2 | 2/2009 |
| WO | 2009/022156 | A2 | 2/2009 |
| WO | 2009/022157 | A2 | 2/2009 |
| WO | 2010/018378 | A2 | 2/2010 |

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*

(Continued)

*Primary Examiner* — Nora Rooney

(74) *Attorney, Agent, or Firm* — Nelson Mullins Riley & Scarborough LLP; Jane E. Remillard, Esq.; Jeanne M. DiGiorgio

(57) ABSTRACT

A first or second polypeptide for use in a method of treating or preventing a disorder by tolerization, wherein said method comprises administration of the first and second polypeptide; and wherein both first and second polypeptides:

i) are of 7 to 30 amino acids in length;

ii) comprise at least one MHC Class II-binding T cell epitope; and iii) are a fragment of a protein allergen or a homologous variant of said fragment;

wherein said first polypeptide induces the release of an amount of IL-10 that is greater than the amount of IL-10 released in response to the whole protein allergen from which the first polypeptide derives;

wherein said disorder is characterized by an inappropriate immune response to the protein allergen from which the second polypeptide derives.

5 Claims, 6 Drawing Sheets

(56) References Cited

OTHER PUBLICATIONS

Burgess et al. 'Possible Dissociation of the Heparin-binding and Mitogenis Activities of Heparin-binding (Acidis Fibroblast) Growth Factor-1 from Its Receptor-binding Activites by Site-directed Mutagenesis of a Single Lysine Residue.' J. Cell. Biol. 111:2129-2138, 1990.*

Lazar et al. 'Transforming Growth Factor alpha:Mutation of Aspartic Acid 47 and Leucine 48 Results in Different Biological Activities.' Mol. Cell. Biol. 8(3):1247-1252, 1988.*

Blumenthal et al. 'Definition of an Allergen.' Allergens and Allergen Immunotherapy. Ed. R Lockey, S. Bukantz and J. Bousquet. New York: Marcel Decker, 2004.37-50.*

Skolnick et al. 'From genes to protein structure and function: novel applications of computational approaches in the genomic era.' Trends in Biotech. 18:34-39, 2000.*

Attwood et al. 'The Babel of Bioinformatics.' Science. 290(5491 ):471-473, 2000.*

Kuby et al. 'Immunology.' Fourth Edition, Chapter 18: 449-465, 2001.*

Alexander, Clare et al., "Peptide-based Vaccines in the Treatment of Specific Allergy," Current Drug Targets—Inflammation & Allergy, vol. 1(4):353-361 (2002).

Cardinale, Elizabeth J. et al., "Matrix-assisted Laser Desorption/lonization Time-of-flight (MALDI-TDF) Mass Spectrometry in the Analysis of Allergen Vaccines," J. Allergy Clin. Immunol., vol. 107(2):S19, Abstract No. 65 (2002).

Eusebius, Nirupama P. et al., "Oligoclonal Analysis of the Atopic T Cell Response to the Group 1 Allergen of Cynodon dactylon (Bermuda Grass) Pollen: Pre- and Post-Allergen-Specific Immunotherapy," Int. Arch. Allergy Immunol., vol. 127:234-244 (2002).

Griffith, I.J. et al., "Sequence Polymorphism of Amb A I and Amb A II, the Major Allergens in Ambrosia artemisiifolia (Short Ragweed)," Int. Arch. Allergy Appl. Immunol., vol. 96:296-304 (1991).

Immonen, Anu K. et al., "Use of multiple peptides containing T cell epitopes is a feasible approach for peptide-based immunotherapy in Can f 1 allergy," Immunology, vol. 120(1):38-46 (2006).

Jeannin, Pascale et al., "Immunogenicity and Antigenicity of Synthetic Peptides Derived from the Mite Allergen Der p I," Molecular Immunology, vol. 30(16)1511-1518 (1993).

King, Te Piao et al., "Chemical Modifications of the Major Allergen of Ragweed Pollen, Antigen E," Immunochemistry, vol. 11:83-92 (1974).

Larche, M., "Peptide immunotherapy for allergic diseases," Allergy, vol. 62:325-331 (2007).

Litwin, A. et al., "Regulation of the human immune response to ragweed pollen by immunotherapy. A controlled trial comparing the effect of immunosuppressive peptic fragments of short ragweed with standard treatment," Chemical and Experimental Allergy, vol. 21:457-465 (1991).

Michael, J.G. et al., "Modulation of the immune response to ragweed allergens by peptic fragments," Clinical and Experimental Allergy, vol. 20:669-674 (1990).

Muller, W.-D. et al., "Mapping of T-cell epitopes of Ph1 p 5: evidence for crossreacting and non-crossreacting T-cell epitopes within Ph1 p 5 isoallergens," Clinical and Experimental Allergy, vol. 28:1538-1548 (1998).

Rafnar, Thorunn et al., "Cloning of Amb a I (Antigen E), the Major Allergen Family of Short Ragweed Pollen," The Journal of Biological Chemistry, vol. 266(2):1229-1236 (1991).

Schafer, James Robert A. et al., "Prediction of well-conserved HIV-1 ligands using a matrix-based algorithm, EpiMatrix," Vaccine, vol. 16(19):1880-1884 (1998).

Sone, T. et al., "Identification of human T cell epitopes in Japanese cypress pollen allergen, Cha o 1, elucidates the intrinsic mechanism of cross-allergenicity between Cha o 1 and Cry j 1, the major allergen of Japanese cedar pollen, at the T cell level," Clin. Exp. Allergy, vol. 35:664-671 (2005).

Wraith, David C., "Peptide-based therapy for autoimmune diseases," Drug Discovery Today: Therapeutic Strategies, vol. 3(1):35-40 (2006).

Yang, Ming et al., "Host Genetic and Adjuvant Factors Influence Epitope Specificity to a Major Recombinant Grass Allergen," Int. Arch Allergy Immunol., vol. 111:173-181 (1996).

Zhang, L. et al., "Multiple B- and T-cell epitopes on a major allergen of Kentucky Bluegrass pollen," Immunology, vol. 87:283-290 (1996).

Akdis, Cezmi A. et al., "Role of Interleukin 10 in Specific Immunotherapy," J. Clin. Invest., vol. 102(1):98-106 (1998).

Campbell, John D. et al., "Peptide immunotherapy in allergic asthma generates IL-10-dependent immunological tolerance associated with linked epitope suppression," J. Exp. Med., vol. 206(7):1535-1547 (2009).

Hall, Gillian et al., "Suppression of allergen reactive Th2 mediated responses and pulmonary eosinophilia by intranasal administration of an immunodominant peptide is linked to IL-10 production," Vaccine, vol. 21:549-561 (2003).

Kearley, Jennifer et al., "Resolution of airway inflammation and hyperreactivity after in vivo transfer of CD4+CD25+ regulatory T cells is interleukin 10 dependent," J. Med. Chem., vol. 202(11):1539-1547 (2005).

Larche, Mark et al., "Peptide-based therapeutic vaccines for allergic and autoimmune diseases," Nature Medicine Supplement, vol. 11(4):S69-S76 (2005).

Oldfield, William L.G. et al., "Allergen-Derived T Cell Peptide-Induced Late Asthmatic Reactions Precede the Induction of Antigen-Specific Hyporesponsiveness in Atopic Allergic Asthmatic Subjects," The Journal of Immunology, vol. 167:1734-1739 (2001).

Tarzi, M. et al. "Induction of interleukin-10 and suppressor of cytokine signalling-3 gene expression following peptide immunotherapy," Clin. Exp. Allergy, vol. 36(4):465-474 (2006).

Verhoef, Adrienne et al., "T Cell Epitope Immunotherapy Induces a CD4+ T Cell Population with Regulatory Activity," PLOS Medicine, vol. 2(3):e78 (2005).

U.S. Appl. No. 12/871,575, Robyn O'Hehir, filed Aug. 30, 2010, May 8, 2013.

U.S. Appl. No. 12/673,412, Roderick Peter Hafner, filed Mar. 11, 2010, Jun. 4, 2013.

U.S. Appl. No. 13/057,386, Mark Larche, filed May 27, 2011, Dec. 18, 2012.

U.S. Appl. No. 13/148,024, Roderick Peter Hafner, filed Feb. 21, 2012, Jun. 4, 2013.

U.S. Appl. No. 12/673,386, Roderick Peter Hafner, filed Mar. 11, 2010, Mar. 19, 2013.

Bysice, Andrew, "Possible Intrinsic adjuvanticity of the Amb a 1 (*Ambrosia artemisiifolia*: Ragweed) allergen," McMaster University, Open Access Dissertations and Theses, obtained online at: http://digital.commons.mcmaster.ca/opendissertations, 102 pages, (2012).

* cited by examiner

T-CELL ANTIGEN PEPTIDE FROM ALLERGEN FOR STIMULATION OF IL-10 PRODUCTION

RELATED APPLICATIONS

This application is a 35 U.S.C. 371 national stage filing of International Application No. PCT/GB2009/001995 filed Aug. 14, 2009, which claims priority to GB Application No. 0814986.6 filed Aug. 15, 2008; PCT Application No. PCT/GB08/002,781 filed Aug. 15, 2008; PCT Application No. PCT/GB08/002,780 filed Aug. 15, 2008; PCT Application No. PCT/GB08/002,779 filed Aug. 15, 2008; PCT Application No. PCT/GB08/002,778 filed Aug. 15, 2008; GB Application No. 0815218.3 filed Aug. 20, 2008; GB Application No. 0901927.4 filed Feb. 5, 2009; EP Application No. 09251252.4 filed May 1, 2009; and GB Application No. 0912578.2 filed Jul. 20, 2009. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Nov. 25, 2013, is named JKJ-018US_SL.txt and is 172,792 bytes in size.

FIELD OF THE INVENTION

The present invention relates to peptide compositions for inducing tolerisation to a protein allergen.

BACKGROUND OF THE INVENTION

T-cell antigen recognition is based on the presentation of antigen fragments (peptides) by molecules of the major histocompatibility complex (MHC) on the surface of antigen presenting cells (APCs). MHC: peptide complexes are recognised by antigen-specific T-cell receptors (TCRs) on the T cell surface, and this recognition can initiate a range of immune responses against the antigen.

Allergic diseases are linked to the ability of some antigens, termed allergens, to induce a hypersensitive immune response. There is a need to identify new molecules which are able to modulate immune responses in situations where the response of the immune system is inappropriate. Identification of such molecules would be of benefit in treatment of allergic diseases.

SUMMARY OF THE INVENTION

The present invention relates to a first polypeptide derived from a protein allergen for use in treating or preventing a disorder by tolerisation, wherein the disorder is characterised by an inappropriate immune response to a protein allergen. The tolerising property of the first polypeptide lies in the ability of the polypeptide to cause release of large amounts of the cytokine IL-10.

The present inventors surprisingly identified that peptides derived from allergens may be used to tolerise against other allergen peptides, and thus could be used to prevent or treat allergy. The identified peptides are able to induce a release of IL-10 which exceeds the level released in response to the whole allergen. Given that the short peptides of the invention represent a very short region of the polypeptide chain of the whole allergen, the increased release of IL-10 was unexpected. The peptides of the invention have the ability to induce a greater T cell response through IL-10 production, despite representing a small number of the total number of T cell epitopes present in the whole allergen.

The ability of allergen-derived peptides to release high levels of IL-10 was also surprising. Previous reports of tolerising peptides derived from allergens report release of activatory cytokines such as IL-13 and IFN-gamma. IL-10 is known as an immune modulator which can shift T cell responses away from an allergic-type response. The ability of particular allergen-derived peptides to release a suppressive cytokine in high amounts was unexpected. A significant IL-10 release may lead to induction of regulatory T cells which mediate toleration of the presence of a second protein to which an undesirable immune response is occurring. Following tolerisation, a subsequent encounter with the second protein may not induce any response or may induce a response of lesser degree.

The present inventors have thus identified a class of peptides derived from protein allergens which can act as tolerising agents. The peptides are from 7 to 30 amino acids in length and comprise an MHC Class II-binding T cell epitope derived from the protein allergen. The peptides are fragments of the protein allergen or homologous variants thereof. The length range is selected to allow for a minimal MHC Class II binding epitope whilst avoiding potential crosslinking of IgE receptors on mast cells, thus reducing histamine release. The peptides exhibit IL-10 response characteristics which underlie their tolerising effect. For example, they may be able to induce significant IL-10 release in a large proportion of the population, due to their ability to bind to a variety of MHC alleles. This allows them to serve as general tolerising agents of broad utility in the treatment or prophylaxis of conditions where an undesired immune response is observed. The peptides may also induce a significant release of IL-10 on average in the population as compared to other peptides derived from the same allergen.

Accordingly, the present invention provides:

A first or second polypeptide for use in a method of treating or preventing a disorder by tolerisation, wherein said method comprises administration of the first and second polypeptide; and wherein both first and second polypeptides:

i) are of 7 to 30 amino acids in length;

ii) comprise at least one MHC Class II-binding T cell epitope; and iii) are a fragment of a protein allergen or a homologous variant of said fragment;

wherein said first polypeptide induces the release of an amount of IL-10 that is greater than the amount of IL-10 released in response to the whole protein allergen from which the first polypeptide derives;

wherein said disorder is characterised by an inappropriate immune response to the protein allergen from which the second polypeptide derives. The disorder is typically an allergic disease.

Given that polypeptides having the properties described above have not previously been known for a use according to the invention, the subject matter described herein is unified.

The first polypeptide is typically a fragment of a protein allergen or a variant thereof, preferably a homologous variant. The second polypeptide may be derived from the same protein allergen of which the first polypeptide is a fragment or be derived from a different protein allergen. Where the first and second polypeptides are derived from the same allergen, they represent different fragments of the protein allergen. The first and second polypeptides are thus different and in one embodiment do not have any T cell epitope sequences in common. In one embodiment the first and second polypeptides are not homologous sequences, for example having less than 40% homology with each other.

The first and/or second polypeptides may be derived from a plant allergen, animal dander allergens, a mold or fungal allergen, a dust allergen, an antibiotic or other drug, a stinging insect venom, an environmental allergen or a food allergen and combinations thereof.

The first polypeptide typically:

induces release of IL-10 in at least 35, 40, 45, 50, or 55% of a population of individuals who are allergic to the protein allergen; and/or induces the release of an average amount of IL-10 in the population of (i) that is at least 35, 40, 45, 50 or 55% of the average amount of IL-10 released in response to the whole protein allergen of which the first polypeptide is a fragment.

In one embodiment, the first polypeptide is a fragment of the house dust mite protein Der p 1 or the ragweed protein Amb a 1. More specifically, the first polypeptide may be:

(i) a peptide of the sequence of HDM03E, HDM202, HDM03W or RGW07D; or (ii) a variant of a peptide according to (i), wherein said variant is a peptide of length 7 to 30 amino acids that comprises a region consisting of:

any of the sequences of (i), or a sequence which has at least 65% homology to any of the sequences of (i); or (iii) a variant of a peptide according to (i), wherein said variant is a peptide of length 7 to 30 amino acids that comprises a region consisting of a sequence that represents either:

a fragment of any of the sequences of (i), or a homologue of a fragment of any of the sequences of (i), wherein said homologue has at least 65% homology to any 7 contiguous amino acids in any of the sequences of (i).

Additionally the first and/or second polypeptides typically do not comprise an epitope capable of cross-linking IgG expressed on the cell surface of B cells or IgE expressed on the surface of mast cells or basophils, and/or may comprise or consist of the minimal MHC Class II-binding sequence of a T cell epitope derived from the protein allergen. The polypeptides of the invention therefore do not induce significant crosslinking of adjacent specific IgE molecules on cells such as mast cells and basophils and consequently do not cause significant histamine release leading to unwanted immune stimulation.

The invention also provides a composition of one or more of the above peptides, a composition comprising one or more polynucleotides which are expressed as the above peptides, and a vector comprising one or more of the above polynucleotides.

SUMMARY OF FIGURES

FIG. 5A shows airway resistance (y axis, cm $H_20$/mL/s) in response to methacholine dosage (x axis, mg/ml) for each of the treatment groups HPVEH (vehicle), and HP10, HP1, HP0.1, HP0.01, HP0.001 (10, 1, 0.1, 0.01 & 0.001 ug of each of HDM03D and HDM202). FIG. 5B shows airway resistance at the 25 mg/ml challenge dose of methacholine (y axis, cm $H_20$/mL/s; x axis: treatment group). FIG. 5C shows the rate of resistance increase (y axis, slope (rate of resistance increase per dose); x axis: treatment group) as calculated from the dose response curve of FIG. 5A.

FIG. 6A shows total number of cells in the BAL (y axis, number of cells in BAL$\times 10^4$, x axis: treatment group). FIGS. 6B, 6C and 6D show respectively absolute numbers of neutrophils, lymphocytes and eosinophils in the BAL fluid (y axis, number of cells in BAL$\times 10^4$, x axis: treatment group).

DETAILED DESCRIPTION

Figure 1:
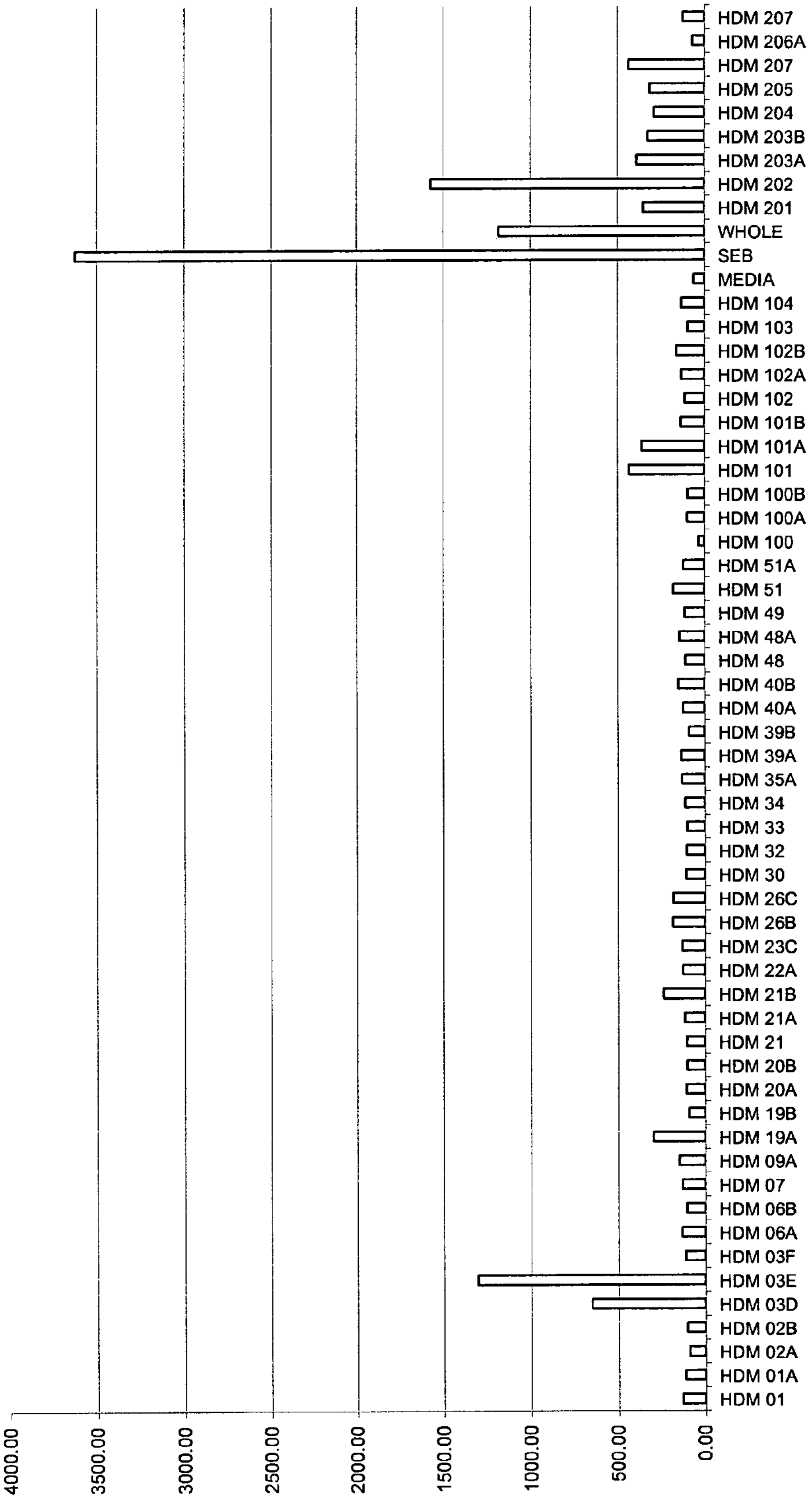
FIGS. 1 and 2 show mean IL-10 release (y axis, pg/ml) in response to the house dust mite peptides shown on the x axis, for a population of dust mite allergic individuals.

The invention relates to peptides that can be used in methods of immune tolerisation. The peptides are fragments of a polypeptide allergen or homologous variants thereof. The peptides are used in induction of immune tolerance against a protein allergen. Peptides derived from a protein allergen are herein generally referred to as "polypeptides", "peptides" or "peptides of the invention". The terms "peptide", "polypeptide" and "protein" are used interchangeably herein.

The peptides may be chemically derived from the polypeptide allergen, for example by proteolytic cleavage or can be derived in an intellectual sense from the polypeptide allergen, for example by making use of the amino acid sequence of the polypeptide allergen and synthesising peptides based on the sequence.

It will be understood that the peptides of the invention comprise a T cell epitope that consists of the minimal essential sequence required for MHC class II binding. The presence of a T cell epitope is necessary in order for the peptide to induce IL-10 release from T cells, and provide for a tolerising effect. The peptide is at least 7 amino acids long, preferably 9 amino acids long, and has a maximum length of 30 amino acids. Preferably, the peptide may be from 9 to 20 or more preferably 13 to 17 amino acids in length. Additionally, the peptides of the invention may represent 10% or less of the whole protein allergen from which they derive. That is to say that a peptide of the invention may be a fragment representing 10% or less of the polypeptide chain of the whole protein allergen from which it derives. Preferably, a peptide of the invention may represent less than 9%, 8%, 7%, 6%, 5%, 4%, 3%, 2%, 1% or less of the whole protein allergen from which it derives.

The first polypeptide of the invention typically possesses one or more functional properties which underlies its ability to act as a tolerising agent. The first polypeptide induces an IL-10 release that is greater than the amount of IL-10 released in response to the whole protein allergen from which the first polypeptide derives. Preferably the first polypeptide may induce an IL-10 release that is at least 120%, 150%, 200%, 250%, 300%, 400%, 500% or greater than the amount of IL-10 released in response to said whole protein allergen. The first polypeptide may induce a release of IL-10 that is greater than whole allergen in at least 35, 40, 45, 50 or 55% of a population. In this embodiment, the peptide is therefore able to bind to a subset of MHC alleles which is representative of an equivalent proportion of the sample population. Preferably, the peptides induce an IL-10 release that is greater than whole allergen in 55% or more, 65% or more, 70% or more, 75% or more, 80% or more, 85% or more, or 90% or more of a population.

"Induction of IL-10 release" is herein defined as a release which is measurable by methods commonly used in the art.

Induction of IL-10 release is measured relative to whole allergen and also relative to a control sample where T cells are not exposed to the peptide. Commonly, the induction of IL-10 release corresponds to an IL-10 level which is at least two, three, four or more times greater than that observed in the control sample. Typically, the response is measured in vitro using T cells obtained from a subject of interest. In some embodiments, the response is measured in vitro using T cells obtained from subjects who are allergic to the protein allergen from which the first polypeptide is derived. The response may be measured according to an in vitro method comprising the steps of:

i) selecting a peptide fragment of a protein allergen consisting of 7 to 30 amino acids in length and comprising at least one MHC Class II-binding T cell epitope;
ii) incubating said peptide with T cells in a plurality of samples taken from different subjects; and
iii) measuring IL-10 release in said cells; and optionally
iv) measuring release of one or more other cytokines.

In preferred embodiments, the method further comprises incubating the whole protein allergen of i) with T cells in a plurality of samples taken from different subjects; measuring the IL-10 release in said cells; and comparing the IL-10 release in the cells of ii) with the IL-10 release in said cells incubated with whole protein allergen to identify a peptide able to induce an IL-10 release that is greater than the amount of IL-10 released in response to the whole protein allergen of i). The above method is provided as part of the present invention. In some embodiments, the subjects may be allergic to the protein allergen of (i).

In some embodiments, an induction of IL-10 release greater than whole allergen may be the average amount of IL-10 released in response to the whole protein allergen of which the first polypeptide is a fragment. Such an average may be calculated as set forth below.

The specified levels of IL-10 release may occur in the relevant subject in response to administration of the first polypeptide.

It should be understood that the protein allergen used as a comparison may be the whole intact polypeptide or may be a truncated form that comprises the T cell epitopes which mediate immune response to the protein allergen. Commonly, individual peptides derived from the protein allergen will show an IL-10 release that is much lower than that obtained in response to the whole or truncated protein allergen as defined above. However, individual peptides that show IL-10 release greater than the IL-10 release to the whole or truncated protein allergen may be particularly suitable tolerising agents. The peptides may also display an average response that is greater than the response observed to whole or truncated protein allergen.

The first polypeptide may also induce the release of an amount of IL-10 which is at least 400 pg/ml. In some embodiments, the IL-10 release may be at least 500 pg/ml, at least 600 pg/ml, at least 700 pg/ml, at least 800 pg/ml, at least 900 pg/ml, or at least 1000 pg/ml or more. The IL-10 release may be the average amount released in a sample subject population. The sample subject population may be allergic to the protein allergen from which the first polypeptide is derived.

It should be understood that an average amount of IL-10 release may be the mean, median or mode of the individual IL-10 releases observed in the population. It should be understood that where a subject in the population displays an unusually low or unusually high IL-10 release in comparison to the other members of the population, they may be excluded from the average. This may allow for measurement of an average that is more representative of the responses shown in the population. The term 'unusually low' or unusually high' may refer to differentials of 10-fold or 20-fold as compared to a more representative average of the IL-10 releases that excludes the individuals showing unusual IL-10 release characteristics. The same considerations apply where other average IL-10 releases are discussed below.

A population herein is a group of 10, 20, 50, 75, 100 or more subjects. Preferably the population consists of 50 or more subjects. In some embodiments the population consists of subjects who are allergic to the whole protein allergen of which the first polypeptide is a fragment, or a variant thereof. In other embodiments, the population may comprise subjects who are also allergic to one or more other protein. In further embodiments, the population may comprise or consist of subjects who are not allergic to the whole protein allergen of which the first polypeptide is a fragment, or homologous variant thereof.

The invention can be carried out on any suitable species of subject. The species is usually an animal (including birds), preferably a mammal or human. Other suitable species include those of the following family, sub family, genus or species:

Ungulates—Family: Suidae, Genus: *Sus* (Pigs)
Family Bovidae, Sub family: Bovinae, Genus: *Bos* (Cows)
Family: Bovidae, Sub family: Carpinae, Genus: *Ovis* (Sheep)
Family: Equidae, Genus: *Equus* (Horses)
Primates: Order: Primates, Sub order: Haplorrhini (Includes Simian Monkeys),
Sub family: Homininae (Gorillas, Chimpanzees)
Tribe: Hominini
Other: Family: Canidae, Genus: *Canis*. (Dogs)
Family: Felidae, Genus: *Felis* (Cats)
Non-tetrapod chordates: Class: Ayes, Order: Galliformes (Land fowl), and Order: Anseriformes (Water Fowl)
Family: Muridae (Rats, Gerbils, Mice, Hamsters)

Where the subject is a human, the population may be selected on an ethnic basis e.g Caucasian, African, Chinese. Selection of a population on an ethnic basis may be useful where the protein allergen is confined largely to a specific geographical area where the residents are mainly of a single ethnic origin. The population may also be selected on the basis of having a mild, moderate or severe allergic response to protein allergen.

Preferably, the individual to be treated is from a population that has MHC allele frequencies within the range of frequencies that are representative of the Caucasian population. Reference population allele frequencies for 11 common DRB1 allele families are shown in Table 1 (Data from HLA Facts Book, Parham and Barber).

TABLE 1

| | DRB1 | | | | | | | | | | |
|---|---|---|---|---|---|---|---|---|---|---|---|
| | 1 | 3 | 4 | 7 | 8 | 11 | 12 | 13 | 14 | 15 | 16 |
| % | 6.4 | 14.7 | 15.7 | 8.8 | 3.4 | 8.3 | 3.9 | 14.7 | 2.9 | 17.6 | 2.5 |
| Reference population % | 9.4 | 11.1 | 12.8 | 13.2 | 3.7 | 13.4 | 2.3 | 10.2 | 3.2 | 10.7 | 3.6 |

Reference frequencies were obtained by analysis of multiple studies reporting frequencies and the figures shown are mean values. Preferably therefore, the individual to be treated is from a population that has equivalent MHC allele frequencies as the reference population for the alleles referred to Table 1 (such as for at least 1, 2, 3, 4, 5 or all of the alleles), for example within the ranges of those figures plus or minus 1, 2, 3, 5, 10, 15 or 20%. Preferably the individual is from a population where the allele frequencies of the following DRB1 alleles is:

4—at least 9%

7—at least 10%

11—at least 8%.

Additionally, where a peptide of the invention does not induce IL-10 release in a high proportion of a population, it may still be used for tailored treatment of specific subsets of allergic individuals. In such an embodiment, a peptide induces an IL-10 release in an individual that is greater than the amount of IL-10 released by the same individual in response to the whole protein allergen of which the first polypeptide is a fragment. This peptide is suitable to use for tolerisation in this individual even if it is not broadly applicable to a larger population.

According to the invention, first and second polypeptides are administered in the method of tolerisation. First and second polypeptides of the invention may be administered sequentially, separately or in combination. Additionally, more than one first and/or second peptide of the invention may be administered to a subject to treat or prevent a disorder by tolerisation. For example, two, three, four, five, six, seven, eight or more peptides of the invention may be administered to a subject. In some embodiments, one first peptide of the invention will be administered together with two, three, four, five, six, seven or more second peptides of the invention. In other embodiments two or more first peptides of the invention may be administered together with one or more second peptides of the invention.

The first and second peptides of the invention are used in a method of immune tolerisation against a protein allergen in a subject showing an inappropriate immune response to that allergen. In some embodiments, the subject is also allergic or mildly allergic to the protein allergen of which the first peptide is a fragment or homologous variant thereof.

The term “tolerisation” refers to an ability to suppress, or abolish an allergic response to the protein allergen. Tolerisation is also an ability to diminish or abolish an unwanted immune response, or to desensitise a subject to a protein allergen. Tolerisation may be determined by in vitro analysis of T cell responses or by observation of a reduction in the symptoms in an individual. In some embodiments, the peptides may provide tolerisation to more than one protein allergen.

The tolerisation effect may be observed on sole administration of the peptides of the invention, to create a tolerising environment for a potential encounter with a protein allergen. Thus where a hyporesponsive state has been established by the peptides of the invention, or there has been at least a shift toward desensitisation of the immune system, this will act as a prophylaxis against an unwanted immune response where a protein allergen is then encountered.

It should be understood that the second peptide of the invention is derived from the protein allergen to which an inappropriate immune response is present. Therefore, administration of the second polypeptide in the context of the first polypeptide allows for tolerisation against the whole protein allergen from which the second polypeptide is derived. However, in other embodiments the peptides of the invention may be administered sequentially, separately or in combination with whole protein allergen. This allows for the peptides to induce the tolerising effect at the same time as immune responses are being elicited against the protein allergen. Accordingly, an allergic-type reaction against T cell epitopes derived from the protein allergen can be converted into a tolerisation effect by the IL-10 releasing property of the first peptides of the invention.

In some embodiments the first peptide is used for tolerisation of subjects who exhibit low levels of IL-10 release in response to the protein allergen or second peptide administered alone. Such subjects may be identified by the diagnostic methods described below. Such subjects may be characterised in that they are not tolerised by administration of the second peptide or protein allergen alone.

It should be understood that the above uses of whole protein allergen are not limited to administration of intact protein allergen to the subjects. Typically, the protein allergen will be administered in the form of one or more peptides comprising MHC-Class II binding T cell epitopes derived from the second protein. Such peptides may be modified or engineered for solubility according to the criteria set out below in relation to peptides derived from the first allergen.

The tolerising effect of the peptides of the invention may be exploited propylactically or therapeutically. Accordingly, peptides of the invention are provided for use in treating or preventing a disease by tolerisation of an individual to the protein allergen, typically an allergic disease.

Protein allergens include, but are not limited to dust mite allergens, pollens, animal dander (especially cat dander), grasses, molds, dusts, antibiotics, stinging insect venoms, and a variety of environmental (including chemicals and metals), drug and food allergens. Common tree allergens include pollens from cottonwood, popular, ash, birch, maple, oak, elm, hickory, and pecan trees; common plant allergens include those from mugwort, ragweed, English plantain, sorrel-dock and pigweed; plant contact allergens include those from poison oak, poison ivy and nettles; common grass allergens include rye grass, Timothy, Johnson, Bermuda, fescue and bluegrass allergens; common allergens can also be obtained from molds or fungi such as Alternaria, Cladosporium, Fusarium, Hormodendrum, Aspergillus, Micropolyspora, Mucor and thermophilic actinomycetes; epidermal allergens can be obtained from house or organic dusts (typically fungal in origin), or from animal sources such as feathers, and dog dander; common food allergens include milk and cheese (dairy), egg, wheat, nut (e.g., peanut), seafood (e.g., shellfish), pea, bean and gluten allergens; common environmental allergens include metals (nickel and gold), chemicals (formaldehyde, trinitrophenol and turpentine), Latex, rubber, fiber (cotton or wool), burlap, hair dye, cosmetic, detergent and perfume allergens; common drug allergens include local anesthetic and salicylate allergens; antibiotic allergens include penicillin, tetracycline and sulfonamide allergens; and common insect allergens include bee, wasp and ant venom, and cockroach calyx allergens. Particularly well characterized allergens include, but are not limited to, the major cat allergen Fel dl, bee venom phospholipase A2 (PLA) (Akdis et al. (1996) J. Clin. Invest. 98:1676-1683), birch pollen allergen Bet v 1 (Bauer et al. (1997) Clin. Exp. Immunol. 107:536-541), and the multi-epitopic recombinant grass allergen rKBG8.3 (Cao et al. (1997) Immunology 90:46-51).

The first and second polypeptides of the invention may be derived_from plant allergens, animal dander allergens, a mold or fungal allergen, a dust allergen, an antibiotic or other drug, a stinging insect venom, an environmental allergen or a food allergen and combinations thereof.

Particularly preferred T cell epitopes are derived from the allergens: cat dander protein Fel d1; House dust mite proteins Der p 1, Der p 2 and Der p 7; Ragweed protein amb a 1

(specifically amb a 1.1, a 1.2, a 1.3 or a 1.4); Alternaria alternata proteins Alt a 1, Alt a 2, Enolase (Alt a 6), Alt a 10, Alt a 13; Cladosporium herbarum proteins Cla h 6, Cla h 8; Birch proteins Bet v1, Bet v 2, Bet v 3, Bet v 4, Bet v 6 and P14; German Cockroach proteins Bla g 1, Bla g 2, Bla g 3, Bla g 4, Bla g 5 and Bla g 6; Mugwort protein Art v 1; Russian thistle protein Sal k 1 and Sal k2; peanut Ara h 1, Ara h 2, Ara h 3, Ara h 4, Ara h 5, Ara h 6, plant profilins or lipid transfer proteins or a human leukocyte antigen.

These and other suitable allergens are commercially available and/or can be readily prepared as extracts following known techniques.

Preferably, the allergen is selected from the list of whole allergen and allergen fragment sequences and database accession numbers (NCBI Entrez accession numbers) below. NCBI is the National Center for Biotechnology information and is a division of the US National Institutes of Health. The NCBI web site, from which access to the database may be sought, is www.ncbi.nlm.nih.gov/. Allergen sequences and database accession numbers (NCBI Entrez accession numbers):

House Dust Mite

Dermatophagoides pteronyssinus

Der p 1

(SEQ ID NO: 11)

MKIVLAIASLLALSAVYARPSSIKTFEEYKKAFNKSYATFEDEEAARKNFLESVKYVQSNGGAINH

LSDLSLDEFKNRFLMSAEAFEHLKTQFDLNAETNACSINGNAPAEIDLRQMRTVTPIRMQGGCGSCWAFSGV

AATESAYLAYRNQSLDLAEQELVDCASQHGCHGDTIPRGIEYIQHNGVVQESYYRYVAREQSCRRPNAQRF

GISNYCQIYPPNVNKIREALAQTHSAIAVIIGIKDLDAFRHYDGRTIIQRDNGYQPNYHAVNIVGYSNAQGVD

YWIVRNSWDTNWGDNGYGYFAANIDLMMIEEYPYVVIL

Der p 2

(SEQ ID NO: 12)

MMYKILCLSLLVAAVARDQVDVKDCANHEIKKVLVPGCHGSEPCIIHRGKPFQLEAVFEANQNTK

TAKIEIKASIDGLEVDVPGIDPNACHYMKCPLVKGQQYDIKYTWNVPKIAPKSENVVVTVKVMGDDGVLAC

AIATHAKIRD

Der p 3

(SEQ ID NO: 13)

MIIYNILIVLLLAINTLANPILPASPNATIVGGEKALAGECPYQISLQSSSHFCGGTILDEYWILTAAH

CVAGQTASKLSIRYNSLKHSLGGEKISVAKIFAHEKYDSYQIDNDIALIKLKSPMKLNQKNAKAVGLPAKGS

DVKVGDQVRVSGWGYLEEGSYSLPSELRRVDIAVVSRKECNELYSKANAEVTDNMICGGDVANGGKDSCQ

GDSGGPVVDVKNNQVVGIVSWGYGCARKGYPGVYTRVGNFIDWIESKRSQ

Der p 4

(SEQ ID NO: 14)

KYXNPHFIGXRSVITXLME

Der p 5

(SEQ ID NO: 15)

MKFIIAFFVATLAVMTVSGEDKKHDYQNEFDFLLMERIHEQIKKGELALFYLQEQINHFEEKPTKE

MKDKIVAEMDTIIAMIDGVRGVLDRLMQRKDLDIFEQYNLEMAKKSGDILERDLKKEEARVKKIEV

Der p 6

(SEQ ID NO: 16)

AIGXQPAAEAEAPFQISLMK

Der p 7

(SEQ ID NO: 17)

MMKLLLIAAAAFVAVSADPIHYDKITEEINKAVDEAVAAIEKSETFDPMKVPDHSDKFERHIGIIDL

KGELDMRNIQVRGLKQMKRVGDANVKSEDGVVKAHLLVGVHDDVVSMEYDLAYKLGDLHPNTHVISDIQ

DFVVELSLEVSEEGNMTLTSFEVRQFANVVNHIGGLSILDPIFAVLSDVLTAIFQDTVRAEMTKVLAPAFKKE

LERNNQ

Der p9

(SEQ ID NO: 18)

IVGGSNASPGDAVYQIAL

Dermatophagoides farinae

Der f 1

(SEQ ID NO: 19)

MKFVLAIASLLVLTVYARPASIKTFEFKKAFNKNYATVEEEEVARKNFLESLKYVEANKGAINHLS

DLSLDEFKNRYLMSAEAFEQLKTQFDLNAETSACRINSVNVPSELDLRSLRTVTPIRMQGGCGSCWAFSGVA

-continued

ATESAYLAYRNTSLDLSEQELVDCASQHGCHGDTIPRGIEYIQQNGVVEERSYPYVAREQRCRRPNSQHYGI

SNYCQIYPPDVKQIREALTQTHTAIAVIIGIKDLRAFQHYDGRTIIQHDNGYQPNYHAVNIVGYGSTQGDDY

WIVRNSWDTTWGDSGYGYFQAGNNLMMIEQYPYVVIM

Der f 2

(SEQ ID NO: 20)

MISKILCLSLLVAAVVADQVDVKDCANNEIKKVMVDGCHGSDPCIIHRGKPFTLEALFDANQNTK

TAKIEIKASLDGLEIDVPGIDTNACHFMKCPLVKGQQYDIKYTWNVPKIAPKSENVVVTVKLIGDNGVLACA

IATHGKIRD

Der f 3

(SEQ ID NO: 21)

MMILTIVVLLAANILATPILPSSPNATIVGGVKAQAGDCPYQISLQSSSHFCGGSILDEYWILTAAHC

VNGQSAKKLSIRYNTLKHASGGEKIQVAEIYQHENYDSMTIDNDVALIKLKTPMTLDQTNAKPVPLPAQGS

DVKVGDKIRVSGWGYLQEGSYSLPSELQRVDIDVVSREQCDQLYSKAGADVSENMICGGDVANGGVDSCQ

GDSGGPVVDVATKQIVGIVSWGYGCARKGYPGVYTRVGNFVDWIESKRSQ

Der f 4

(SEQ ID NO: 22)

AVGGQDADLAEAPFQISLLK

Der f 7

(SEQ ID NO: 23)

MMKFLLIAAVAFVAVSADPIHYDKITEEINKAIDDAIAAIEQSETIDPMKVPDHADKFERHVGIVDF

KGELAMRNIEARGLKQMKRQGDANVKGEEGIVKAHLLIGVHDDIVSMEYDLAYKLGDLHPTTHVISDIQDF

VVALSLEISDEGNITMTSFEVRQFANVVNHIGGLSILDPIFGVLSDVLTAIFQDTVRKEMTKVLAPAFKRELEKN

Additional mite allergen sequences (NCBI entrez accession):

1170095; 1359436; 2440053; 666007; 487661; 1545803; 84702; 84699; 625532; 404370; 1091577; 1460058; 7413; 9072; 387592.

Cat

*Felis* Sequences (NCBI Entrez Accession):

539716; 539715; 423193; 423192; 423191; 423190; 1364213; 1364212; 395407; 163827; 163823; 163825; 1169665; 232086; 1169666.

Latex

Hevea Sequences:

Hev b 1

(SEQ ID NO: 24)

MAEDEDNQQGQGEGLKYLGFVQDAATYAVTTFSNVYLFAKDKSGPLQPGV

DIIEGPVKNVAVPLYNRFSYIPNGALKFVDSTVVASVTIIDRSLPPIVKD

ASIQVVSAIRAAPEAARSLASSLPGQTKILAKVFYGEN

Hev b 3

(SEQ ID NO: 25)

MAEEVEEERLKYLDFVRAAGVYAVDSFSTLYLYAKDISGPLKPGVDTIEN

VVKTVVTPVYYIPLEAVKFVDKTVDVSVTSLDGVVPPVIKQVSAQTYSVA

QDAPRIVLDVASSVFNTGVQEGAKALYANLEPKAEQYAVITWRALNKLPL

YVPQVANVVVPTAVFSEKYNDVVRGTTEQGYRVSSYLPLLPTEKITKVFG

DEAS

Additional Hevea sequences (NCBI entrez accession):

3319923; 3319921; 3087805; 1493836; 1480457; 1223884; 3452147; 3451147; 1916805; 232267; 123335; 2501578; 3319662; 3288200; 1942537; 2392631; 2392630; 1421554; 1311006; 494093; 3183706; 3172534; 283243; 1170248; 1708278; 1706547; 464775; 266892; 231586; 123337; 116359; 123062; 2213877; 542013; 2144920; 1070656; 2129914; 2129913; 2129912; 100135; 82026; 1076559; 82028; 82027; 282933; 280399; 100138; 1086972; 108697; 1086976; 1086978; 1086978; 1086976; 1086974; 1086972; 913758; 913757; 913756; 234388; 1092500; 228691; 1177405; 18839; 18837; 18835; 18833; 18831; 1209317; 1184668; 168217; 168215; 168213; 168211; 168209; 348137.

Parietaria

Parietaria Sequences:

2497750 Par j P2

(SEQ ID NO: 26)

MRTVSMAALVVIAAALAWTSSAEPAPAPAPGEEACGKVVQDIMPCLHFVK

GEEKEPSKECCSGTKKLSEEVKTTEQKREACKCIVRATKGISGIKNELVA

EVPKKCDIKTTLPPITADFDCSKIQSTIFRGYY

1352506 Par j P5

(SEQ ID NO: 27)

MVRALMPCLPFVQGKEKEPSKGCCSGAKRLDGETKTGPQRVHACECIQT

AMKTYSDIDGKLVSEVPKHCGIVDSKLPPIDVNMDCKTVGVVPRQPQLP

VSLRHGPVTGPSDPAHKARLERPQIRVPPPAPEKA

1532056 Par j P8

(SEQ ID NO: 28)

MRTVSMAALVVIAAALAWTSSAELASAPAPGEGPCGKVVHHIMPCLKFVK

GEEKEPSKSCCSGTKKLSEEVKTTEQKREACKCIVAATKGISGIKNELVA

EVPKKCGITTTLPPITADFDCSKIESTIFRGYY

1532058 Par j P9

(SEQ ID NO: 29)

MRTVSAPSAVALVVIVAAGLAWTSLASVAPPAPAPGSEETCGTVVRALMP

CLPFVQGKEKEPSKGCCSGAKRLDGETKTGLQRVHACECIQTAMKTYSDI

-continued

DGKLVSEVPKHCGIVDSKLPPIDVNMDCKTLGVVPRQPQLPVSLRHGPVT

GPSDPAHKARLERPQIRVPPPAPEKA

2497749 Par j P9

(SEQ ID NO: 30)

MRTVSARSSVALVVIVAAVLVWTSSASVAPAPAPGSEETCGTVVGALMPC

LPFVQGKEKEPSKGCCSGAKRLDGETKTGPQRVHACECIQTAMKTYSDID

GKLVSEVPKHCGIVDSKLPPIDVNMDCKTLGVLHYKGN

1086003 Par j 1

(SEQ ID NO: 31)

MVRALMPCLPFVQGKEKEPSKGCCSGAKRLDGETKTGPQRVHACECIQTA

MKTYSDIDGKLVSEVPKHCGIVDSKLPPIDVNMDCKTVGVVPRQPQLPVS

LRHGPVTGPSRSRPPTKHGWRDPRLEFRPPHRKKPNPAFSTLG

Additional Parietaria sequences (NCBI entrez accession):

543659; 1836011; 1836010; 1311513; 1311512; 1311511; 1311510; 1311509; 240971.

Wasp (and Related) Vespula Sequences:

465054 ALLERGEN Ves v 5

(SEQ ID NO: 32)

MEISGLVYLIIIVTIIDLPYGKANNYCKIKCLKGGVHTACKYGSLKPNCGN

KVVVSYGLTKQEKQDILKEHNDFRQKIARGLETRGNPGPQPPAKNMKNLVW

NDELAYVAQVWANQCQYGHDTCRDVAKYQVGQNVALTGSTAAKYDDPVKLV

KMWEDEVKDYNPKKKFSGNDFLKTGHYTQMVWANTKEVGCGSIKYIQEKWH

KHYLVCNYGPSGNFMNEELYQTK

1709545 ALLERGEN Ves m 1

(SEQ ID NO: 33)

GPKCPFNSDTVSIIIETRENRNRDLYTLQTLQNHPEFKKKTITRPVVFITH

GFTSSASEKNFINLAKALVDKDNYMVISIDWQTAACTNEYPGLKYAYYPTA

ASNTRLVGQYIATITQKLVKDYKISMANIRLIGHSLGAHVSGFAGKRVQEL

KLGKYSEIIGLDPARPSFDSNHCSERLCETDAEYVQIIHTSNYLGTEKILG

TVDFYMNNGKNNPGCGRFFSEVCSHTRAVIYMAECIKHECCLIGIPRSKSS

QPISRCTKQECVCVGLNAKKYPSRGSFYVPVESTAPFCNNKGKII

1352699 ALLERGEN Ves v 1

(SEQ ID NO: 34)

MEENMNLKYLLLFVYFVQVLNCCYGHGDPLSYELDRGPKCPFNSDTVSIII

ETRENRNRDLYTLQTLQNHPEFKKKTITRPVVFITHGFTSSASETNFINLA

KALVDKDNYMVISIDWQTAACTNEAAGLKYLYYPTAARNTRLVGQYIATIT

QKLVKHYKISMANIRLIGHSLGAHASGFAGKKVQELKLGKYSEIIGLDPAR

PSFDSNHCSERLCETDAEYVQIIHTSNYLGTEKTLGTVDFYMNNGKNQPGC

GRFFSEVCSHSRAVIYMAECIKHECCLIGIPKSKSSQPISSCTKQECVCVG

LNAKKYPSRGSFYVPVESTAPFCNNKGKII

1346323 ALLERGEN Ves v 2

(SEQ ID NO: 35)

SERPKRVFNIYWNVPTFMCHQYDLYFDEVTNFNIKRNSKDDFQGDKIAIFY

DPGEFPALLSLKDGKYKKRNGGVPQEGNITIHLQKFIENLDKIYPNRNFSG

IGVIDFERWRPIFRQNWGNMKIHKNFSIDLVRNEHPTWNKKMIELEASKRF

EKYARFFMEETLKLAKKTRKQADWGYYGYPYCFNMSPNNLVPECDVTAMHE

NDKMSWLFNNQNVLLPSVYVRQELTPDQRIGLVQGRVKEAVRISNNLKHSP

-continued

KVLSYWWYVYQDETNTFLTETDVKKTFQEIVINGGDGIIIWGSSSDVNSLS

KCKRLQDYLLTVLGPIAINVTEAVN

549194 ALLERGEN Ves vI (SEQ ID NO: 37)

5KVNYCKIKCLKGGVHTACKYGTSTKPNCGKMVVKAYGLTEAEKQEILKVH

NDFRQKVAKGLETRGNPGPQPPAKNMNNLVWNDELANIAQVWASQCNYGHD

TCKDTEKYPVGQNIAKRSTTAALFDSPGKLVKMWENEVKDFNPNIEWSKNN

LKKTGHYTQMVWAKTKEIGCGSVKYVKDEWYTHYLVCNYGPSGNFRNEKLY

EKK

Additional Vespula Sequences (NCBI Entrez Accession):

549193; 549192; 549191; 549190; 549189; 117414; 126761; 69576; 625255; 627189; 627188; 627187; 482382; 112561; 627186; 627185; 1923233; 897645; 897647; 745570; 225764; 162551.

Tree Allergen Sequences:

Birch

114922 Bet v 1

(SEQ ID NO: 38)

MGVFNYETETTSVIPAARLFKAFILDGDNLFPKVAPQAISSVENIEGNGG

PGTIKKISFPEGFPFKYVKDRVDEVDHTNFKYNYSVIEGGPIGDTLEKIS

NEIKIVATPDGGSILKISNKYHTKGDHEVKAEQVKASKEMGETLLRAVES

YLLAHSDAYN

130975 Bet v 2

(SEQ ID NO: 39)

MSWQTYVDEHLMCDIDGQASNSLASAIVGHDGSVWAQSSSFPQFKPQEIT

GIMKDFEEPGHLAPTGLHLGGIKYMVIQGEAGAVIRGKKGSGGITIKKTG

QALVFGIYEEPVTPGQCNMVVERLGDYLIDQGL

1168696 Bet v 3

(SEQ ID NO: 40)

MPCSTEAMEKAGHGHASTPRKRSLSNSSFRLRSESLNTLRLRRIFDLFDK

NSDGIITVDELSRALNLLGLETDLSELESTVKSFTREGNIGLQFEDFISL

HQSLNDSYFAYGGEDEDDNEEDMRKSILSQEEADSFGGFKVFDEDGDGYI

SARELQMVLGKLGFSEGSEIDRVEKMIVSVDSNRDGRVDFFEFKDMMRSV

LVRSS

809536 Bet v 4

(SEQ ID NO: 41)

MADDHPQDKAERERIFKRFDANGDGKISAAELGEALKTLGSITPDEVKHM

MAEIDTDGDGFISFQEFTDFGRANRGLLKDVAKIF

543675 Que a I -

*Quercus alba* = oak trees (fragment)

(SEQ ID NO: 42)

GVFTXESQETSVIAPAXLFKALFL

543509 Car b I -

*Carpinus betulus* = hornbeam trees (fragment)

(SEQ ID NO: 43)

GVFNYEAETPSVIPAARLFKSYVLDGDKLIPKVAPQAIXK

543491 Aln g I -

*Alnus glutinosa* = alder trees (fragment)

(SEQ ID NO: 44)

GVFNYEAETPSVIPAARLFKAFILDGDKLLPKVAPEAVSSVENI

-continued

1204056 Rubisco (SEQ ID NO: 45)

VQCMQVWPPLGLKKFETLSYLPPLSSEQLAKEVDYLLRKNLIPCLEFELE

HGFVYREHNRSPGYYDGRYWTMWKLPMFGCNDSSQVLKELEECKKAYPSA

FIRIIGFDDK

Additional Tree Allergen Sequences (NCBI Entrez Accession Number):

131919; 128193; 585564; 1942360; 2554672; 2392209; 2414158; 1321728; 1321726; 1321724; 1321722; 1321720; 1321718; 1321716; 1321714; 1321712; 3015520; 2935416; 464576; 1705843; 1168701; 1168710; 1168709; 1168708; 1168707; 1168706; 1168705; 1168704; 1168703; 1168702; 1842188; 2564228; 2564226; 2564224; 2564222; 2564220; 2051993; 1813891; 1536889; 534910; 534900; 534898; 1340000; 1339998; 2149808; 66207; 2129477; 1076249; 1076247; 629480; 481805; 81443; 1361968; 1361967; 1361966; 1361965; 1361964; 1361963; 1361962; 1361961; 1361960; 1361959; 320546; 629483; 629482; 629481; 541804; 320545; 81444; 541814; 629484; 474911; 452742; 1834387; 298737; 298736; 1584322; 1584321; 584320; 1542873; 1542871; 1542869; 1542867; 1542865; 1542863; 1542861; 1542859; 1542857; 1483232; 1483230; 1483228; 558561; 551640; 488605; 452746; 452744; 452740; 452738; 452736; 452734; 452732; 452730; 452728; 450885; 17938; 17927; 17925; 17921; 297538; 510951; 289331; 289329; 166953.

Cedar Sequences

493634 Cry j IB precursor (SEQ ID NO: 46)

MDSPCLVALLVFSFVIGSCFSDNPIDSCWRGDSNWAQNRMKLADCAVGFG

SSTMGGKGGDLYTVTNSDDDPVNPPGTLRYGATRDRPLWIIFSGNMNIKL

KMPMYIAGYKTFDGRGAQVYIGNGGPCVFIKRVSNVIIHGLYLYGCSTSV

LGNVLINESFGVEPVHPQDGDALTLRTATNIWIDHNSFSNSSDGLVDVTL

TSTGVTISNNLFFNHHKVMSLGHDDAYSDDKSMKVTVAFNQFGPNCGQRM

PRARYGLVHVANNNYDPWTIYAIGGSSNPTILSEGNSFTAPNESYKKQVT

IRIGCKTSSSCSNWVWQSTQDVFYNGAYFVSSGKYEGGNIYTKKEAFNVE

NGNATPHLTQNAGVLTCSLSKRC

493632 Cry j IA precursor (SEQ ID NO: 47)

MDSPCLVALLVLSFVIGSCFSDNPIDSCWRGDSNWAQNRMKLADCAVGFG

SSTMGGKGGDLYTVTNSDDDPVNPAPGTLRYGATRDRPLWIIFSGNMNIK

LKMPMYIAGYKTFDGRGAQVYIGNGGPCVFIKRVSNVIIHGLHLYGCSTS

VLGNVLINESFGVEPVHPQDGDALTLRTATNIWIDHNSFSNSSDGLVDVT

LSSTGVTISNNLFFNHHKVMLLGHDDAYSDDKSMKVTVAFNQFGPNCGQR

MPRARYGLVHVANNNYDPWTIYAIGGSSNPTILSEGNSFTAPNESYKKQV

TIRIGCKTSSSCSNWVWQSTQDVFYNGAYFVSSGKYEGGNIYTKKEAFNV

ENGNATPQLTKNAGVLTCSLSKRC

1076242 Cry j II precursor - Japanese cedar (SEQ ID NO: 48)

MAMKLIAPMAFLAMQLIIMAAAEDQSAQIMLDSVVEKYLRSNRSLRKVEH

SRHDAINIFNVEKYGAVGDGKHDCTEAFSTAWQAACKNPSAMLLVPGSKK

-continued

FVVNNLFFNGPCQPHFTFKVDGIIAAYQNPASWKNNRIWLQFAKLTGFTL

MGKGVIDGQGKQWWAGQCKWVNGREICNDRDRPTAIKFDFSTGLIIQGLK

LMNSPEFHLVFGNCEGVKIIGISITAPRDSPNTDGIDIFASKNFHLQKNT

IGTGDDCVAIGTGSSNIVIEDLICGPGHGISIGSLGRENSRAEVSYVHVN

GAKFIDTQNGLRIKTWQGGSGMASHIIYENVEMINSENPILINQFYCTSA

SACQNQRSAVQIQDVTYKNIRGTSATAAAIQLKCSDSMPCKDIKLSDISL

KLTSGKIASCLNDNANGYFSGHVIPACKNLSPSAKRKESKSHKHPKTVMV

ENMRAYDKGNRTRILLGSRPPNCTNKCHGCSPCKAKLVIVHRIMPQEYYP

QRWICSCHGKIYHP

1076241 Cry j II protein - Japanese cedar (SEQ ID NO: 49)

MAMKFIAPMAFVAMQLIIMAAAEDQSAQIMLDSDIEQYLRSNRSLRKVEH

SRHDAINIFNVEKYGAVGDGKHDCTEAFSTAWQAACKKPSAMLLVPGNKK

FVVNNLFFNGPCQPHFTFKVDGIIAAYQNPASWKNNRIWLQFAKLTGFTL

MGKGVIDGQGKQWWAGQCKWVNGREICNDRDRPTAIKFDFSTGLIIQGLK

LMNSPEFHLVFGNCEGVKIIGISITAPRDSPNTDGIDIFASKNFHLQKNT

IGTGDDCVAIGTGSSNIVIEDLICGPGHGISIGSLGRENSRAEVSYVHVN

GAKFIDTQNGLRIKTWQGGSGMASHIIYENVEMINSENPILINQFYCTSA

SACQNQRSAVQIQDVTYKNIRGTSATAAAIQLKCSDSMPCKDIKLSDISL

KLTSGKIASCLNDNANGYFSGHVIPACKNLSPSAKRKESKSHKHPKTVMV

KNMGAYDKGNRTRILLGSRPPNCTNKCHGCSPCKAKLVIVHRIMPQEYYP

QRWMCSRHGKIYHP

541803 Cry j I precursor - Japanese cedar (SEQ ID NO: 50)

MDSPCLVALLVLSFVIGSCFSDNPIDSCWRGDSNWAQNRMKLADCAVGFG

SSTMGGKGGDLYTVTNSDDDPVNPPGTLRYGATRDRPLWIIFSGNMNIKL

KMPMYIAGYKTFDGRGAQVYIGNGGPCVFIKRVSNVIIHGLHLYGCSTSV

LGNVLINESFGVEPVHPQDGDALTLRTATNIWIDHNSFSNSSDGLVDVTL

SSTGVTISNNLFFNHHKVMLLGHDDAYSDDKSMKVTVAFNQFGPNCGQRM

PRARYGLVHVANNNYDPWTIYAIGGSSNPTILSEGNSFTAPNESYKKQVT

IRIGCKTSSSCSNWVWQSTQDVFYNGAYFVSSGKYEGGNIYTKKEAFNVE

NGNATPQLTKNAGVLTCSLSKRC

541802 Cry j I precursor - Japanese cedar (SEQ ID NO: 51)

MDSPCLVALLVFSFVIGSCFSDNPIDSCWRGDSNWAQNRMKLADCAVGFG

SSTMGGKGGDLYTVTNSDDDPVNPAPGTLRYGATRDRPLWIIFSGNMNIK

LKMPMYIAGYKTFDGRGAQVYIGNGGPCVFIKRVSNVIIHGLYLYGCSTS

VLGNVLINESFGVEPVHPQDGDALTLRTATNIWIDHNSFSNSSDGLVDVT

LTSTGVTISNNLFFNHHKVMSLGHDDAYSDDKSMKVTVAFNQFGPNCGQR

MPRARYGLVHVANNNYDPWTIYAIGGSSNPTILSEGNSFTAPNESYKKQV

TIRIGCKTSSSCSNWVWQSTQDVFYNGAYFVSSGKYEGGNIYTKKEAFNV

ENGNATPHLTQNAGVLTCSLSKRC

Olive Tree
Olive Sequences

416610 Ole e 1

(SEQ ID NO: 52)

EDIPQPPVSQFHIQGQVYCDTCRAGFITELSEFIPGASLRLQCKDKE

NGDVTFTEVGYTRAEGLYSMLVERDHKNEFCEITLISSGRKDCNEIPT

EGWAKPSLKFKLNTVNGTTRTVNPLGFFKKEALPKCAQVYNKLGMY

PPNM

Peanut
Peanut Sequences

1168391 Ara h 1

(SEQ ID NO: 53)

MRGRVSPLMLLLGILVLASVSATHAKSSPYQKKTENPCAQRCLQSCQQE

PDDLKQKACESRCTKLEYDPRCVYDPRGHTGTTNQRSPPGERTRGRQPG

DYDDDRRQPRREEGGRWGPAGPREREREEDWRQPREDWRRPSHQQPRKI

RPEGREGEQEWGTPGSHVREETSRNNPFYFPSRRFSTRYGNQNGRIRVL

QRFDQRSRQFQNLQNHRIVQIEAKPNTLVLPKHADADNILVIQQGQATV

TVANGNNRKSFNLDEGHALRIPSGFISYILNRHDNQNLRVAKISMPVNT

PGQFEDFFPASSRDQSSYLQGFSRNTLEAAFNAEFNEIRRVLLEENAGG

EQEERGQRRWSTRSSENNEGVIVKVSKEHVEELTKHAKSVSKKGSEEEG

DITNPINLREGEPDLSNNFGKLFEVKPDKKNPQLQDLDMMLTCVEIKEG

ALMLPHFNSKAMVIVVVNKGTGNLELVAVRKEQQQRGRREEEEDEDEEE

EGSNREVRRYTARLKEGDVFIMPAAHPVAINASSELHLLGFGINAENNH

RIFLAGDKDNVIDQIEKQAKDLAFPGSGEQVEKLIKNQKESHFVSARPQ

SQSQSPSSPEKESPEKEDQEEENQGGKGPLLSILKAFN

Ragweed
Ambrosia Sequences

113478 Amb a 1

(SEQ ID NO: 54)

MGIKHCCYILYFTLALVTLLQPVRSAEDLQQILPSANETRSLTTCGTYN

IIDGCWRGKADWAENRKALADCAQGFAKGTIGGKDGDIYTVTSELDDDV

ANPKEGTLRFGAAQNRPLWIIFARDMVIRLDRELAINNDKTIDGRGAKV

EIINAGFAIYNVKNIIIHNIIMHDIVVNPGGLIKSHDGPPVPRKGSDGD

AIGISGGSQIWIDHCSLSKAVDGLIDAKHGSTHFTVSNCLFTQHQYLLL

FWDFDERGMLCTVAFNKFTDNVDQRMPNLRHGFVQVVNNNYERWGSYAL

GGSAGPTILSQGNRFLASDIKKEVVGRYGESAMSESINWNWRSYMDVFE

NGAIFVPSGVDPVLTPEQNAGMIPAEPGEAVLRLTSSAGVLSCQPGAPC

113479 Amb a 2

(SEQ ID NO: 55)

MGIKHCCYILYFTLALVTLVQAGRLGEEVDILPSPNDTRRSLQGCEAHN

IIDKCWRCKPDWAENRQALGNCAQGFGKATHGGKWGDIYMVTSDQDDDV

VNPKEGTLRFGATQDRPLWIIFQRDMIIYLQQEMVVTSDKTIDGRGAKV

ELVYGGITLMNVKNVIIHNIDIHDVRVLPGGRIKSNGGPAIPRHQSDGD

AIHVTGSSDIWIDHCTLSKSFDGLVDVNWGSTGVTISNCKFTHHEKAVL

-continued

LGASDTHFQDLKMHVTLAYNIFTNTVHERMPRCRFGFFQIVNNFYDRWD

KYAIGGSSNPTILSQGNKFVAPDFIYKKNVCLRTGAQEPEWMTWNWRTQ

NDVLENGAIFVASGSDPVLTAEQNAGMMQAEPGDMVPQLTMNAGVLTCS

PGAPC

113477 Amb a 1.3

(SEQ ID NO: 56)

MGIKQCCYILYFTLALVALLQPVRSAEGVGEILPSVNETRSLQACEALN

IIDKCWRGKADWENNRQALADCAQGFAKGTYGGKWGDVYTVTSNLDDDV

ANPKEGTLRFAAAQNRPLWIIFKNDMVINLNQELVVNSDKTIDGRGVKV

EIINGGLTLMNVKNIIIHNINIHDVKVLPGGMIKSNDGPPILRQASDGD

TINVAGSSQIWIDHCSLSKSFDGLVDVTLGSTHVTISNCKFTQQSKAIL

LGADDTHVQDKGMLATVAFNMFTDNVDQRMPRCRFGFFQVVNNNYDRWG

TYAIGGSSAPTILCQGNRFLAPDDQIKKNVLARTGTGAAESMAWNWRSD

KDLLENGAIFVTSGSDPVLTPVQSAGMIPAEPGEAAIKLTSSAGVFSCH

PGAPC

113476 Amb a 1.2

(SEQ ID NO: 57)

MGIKHCCYILYFTLALVTLLQPVRSAEDVEEFLPSANETRRSLKACEAH

NIIDKCWRCKADWANNRQALADCAQGFAKGTYGGKHGDVYTVTSDKDDD

VANPKEGTLRFAAAQNRPLWIIFKRNMVIHLNQELVVNSDKTIDGRGVK

VNIVNAGLTLMNVKNIIIHNINIHDIKVCPGGMIKSNDGPPILRQQSDG

DAINVAGSSQIWIDHCSLSKASDGLLDITLGSSHVTVSNCKFTQHQFVL

LLGADDTHYQDKGMLATVAFNMFTDHVDQRMPRCRFGFFQVVNNNYDRW

GTYAIGGSSAPTILSQGNRFFAPDDIIKKNVLARTGTGNAESMSWNWRT

DRDLLENGAIFLPSGSDPVLTPEQKAGMIPAEPGEAVLRLTSSAGVLSC

HQGAPC

113475 Amb a 1.1

(SEQ ID NO: 58)

MGIKHCCYILYFTLALVTLLQPVRSAEDLQEILPVNETRRLTTSGAYNI

IDGCWRGKADWAENRKALADCAQGFGKGTVGGKDGDIYTVTSELDDDVA

NPKEGTLRFGAAQNRPLWIIFERDMVIRLDKEMVVNSDKTIDGRGAKVE

IINAGFTLNGVKNVIIHNINMHDVKVNPGGLIKSNDGPAAPRAGSDGDA

ISISGSSQIWIDHCSLSKSVDGLVDAKLGTTRLTVSNSLFTQHQFVLLF

GAGDENIEDRGMLATVAFNTFTDNVDQRMPRCRHGFFQVVNNNYDKWGS

YAIGGSASPTILSQGNRFCAPDERSKKNVLGRHGEAAAESMKWNWRTNK

DVLENGAIFVASGVDPVLTPEQSAGMIPAEPGESALSLTSSAGVLSCQP

GAPC

Dog
*Canis* Sequences:

Can f 1

(SEQ ID NO: 59)

MKTLLLTIGFSLIAILQAQDTPALGKDTVAVSGKWYLKAMTADQEVP

EKPDSVTPMILKAQKGGNLEAKITMLTNGQCQNITVVLHKTSEPGKY

TAYEGQRVVFIQPSPVRDHYILYCEGELHGRQIRMAKLLGRDPEQSQ

EALEDFREFSRAKGLNQEILELAQSETCSPGGQ

Serum albumin fragment (SEQ ID NO: 60)

EAYKSEIAHRYNDLGEEHFRGLVL

Serum albumin fragment (SEQ ID NO: 61)

LSSAKERFKCASLQKFGDRAFKAWSVARLSQRFPKADFAEISKVVT

DLTKVHKECCHGDLLECADDRADLAKYMCENQDSISTKLKECCDKP

VLEKSQCLAEVERDELPGDLPSLAADFVEDKEVCKNYQEAKDVFLG

TFLYEYSRRHPEYSVSLLLRLAKEYEATLEKCCATDDPPTCYAKVLDE

FKPLVDEPQNLVKTNCELFEKLGEYGFQNALLVRYTKKAPQVSTPTLV

VEVSRKLGKVGTKCCKKPESERMSCADDFLS

Can f2

(SEQ ID NO: 62)

MQLLLLTVGLALICGLQAQEGNHEEPQGGLEELSGRWHSVALASNKS

DLIKPWGHFRVFIHSMSAKDGNLHGDILIPQDGQCEKVSLTAFKTATSN

KFDLEYWGHNDLYLAEVDPKSYLILYMINQYNDDTSLVAHLMVRDLSRQ

QDFLPAFESVCEDIGLHKDQIVVLSDDDRCQGSRD

Additional dog allergen protein (NCBI entrez accession): 1731859

Horse

*Equus* Sequences:

1575778 Equ c1

(SEQ ID NO: 63)

MKLLLLCLGLILVCAQQEENSDVAIRNFDISKISGEWYSIFLASDVK

EKIEENGSMRVFVDVIRALDNSSLYAEYQTKVNGECTEFPMVFDK

TEEDGVYSLNYDGYNVFRISEFENDEHIILYLVNFDKDRPFQLFEFY

AREPDVSPEIKEEFVKIVQKRGIVKENIIDLTKIDRCFQLRGNGVAQA

3121755 Equ c 2

(SEQ ID NO: 64)

SQXPQSETDYSQLSGEWNTIYGAASNIXK

Euroglyphus (mite)

Euroglyphus Sequences:

Eur m 1 (variant)

(SEQ ID NO: 65)

TYACSINSVSLPSELDLRSLRTVTPIRMQGGCGSCWAFSGVASTESAYLA

YRNMSLDLAEQELVDCASQNGCHGDTIPRGIEYIQQNGVVQEHYYPYVAR

EQSCHRPNAQRYGLKNYCQISPPDSNKIRQALTQTHTAVAVIIGIKDLNA

FRHYDGRTIMQHDNGYQPNYHAVNIVGYGNTQGVDYWIVRNSWDTTWGDN

GYGYFAANINL

Eur m 1 (variant)

(SEQ ID NO: 66)

TYACSINSVSLPSELDLRSLRTVTPIRMQGGCGSCWAFSGVASTESAYLA

YRNMSLDLAEQELVDCASQNGCHGDTIPRGIEYIQQNGVVQEHYYPYVAR

EQSCHRPNAQRYGLKNYCQISPPDSNKIRQALTQTHTAVAVIIGIKDLNA

FRHYDGRTIMQHDNGYQPNYHAVNIVGYGNTQGVDYWIVRNSWDTTWGDN

GYGYFAANINL

Eur m 1 (variant)

(SEQ ID NO: 67)

ETNACSINGNAPAEIDLRQMRTVTPIRMQGGCGSCWAFSGVAATESAYLA

YRNQSLDLAEQELVDCASQHGCHGDTIPRGIEYIQHNGVVQESYYRYVAR

EQSCRRPNAQRFGISNYCQIYPPNANKIREALAQTHSAIAVIIGIKDLDA

FRHYDGRTIIQRDNGYQPNYHAVNIVGYSNAQGVDYWIVRNSWDTNWGDN

GYGYFAANIDL

Eur m 1 (variant)

(SEQ ID NO: 68)

ETSACRINSVNVPSELDLRSLRTVTPIRMQGGCGSCWAFSGVAATESAYL

AYRNTSLDLSEQELVDCASQHGCHGDTIPRGIEYIQQNGVVEERSYPYVA

REQQCRRPNSQHYGISNYCQIYPPDVKQIREALTQTHTAIAVIIGIKDLR

AFQHYDGRTIIQHDNGYQPNYHAVNIVGYGSTQGVDYWIVRNSWDTTWGD

SGYGYFQAGNNL

Cockroach Sequences

2833325 Cr p 1

(SEQ ID NO: 69)

MKTALVFAAVVAFVAARFPDHKDYKQLADKQFLAKQRDVLRLFHRVHQHN

ILNDQVEVGIPMTSKQTSATTVPPSGEAVHGVLQEGHARPRGEPFSVNYE

KHREQAIMLYDLLYFANDYDTFYKTACWARDRVNEGMFMYSFSIAVFHRD

DMQGVMLPPPYEVYPYLFVDHDVIHMAQKYWMKNAGSGEHHSHVIPVNFT

LRTQDHLLAYFTSDVNLNAFNTYYRYYYPSWYNTTLYGHNIDRRGEQFYY

TYKQIYARYFLERLSNDLPDVYPFYYSKPVKSAYNPNLRYHNGEEMPVRP

SNMYVTNFDLYYIADIKNYEKRVEDAIDFGYAFDEHMKPHSLYHDVHGME

YLADMIEGNMDSPNFYFYGSIYHMYHSMIGHIVDPYHKMGLAPSLEHPET

VLRDPVFYQLWKRVDHLFQKYKNRLPRYTHDELAFEGVKVENVDVGKLYT

YFEQYDMSLDMAVYVNNVDQISNVDVQLAVRLNHKPFTYNIEVSSDKAQD

VYVAVFLGPKYDYLGREYDLNDRRHYFVEMDRFPYHVGAGKTVIERNSHD

SNIIAPERDSYRTFYKKVQEAYEGKSQYYVDKGHNYCGYPENLLIPKGKK

GGQAYTFYVIVTPYVKQDEHDFEPYNYKAFSYCGVGSERKYPDNKPLGYP

FDRKIYSNDFYTYPNMYFKDVIIFHKKYDEVGVQGH

2231297 Cr p 2

(SEQ ID NO: 70)

INEIHSIIGLPPFVPPSRRHARRGVGINGLIDDVIAILPVDELKALFQEK

LETSPDFKALYDAIRSPEFQSIISTLNAMQRSEHHQNLRDKGVDVDHFIQ

LIRALFGLSRAARNLQDDLNDFLHSLEPISPRHRHGLPRQRRRSARVSAY

LHADDFHKIITTIEALPEFANFYNFLKEHGLDVVDYINEIHSIIGLPPFV

PPSRRHARRGVGINGLIDDVIAILPVDELKALFQEKLETSPDFKALYDAI

RSPEFQSIISTLNAMPEYQELLQNLRDKGVDVDHFIRVDQGTLRTLSSGQ

RNLQDDLNDFLALIPTDQILAIAMDYLANDAEVQELVAYLQSDDFHKIIT

TIEALPEFANFYNFLKEHGLDVVDYINEIHSIIGLPPFVPPSQRHARRGV

GINGLIDDVIAILPVDELKALFQEKLETSPDFKALYDAIDLRSSRA

-continued

```
1703445 Bla g 2
                                              (SEQ ID NO: 71)
MIGLKLVTVLFAVATITHAAELQRVPLYKLVHVFINTQYAGITKIGNQNF

LTVFDSTSCNVVVASQECVGGACVCPNLQKYEKLKPKYISDGNVQVKFFD

TGSAVGRGIEDSLTISNLTTSQQDIVLADELSQEVCILSADVVVGIAAPG

CPNALKGKTVLENFVEENLIAPVFSIHHARFQDGEHFGEIIFGGSDWKYV

DGEFTYVPLVGDDSWKFRLDGVKIGDTTVAPAGTQAIIDTSKAIIVGPKA

YVNPINEAIGCVVEKTTTRRICKLDCSKIPSLPDVTFVINGRNFNISSQY

YIQQNGNLCYSGFQPCGHSDHFFIGDFFVDHYYSEFNWENKTMGFGRSVE

SV

1705483 Bla g 4
                                              (SEQ ID NO: 72)
AVLALCATDTLANEDCFRHESLVPNLDYERFRGSWIIAAGTSEALTQYKC

WIDRFSYDDALVSKYTDSQGKNRTTIRGRTKFEGNKFTIDYNDKGKAFSA

PYSVLATDYENYAIVEGCPAAANGHVIYVQIRFSVRRFHPKLGDKEMIQH

YTLDQVNQHKKAIEEDLKHFNLKYEDLHSTCH

2326190 Bla g 5
                                              (SEQ ID NO: 73)
YKLTYCPVKALGEPIRFLLSYGEKDFEDYRFQEGDWPNLKPSMPFGKTPV

LEIDGKQTHQSVAISRYLGKQFGLSGKDDWENLEIDMIVDTISDFRAAIA

NYHYDADENSKQKKWDPLKKETIPYYTKKFDEVVKANGGYLAAGKLTWAD

FYFVAILDYLNHMAKEDLVANQPNLKALREKVLGLPAIKAWVAKRPPTDL
```

Additional cockroach sequences (NCBI Entrez accession numbers):

2580504; 1580797; 1580794; 1362590; 544619; 544618; 1531589; 1580792; 1166573; 1176397; 2897849.

Allergen (General) Sequences:

NCBI Accession Numbers

2739154; 3719257; 3703107; 3687326; 3643813; 3087805; 1864024; 1493836; 1480457; 2598976; 2598974; 1575778; 763532; 746485; 163827; 163823; 3080761; 163825; 3608493; 3581965; 2253610; 2231297; 2897849; 3409499; 3409498; 3409497; 3409496; 3409495; 3409494; 3409493; 3409492; 3409491; 3409490; 3409489; 3409488; 3409487; 3409486; 3409485; 3409484; 3409483; 3409482; 3409481; 3409480; 3409479; 3409478; 3409477; 3409476; 3409475; 3409474; 3409473; 3409472; 3409471; 3409470; 3409469; 3409468; 3409467; 3409466; 3409465; 3409464; 3409463; 3409462; 3409461; 3409460; 3409459; 3409458; 3409457; 3409456; 3318885; 3396070; 3367732; 1916805; 3337403; 2851457; 2851456; 1351295; 549187; 136467; 1173367; 2499810; 2498582; 2498581; 1346478; 1171009; 126608; 114091; 2506771; 1706660; 1169665; 1169531; 232086; 416898; 114922; 2497701; 1703232; 1703233; 1703233; 1703232; 3287877; 3122132; 3182907; 3121758; 3121756; 3121755; 3121746; 3121745; 3319925; 3319923; 3319921; 3319651; 3318789; 3318779; 3309647; 3309047; 3309045; 3309043; 3309041; 3309039; 3288200; 3288068; 2924494; 3256212; 3256210; 3243234; 3210053; 3210052; 3210051; 3210050; 3210049; 3210048; 3210047; 3210046; 3210045; 3210044; 3210043; 3210042; 3210041; 3210040; 3210039; 3210038; 3210037; 3210036; 3210035; 3210034; 3210033; 3210032; 3210031; 3210030; 3210029; 3210028; 3210027; 3210026; 3210025; 3210024; 3210023; 3210022; 3210021; 3210020; 3210019; 3210018; 3210017; 3210016; 3210015; 3210014; 3210013; 3210012; 3210011; 3210010; 3210009; 3210008; 3210007; 3210006; 3210005; 3210004; 3210003; 3210002; 3210001; 3210000; 3209999; 3201547; 2781152; 2392605; 2392604; 2781014; 1942360; 2554672; 2392209; 3114481; 3114480; 2981657; 3183706; 3152922; 3135503; 3135501; 3135499; 3135497; 2414158; 1321733; 1321731; 1321728; 1321726; 1321724; 1321722; 1321720; 1321718; 1321716; 1321714; 1321712; 3095075; 3062795; 3062793; 3062791; 2266625; 2266623; 2182106; 3044216; 2154736; 3021324; 3004467; 3005841; 3005839; 3004485; 3004473; 3004471; 3004469; 3004465; 2440053; 1805730; 2970629; 2959898; 2935527; 2935416; 809536; 730091; 585279; 584968; 2498195; 2833325; 2498604; 2498317; 2498299; 2493414; 2498586; 2498585; 2498576; 2497749; 2493446; 2493445; 1513216; 729944; 2498099; 548449; 465054; 465053; 465052; 548671; 548670; 548660; 548658; 548657; 2832430; 232084; 2500822; 2498118; 2498119; 2498119; 2498118; 1708296; 1708793; 416607; 416608; 416608; 416607; 2499791; 2498580; 2498579; 2498578; 2498577; 2497750; 1705483; 1703445; 1709542; 1709545; 1710589; 1352699; 1346568; 1346323; 1346322; 2507248; 11352240; 1352239; 1352237; 1352229; 1351935; 1350779; 1346806; 1346804; 1346803; 1170095; 1168701; 1352506; 1171011; 1171008; 1171005; 1171004; 1171002; 1171001; 1168710; 1168709; 1168708; 1168707; 1168706; 1168705; 1168704; 1168703; 1168702; 1168696; 1168391; 1168390; 1168348; 1173075; 1173074; 1173071; 1169290; 1168970; 1168402; 729764; 729320; 729979; 729970; 729315; 730050; 730049; 730048; 549194; 549193; 549192; 549191; 549190; 549189; 549188; 549185; 549184; 549183; 549182; 549181; 549180; 549179; 464471; 585290; 416731; 1169666; 113478; 113479; 113477; 113476; 113475; 130975; 119656; 113562; 113561; 113560; 416610; 126387; 126386; 126385; 132270; 416611; 416612; 416612; 416611; 730035; 127205; 1352238; 125887; 549186; 137395; 730036; 133174; 114090; 131112; 126949; 129293; 124757; 129501; 416636; 2801531; 2796177; 2796175; 2677826; 2735118; 2735116; 2735114; 2735112; 2735110; 2735108; 2735106; 2735104; 2735102; 2735100; 2735098; 2735096; 2707295; 2154730; 2154728; 1684720; 2580504; 2465137; 2465135; 2465133; 2465131; 2465129; 2465127; 2564228; 2564226; 2564224; 2564222; 2564220; 2051993; 1313972; 1313970; 1313968; 1313966; 2443824; 2488684; 2488683; 2488682; 2488681; 2488680; 2488679; 2488678; 2326190; 2464905; 2415702; 2415700; 2415698; 2398759; 2398757; 2353266; 2338288; 1167836; 414703; 2276458; 1684718; 2293571; 1580797; 1580794; 2245508; 2245060; 1261972; 2190552; 1881574; 511953; 1532058; 1532056; 1532054; 1359436; 666007; 487661; 217308; 1731859; 217306; 217304; 1545803; 1514943; 577696; 516728; 506858; 493634; 493632; 2154734; 2154732; 543659; 1086046; 1086045; 2147643; 2147642; 1086003; 1086002; 1086001; 543675; 543623; 543509; 543491; 1364099; 2147108; 2147107; 1364001; 1085628; 631913; 631912; 631911; 2147092; 477301; 543482; 345521; 542131; 542130; 542129; 100636; 2146809; 480443; 2114497; 2144915; 72355; 71728; 319828; 1082946; 1082945; 1082944; 539716; 539715; 423193; 423192; 423191; 423190; 1079187; 627190; 627189; 627188; 627187; 482382; 1362656; 627186; 627185; 627182; 482381; 85299; 85298; 2133756; 2133755; 1079186; 627181; 321044; 321043; 112559; 112558; 1362590; 2133564; 1085122; 1078971; 627144; 627143; 627142; 627141; 280576; 102835; 102834; 102833; 102832; 84703; 84702; 84700; 84699; 84698; 84696; 477888; 477505; 102575; 102572; 478272; 2130094; 629813; 629812; 542172; 542168; 542167; 481432; 320620; 280414; 626029; 542132; 320615; 320614; 100638; 100637; 100635; 82449; 320611; 320610; 280409; 320607; 320606;

539051; 539050; 539049; 539048; 322803; 280407; 100501; 100498; 100497; 100496; 1362137; 1362136; 1362135; 1362134; 1362133; 1362132; 1362131; 1362130; 1362129; 1362128; 100478; 2129891; 1076531; 1362049; 1076486; 2129817; 2129816; 2129815; 2129814; 2129813; 2129812; 2129805; 2129804; 2129802; 2129801; 2129800; 2129799; 479902; 479901; 2129477; 1076247; 629480; 1076242; 1076241; 541803; 541802; 280372; 280371; 1361968; 1361967; 1361966; 1361965; 1361964; 1361963; 1361962; 1361961; 1361960; 1361959; 320546; 2119763; 543622; 541804; 478825; 478824; 478823; 421788; 320545; 81444; 626037; 626028; 539056; 483123; 481398; 481397; 100733; 100732; 100639; 625532; 1083651; 322674; 322673; 81719; 81718; 2118430; 2118429; 2118428; 2118427; 419801; 419800; 419799; 419798; 282991; 100691; 322995; 322994; 101824; 626077; 414553; 398830; 1311457; 1916292; 1911819; 1911818; 1911659; 1911582; 467629; 467627; 467619; 467617; 915347; 1871507; 1322185; 1322183; 897645; 897647; 1850544; 1850542; 1850540; 288917; 452742; 1842045; 1839305; 1836011; 1836010; 1829900; 1829899; 1829898; 1829897; 1829896; 1829895; 1829894; 1825459; 1808987; 159653; 1773369; 1769849; 1769847; 608690; 1040877; 1040875; 1438761; 1311513; 1311512; 1311511; 1311510; 1311509; 1311689; 1246120; 1246119; 1246118; 1246117; 1246116; 1478293; 1478292; 1311642; 1174278; 1174276; 1086972; 1086974; 1086976; 1086978; 1086978; 1086976; 1086974; 1086972; 999009; 999356; 999355; 994866; 994865; 913758; 913757; 913756; 913285; 913283; 926885; 807138; 632782; 601807; 546852; 633938; 544619; 544618; 453094; 451275; 451274; 407610; 407609; 404371; 409328; 299551; 299550; 264742; 261407; 255657; 250902; 250525; 1613674; 1613673; 1613672; 1613671; 1613670; 1613304; 1613303; 1613302; 1613240; 1613239; 1613238; 1612181; 1612180; 1612179; 1612178; 1612177; 1612176; 1612175; 1612174; 1612173; 1612172; 1612171; 1612170; 1612169; 1612168; 1612167; 1612166; 1612165; 1612164; 1612163; 1612162; 1612161; 1612160; 1612159; 1612158; 1612157; 1612156; 1612155; 1612154; 1612153; 1612152; 1612151; 1612150; 1612149; 1612148; 1612147; 1612146; 1612145; 1612144; 1612143; 1612142; 1612141; 1612140; 1612139; 1093120; 447712; 447711; 447710; 1587177; 158542; 1582223; 1582222; 1531589; 1580792; 886215; 1545897; 1545895; 1545893; 1545891; 1545889; 1545887; 1545885; 1545883; 1545881; 1545879; 1545877; 1545875; 166486; 1498496; 1460058; 972513; 1009442; 1009440; 1009438; 1009436; 1009434; 7413; 1421808; 551228; 452606; 32905; 1377859; 1364213; 1364212; 395407; 22690; 22688; 22686; 22684; 488605; 17680; 1052817; 1008445; 1008443; 992612; 706811; 886683; 747852; 939932; 19003; 1247377; 1247375; 1247373; 862307; 312284; 999462; 999460; 999458; 587450; 763064; 886209; 1176397; 1173557; 902012; 997915; 997914; 997913; 997912; 997911; 997910; 99790; 997908; 997907; 997906; 997905; 997904; 997903; 997902; 997901; 997900; 997899; 997898; 997897; 997896; 997895; 997894; 997893; 997892; 910984; 910983; 910982; 910981; 511604; 169631; 169629; 169627; 168316; 168314; 607633; 555616; 293902; 485371; 455288; 166447; 166445; 166443; 166435; 162551; 160780; 552080; 156719; 156715; 515957; 515956; 515955; 515954; 515953; 459163; 166953; 386678; 169865.

It is to be understood that subsequent references to allergens, antigens or allergens are intended to encompass proteins of which the first peptide may be a fragment. It is also to be understood that all references to compositions encompass compositions comprising first polypeptide and one or more second polypeptide.

Particularly preferred first peptides for use in the methods of the invention have been identified in allergens from house dust mite and ragweed. Preferred peptides are fragments of the dust mite allergen Der p 1 or the Ragweed allergen Amb a 1 and are selected from the group consisting of:

(i) a peptide of the sequence of HDM03E, HDM202, HDM03W, or RGW07D; or (ii) a variant of a peptide according to (i), wherein said variant is a peptide of length 7 to 30 amino acids that comprises a region consisting of:

any of the sequences of (i), or a sequence which has at least 65% homology to any of the sequences of (i); or (iii) a variant of a peptide according to (i), wherein said variant is a peptide of length 7 to 30 amino acids that comprises a region consisting of a sequence that represents either:

a fragment of any of the sequences of (i), or a homologue of a fragment of any of the sequences of (i), wherein said homologue has at least 65% homology to any 7 contiguous amino acids in any of the sequences of (i).

It also envisaged that any of the sequences of (i) above may be modified to add at least one (and up to 6) residues at the N and/or C terminus, selected from R, K, H, E and D. Particularly preferred Der p 1 peptides include HDM03W.

The considerations regarding first peptides defined above apply to these peptides. Thus the above Der p 1 peptides may induce IL-10 release greater than whole allergen in 35, 40, 45, 50 or 55% of a population of dust mite allergic individuals, specifically Der p1 allergic individuals. The above Der p 1 peptides may induce an average IL-10 release greater than that induced by whole Der p 1 (or a variant thereof) in a dust mite allergic individual or population of dust mite allergic individuals. Whole Der p1 refers to the whole polypeptide sequence of Der p 1 or a truncated form comprising T cell epitopes required for allergic response.

Similarly, the above Amb a 1 peptide may induce IL-10 release greater than whole allergen in 35, 40, 45, 50 or 55% of a population of ragweed allergic individuals, specifically Amb a 1 allergic individuals. The above Amb a 1 peptide may induce an average IL-10 release greater than that induced by whole Amb a 1 (or a variant thereof) in a ragweed allergic individual or population of ragweed allergic individuals. Whole Amb a 1 refers to the whole polypeptide sequence of Amb a 1 or a truncated form comprising T cell epitopes required for allergic response.

As described above, a second polypeptide of the invention may be any peptide of 7 to 30 amino acids in length comprising at least one MHC Class II-binding T cell epitope which is a fragment of a protein allergen or a homologous variant of said fragment. Preferred second polypeptides of the invention include HDM03D, HDM03V, RGW07, RGW07B and RGW07C or variants thereof. Variants of second polypeptides of the invention include those as defined in relation to first polypeptides of the invention above.

As discussed above, more than one first and/or second polypeptide of the invention may be administered to an individual. Therefore, two, three, four or more of the above Der p 1 or Amb a 1 first and/or second polypeptides may be administered to an individual. The peptides may be administered sequentially, separately or in combination. For example, the peptides HDM03D and HDM202 may be administered to an individual, optionally in a sequential manner. An example of such an administration is shown in Example 4.

In connection with amino acid sequences described herein, "sequence identity" or "sequence homology" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10; Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

As described above, the first and second polypeptides of the invention are fragments of protein allergens or homologous variants of such fragments. The fragments are of 7 to 30 amino acids in length and preferably represent 10% or less of the protein allergen from which they are derived. Homologous variants of such fragments include peptides comprising a sequence which has at least 65% homology to any 7 contiguous amino acids in the protein allergen. Preferably, such homologous variants will comprise a sequence having at least 70%, 75%, 80%, 85%, 90%, 95% or more homology to any 7 contiguous amino acids in the protein allergen. In some embodiments the homologous variants will comprise a sequence that is identical to 7 contiguous amino acids in the protein allergen.

Additionally, the fragment or homologous variant thereof may represent a sequence of 8, 9, 10, 11, 12, 13, 14, 15 or more contiguous amino acids in the protein allergen. In such embodiments, a homologous variant may again comprise a sequence having at least 65%, preferably at least 70%, 75%, 80%, 85%, 90%, 95% or more to the stretch of contiguous amino acids in the protein allergen. Homologous variants of a fragment of a protein allergen may include variations such as additions, deletions, substitutions and modifications with respect to said fragment. Such variations are further described below.

Where specific peptide sequences are described herein, the invention also encompasses variants of such peptides.

A variant peptide may comprise 1, 2, 3, 4, 5 or more, or up to 10 amino acid substitutions from any of the specific peptide sequences described herein. Substitution variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| | | | |
|---|---|---|---|
| Ala | aliphatic, hydrophobic, neutral | Met | hydrophobic, neutral |
| Cys | polar, hydrophobic, neutral | Asn | polar, hydrophilic, neutral |
| Asp | polar, hydrophilic, charged (−) | Pro | hydrophobic, neutral |
| Glu | polar, hydrophilic, charged (−) | Gln | polar, hydrophilic, neutral |
| Phe | aromatic, hydrophobic, neutral | Arg | polar, hydrophilic, charged (+) |
| Gly | aliphatic, neutral | Ser | polar, hydrophilic, neutral |
| His | aromatic, polar, hydrophilic, charged (+) | Thr | polar, hydrophilic, neutral |
| Ile | aliphatic, hydrophobic, neutral | Val | aliphatic, hydrophobic, neutral |
| Lys | polar, hydrophilic, charged (+) | Trp | aromatic, hydrophobic, neutral |
| Leu | aliphatic, hydrophobic, neutral | Tyr | aromatic, polar, hydrophobic |

Further variants include those in which instead of the naturally occurring amino acid the amino acid which appears in the sequence is a structural analog thereof. Amino acids used in the sequences may also be modified, e.g. labelled, providing the function of the peptide is not significantly adversely affected.

Where the peptide has a sequence that varies from the sequences described herein, the substitutions may occur across the full length of the sequence, within the sequence of any of the sequences described herein or outside the sequence of any of the sequences described herein. For example, the variations described herein, such as additions, deletions, substitutions and modifications, may occur within the sequence of any of the sequences described herein. A variant peptide may comprise or consist essentially of the amino acid sequence of any of the sequences described herein in which one, two, three, four or more amino acid substitutions have been made. A variant peptide may comprise a fragment of the parent protein that is larger than any of the sequences described herein. In this embodiment, the variations described herein, such as substitutions and modifications, may occur within and/or outside the sequence of any of the sequences described herein. A preferred variant of SEQ ID NO: 10 is the peptide KKGEAAIKLTSSAGVLSK (SEQ ID NO: 74)

The variant peptides of the invention are 9 to 30 amino acids in length inclusive. Preferably, they may be from 9 to 20 or more preferably 13 to 17 amino acids in length. The peptides may be the same length as the peptide sequences described herein.

The peptides of the invention may be chemically derived from the polypeptide allergen, for example by proteolytic cleavage or can be derived in an intellectual sense from the polypeptide allergen, for example by making use of the amino acid sequence of the polypeptide allergen and synthesising peptides based on the sequence. Peptides may be synthesised using methods well known in the art.

Where polypeptides comprise residues which are typically difficult to preserve during manufacture, these residues may be replaced. For example, glutamate spontaneously forms pyroglutamate in solution particularly when present at the N or C terminus of a peptide. Thus, residues of the peptides of the invention which correspond to glutamate in the sequence of a native allergen protein sequence may be replaced with pyroglutamate in the peptides of the invention when such residues are present at the N or C terminus of a peptide.

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N-or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—NH2®-NH(Me) or —N(Me)2).

Analogues of peptides according to the invention may also include peptide variants that increase or decrease the peptide's half-life in vivo. Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

The peptides provided by the present invention may be derived from splice variants of the parent proteins encoded by mRNA generated by alternative splicing of the primary transcripts encoding the parent protein chains. The peptides may also be derived from amino acid mutants, glycosylation variants and other covalent derivatives of the parent proteins which retain at least an MHC-binding property of the allergens. Exemplary derivatives include molecules wherein the peptides of the invention are covalently modified by substitution, chemical, enzymatic, or other appropriate means with a moiety other than a naturally occurring amino acid. Further included are naturally occurring variants of the parent proteins found in different mites. Such a variant may be encoded by an allelic variant or represent an alternative splicing variant.

Variants as described above may be prepared during synthesis of the peptide or by post-production modification, or when the peptide is in recombinant form using the known techniques of site-directed mutagenesis, random mutagenesis, or enzymatic cleavage and/or ligation of nucleic acids.

Nucleic Acids and Vectors

The individual peptides of the invention may be administered directly, or may be administered indirectly by expression from an encoding sequence. When administered directly, the peptides described above may be formulated as compositions or products of the invention. Alternatively, a polynucleotide may be provided that encodes a peptide of the invention, such as any of the peptides described above. A peptide of the invention may thus be produced from or delivered in the form of a polynucleotide which encodes, and is capable of expressing, it. Any reference herein to the use, delivery or administration of a peptide of the invention is intended to include the indirect use, delivery or administration of such a peptide via expression from a polynucleotide that encodes it.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or purified form.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides of the invention can be synthesised according to methods well known in the art, as described by way of example in Sambrook et al (1989, Molecular Cloning—a laboratory manual; Cold Spring Harbor Press).

The polynucleotide molecules of the present invention may be provided in the form of an expression cassette which includes control sequences operably linked to the inserted sequence, thus allowing for expression of the peptide of the invention in vivo in a targeted subject. These expression cassettes, in turn, are typically provided within vectors (e.g., plasmids or recombinant viral vectors) which are suitable for use as reagents for nucleic acid immunization. Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a peptide of the invention.

The present invention thus includes expression vectors that comprise such polynucleotide sequences. Thus, the present invention provides a vector for use in preventing or treating a disorder by tolerisation. Furthermore, it will be appreciated that the invention may be carried out using a mixture of polypeptides and polynucleotides. Accordingly, the invention provides a composition or product wherein in place of any one of the polypeptides is a polynucleotide capable of expressing said polypeptide. Expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

Thus, a polypeptide of the invention may be provided by delivering such a vector to a cell and allowing transcription from the vector to occur. Preferably, a polynucleotide of the invention or for use in the invention in a vector is operably linked to a control sequence which is capable of providing for the expression of the coding sequence by the host cell, i.e. the vector is an expression vector.

"Operably linked" refers to an arrangement of elements wherein the components so described are configured so as to perform their usual function. Thus, a given regulatory sequence, such as a promoter, operably linked to a nucleic acid sequence is capable of effecting the expression of that sequence when the proper enzymes are present. The promoter need not be contiguous with the sequence, so long as it functions to direct the expression thereof. Thus, for example, intervening untranslated yet transcribed sequences can be present between the promoter sequence and the nucleic acid sequence and the promoter sequence can still be considered "operably linked" to the coding sequence.

A number of expression systems have been described in the art, each of which typically consists of a vector containing a gene or nucleotide sequence of interest operably linked to expression control sequences. These control sequences include transcriptional promoter sequences and transcriptional start and termination sequences. The vectors of the invention may be for example, plasmid, virus or phage vectors provided with an origin of replication, optionally a promoter for the expression of the said polynucleotide and optionally a regulator of the promoter. A "plasmid" is a vector in the form of an extrachromosomal genetic element. The vectors may contain one or more selectable marker genes, for example an ampicillin resistance gene in the case of a bacterial plasmid or a resistance gene for a fungal vector. Vectors may be used in vitro, for example for the production of DNA or RNA or used to transfect or transform a host cell, for example, a mammalian host cell. The vectors may also be adapted to be used in vivo, for example to allow in vivo expression of the polypeptide.

A "promoter" is a nucleotide sequence which initiates and regulates transcription of a polypeptide-encoding polynucleotide. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. It is intended that the term "promoter" or "control element" includes full-length promoter regions and functional (e.g., controls transcription or translation) segments of these regions.

A polynucleotide, expression cassette or vector according to the present invention may additionally comprise a signal peptide sequence. The signal peptide sequence is generally inserted in operable linkage with the promoter such that the signal peptide is expressed and facilitates secretion of a polypeptide encoded by coding sequence also in operable linkage with the promoter.

Typically a signal peptide sequence encodes a peptide of 10 to 30 amino acids for example 15 to 20 amino acids. Often the amino acids are predominantly hydrophobic. In a typical situation, a signal peptide targets a growing polypeptide chain bearing the signal peptide to the endoplasmic reticulum of the expressing cell. The signal peptide is cleaved off in the endoplasmic reticulum, allowing for secretion of the polypeptide via the Golgi apparatus. Thus, a peptide of the invention may be provided to an individual by expression from cells within the individual, and secretion from those cells.

Alternatively, polynucleotides of the invention may be expressed in a suitable manner to allow presentation of a peptide of the invention by an MHC class II molecule at the surface of an antigen presenting cell. For example, a polynucleotide, expression cassette or vector of the invention may be targeted to antigen presenting cells, or the expression of encoded peptide may be preferentially stimulated or induced in such cells.

Polynucleotides of interest may be used in vitro, ex vivo or in vivo in the production of a peptide of the invention. Such polynucleotides may be administered or used in the prevention or treatment of allergy by tolerisation.

Methods for gene delivery are known in the art. See, e.g., U.S. Pat. Nos. 5,399,346, 5,580,859 and 5,589,466. The nucleic acid molecule can be introduced directly into the recipient subject, such as by standard intramuscular or intradermal injection; transdermal particle delivery; inhalation; topically, or by oral, intranasal or mucosal modes of administration. The molecule alternatively can be introduced ex vivo into cells that have been removed from a subject. For example, a polynucleotide, expression cassette or vector of the invention may be introduced into APCs of an individual ex vivo. Cells containing the nucleic acid molecule of interest are re-introduced into the subject such that an immune response can be mounted against the peptide encoded by the nucleic acid molecule. The nucleic acid molecules used in such immunization are generally referred to herein as "nucleic acid vaccines."

The polypeptides, polynucleotides, vectors or cells of the invention may be present in a substantially isolated form. They may be mixed with carriers or diluents which will not interfere with their intended use and still be regarded as substantially isolated. They may also be in a substantially purified form, in which case they will generally comprise at least 90%, e.g. at least 95%, 98% or 99%, of the proteins, polynucleotides, cells or dry mass of the preparation.

Antigen Presenting Cells (APCs)

The invention encompasses the use in vitro of a method of producing a population of APCs that present the peptides of the invention on their surface, that may be subsequently used in therapy. Such a method may be carried out ex vivo on a sample of cells that have been obtained from a patient. The APCs produced in this way therefore form a pharmaceutical agent that can be used in the treatment or prevention of dust mite allergy by tolerisation. The cells should be accepted by the immune system of the individual because they derive from that individual. Delivery of cells that have been produced in this way to the individual from whom they were originally obtained, thus forms a therapeutic embodiment of the invention.

Formulations and Compositions

The peptides, polynucleotides, vectors and cells of the invention may be provided to an individual either singly or in combination. Each molecule or cell of the invention may be provided to an individual in an isolated, substantially isolated, purified or substantially purified form. For example, a peptide of the invention may be provided to an individual substantially free from the other peptides. Alternatively, four or more peptides in the composition may be coupled chemically together, using standard peptide coupling reagents, to provide a single peptide containing the preferred epitopes. Such peptides would be screened for basophil histamine release to confirm lack of histamine release as per the individual peptides. In a further embodiment, four or more peptides in the composition may be provided as part of a single polypeptide chain i.e by recombinant means from an encoding polynucleotide. The four or more peptides may be fused contiguously, or may alternatively be separated by appropriate linkers.

Whilst it may be possible for the peptides, polynucleotides or compositions according to the invention to be presented in raw form, it is preferable to present them as a pharmaceutical formulation. Thus, according to a further aspect of the invention, the present invention provides a pharmaceutical formulation for use in preventing or treating allergy to dust mites by tolerisation comprising a composition, vector or product according to the invention together with one or more pharmaceutically acceptable carriers or diluents and optionally one or more other therapeutic ingredients. The carrier (s) must be 'acceptable' in the sense of being compatible with the other ingredients of the formulation and not deleterious to the recipient thereof. Typically, carriers for injection, and the final formulation, are sterile and pyrogen free.

Formulation of a composition comprising the peptide, polynucleotides or cells of the invention can be carried out using standard pharmaceutical formulation chemistries and methodologies all of which are readily available to the reasonably skilled artisan.

For example, compositions containing one or more molecules or cells of the invention can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e.g., sterile pyrogen-free water) prior to parenteral administration of the reconstituted composition. The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono-or di-glycerides.

Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the peptides or polynucleotides of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulation of any of the peptides, polynucleotides or cells mentioned herein will depend upon factors such as the nature of the substance and the method of delivery. Any such substance may be administered in a variety of dosage forms. It may be administered orally (e.g. as tablets, troches, lozenges, aqueous or oily suspensions, dispersible powders or granules), topically, parenterally, subcutaneously, by inhalation, intravenously, intramuscularly, intrasternally, transdermally, intradermally, sublingually, instranasally, buccally or by infusion techniques. The substance may also be administered as suppositories. A physician will be able to determine the required route of administration for each particular individual.

The compositions of formulations of the invention will comprise a suitable concentration of each peptide/polynucleotide/cell to be effective without causing adverse reaction. Typically, the concentration of each peptide in the composition will be in the range of 0.03 to 200 nmol/ml. More preferably in the range of 0.3 to 200 nmol/ml, 3 to 180 nmol/ml, 10 to 150 nmol/ml or 30 to 120 nmol/ml. The composition or formulations should have a purity of greater than 95% or 98% or a purity of at least 99%.

In one embodiment, therefore, the peptides, polynucleotides, cells or compositions of the invention are used for therapy in combination with one or more other therapeutic agents. The agents may be administered separately, simultaneously or sequentially. They may be administered in the same or different compositions. Accordingly, in a method of the invention, the subject may also be treated with a further therapeutic agent.

A composition may therefore be formulated which comprises a molecule and/or cell of the invention and also one or more other therapeutic molecules. A composition of the invention may alternatively be used simultaneously, sequentially or separately with one or more other therapeutic compositions as part of a combined treatment.

Combination Immunotherapy

Since many subjects are allergic, or may require desensitizing to several polypeptide antigens, the current invention also provides means of desensitizing subjects that are allergic to multiple antigens. "Tolerance" induced in an individual to a first polypeptide can create in the subject a "tolerogenic environment" wherein inappropriate immune responses to other antigens can be downregulated in order to provide tolerance to other antigens.

This finding means that subjects allergic to multiple allergens can be treated in a greatly reduced time period, and that subjects seriously allergic to some allergens (e.g., peanuts) but more mildly allergic to other allergens (e.g., cat dander) can benefit from a therapy wherein tolerance to the milder allergen is established and then this tolerogenic environment is used to provide tolerance to the other, more extreme allergen.

A method is therefore provided for desensitising a subject to one or more further different second polypeptide antigens. The method entails, in a first step, administering to the individual peptides of the invention as described herein wherein the administration is carried out in a manner sufficient to generate a hyporesponsive state against the allergen of which the first peptide is a fragment or homologous variant thereof. Once a hyporesponsive state has been established toward said allergen, or at least a shift toward desensitisation has occurred, the method entails administration of a secondary composition comprising a second, different polypeptide antigen to which the subject is to be tolerised. Administration of the secondary composition is carried out in such a way as to take advantage of the tolerogenic environment established by peptides of the invention, where it is now possible to establish tolerance to the second, different polypeptide antigen.

The secondary composition is coadministered with either peptides of the invention or a larger fragment of the whole protein allergen(s) from which the peptides are derived. By "coadministered" it is meant either the simultaneous or concurrent administration, e.g., when the two are present in the same composition or administered in separate compositions at nearly the same time but at different sites, as well as the delivery of polypeptide antigens in separate compositions at different times. For example, the secondary composition may be delivered prior to or subsequent to delivery of peptides of the invention at the same or a different site. The timing between deliveries can range from about several seconds apart to about several minutes apart, several hours apart, or even several days apart. Furthermore, different delivery methods can be employed.

Delivery Methods

Once formulated the peptides and compositions of the invention can be delivered to a subject in vivo using a variety of known routes and techniques. For example, a composition can be provided as an injectable solution, suspension or emulsion and administered via parenteral, subcutaneous, epidermal, intradermal, intramuscular, intraarterial, intraperitoneal, intravenous injection using a conventional needle and syringe, or using a liquid jet injection system. Compositions can also be administered topically to skin or mucosal tissue, such as nasally, intratracheally, intestinal, rectally or vaginally, or provided as a finely divided spray suitable for respiratory or pulmonary administration. Other modes of administration include oral administration, suppositories, sublingual administration, and active or passive transdermal delivery techniques.

Where a peptide of the invention is to be administered, it is preferred to administer the peptide to a site in the body where it will have the ability to contact suitable antigen presenting cells, and where it, or they, will have the opportunity to contact T cells of the individual. Where an APC is to be administered, it is preferred to administer the APC to a site in the body where it will have the ability to contact, and activate, suitable T cells of the individual.

Delivery Regimes

Administration of the peptides/polynucleotides/cells (such as the composition containing a plurality of peptides) may be by any suitable method as described above. Suitable amounts of the peptide may be determined empirically, but typically are in the range given below. A single administration of each peptide may be sufficient to have a beneficial effect for the patient, but it will be appreciated that it may be beneficial if the peptide is administered more than once, in which case typical administration regimes may be, for example, once or twice a week for 2-4 weeks every 6 months, or once a day for a week every four to six months. As will be appreciated, each peptide or polynucleotide, or combination of peptides and/or polynucleotides may be administered to a patient singly or in combination.

Dosages for administration will depend upon a number of factors including the nature of the composition, the route of administration and the schedule and timing of the administration regime. Suitable doses of a molecule of the invention may be in the order of up to 15 μg, up to 20 μg, up to 25 μg, up to 30 μg, up to 50 μg, up to 100 μg, up to 500 μg or more per administration. Suitable doses may be less than 15 μg, but at least 1 ng, or at least 2 ng, or at least 5 ng, or at least 50 ng, or least 100 ng, or at least 500 ng, or at least 1 μg, or at least 10 μg. For some molecules of the invention, the dose used may be higher, for example, up to 1 mg, up to 2 mg, up to 3 mg, up to 4 mg, up to 5 mg or higher. Such doses may be provided in a liquid formulation, at a concentration suitable to allow an appropriate volume for administration by the selected route.

Kits

The invention also relates to a combination of components described herein suitable for use in a treatment of the invention which are packaged in the form of a kit in a container. Such kits may comprise a series of components to allow for a treatment of the invention. For example, a kit may comprise one or more different peptides, polynucleotides and/or cells of the invention, or one or more peptides, polynucleotides or cells of the invention and one or more additional therapeutic agents suitable for simultaneous administration, or for sequential or separate administration. The kit may optionally contain other suitable reagent(s) or instructions and the like.

Diagnostic Method

In a further aspect, the invention provides an in vitro method of determining whether an individual has or is at risk of a disorder susceptible to treatment with peptides of the invention, said method comprising the steps of:

i) incubating a first polypeptide according to the invention with T cells in a sample taken from the individual;
ii) measuring IL-10 release in said cells; and
iii) comparing the amount of IL-10 released to the amount released when T cells in a sample from the same individual are incubated with the whole protein allergen of which the first polypeptide is a fragment;

wherein the disorder is considered to be susceptible to said treatment if the first polypeptide induces the release of an amount of IL-10 that greater than the amount of IL-10 released in response to the whole protein allergen.

It should be understood that the first peptides of the invention are preferably suitable for tolerisation of a large proportion of the population, and can bind to a variety of MHC alleles. However, the above method provides for the tailored identification of first peptides for tolerisation of a specific individual.

Further Embodiments

The invention provides a first polypeptide of 7 to 30 amino acids in length which is a fragment of a protein or polypeptide antigen or a variant of said fragment; and which comprises at least one MHC Class II-binding T cell epitope, for use in a method of treating or preventing a disorder by tolerisation, wherein said first polypeptide induces the release of an amount of IL-10 that is greater than 50% of the IL-10 released in response to the whole protein or polypeptide antigen from which the first polypeptide derives; wherein the disorder is characterised by an inappropriate immune response to a protein or polypeptide antigen; and wherein optionally a second polypeptide derived from the protein or polypeptide antigen to which an inappropriate immune response is present is also administered. The invention also provides a composition comprising a first polypeptide of 7 to 30 amino acids in length and comprising at least one MHC Class II-binding T cell epitope for use in treating or preventing a disorder by tolerisation, wherein the disorder is characterised by an inappropriate immune response to a second polypeptide.

The first peptide may induce IL-10 release of greater than 60%, 80%, 100%, 120%, 150%, 200%, 300%, 400%, 500% or greater than the amount of IL-10 released in response to the whole protein or polypeptide.

In one embodiment said method comprises administration of the first polypeptide alone, and wherein the inappropriate immune response which characterises said disorder comprises an inappropriate immune response to one or more uncharacterised protein or polypeptide antigens.

The second polypeptide is typically of 7 to 30 amino acids in length, comprises at least one MHC Class II-binding T cell epitope; and is a fragment of said protein or polypeptide antigen or a homologous variant of said fragment.

The first and/or said second polypeptide may represent less than 10% of the whole protein or polypeptide antigen from which they derive, for example less than 8%, 6%, 4% or 2% of the whole protein or polypeptide.

The said first polypeptide and said second polypeptide may derived from the same protein or polypeptide antigen. However in one embodiment said first polypeptide and said second polypeptide are derived from different protein or polypeptide antigens. The first and second polypeptides typically have less than 40% homology with each other.

The disorder may be an allergic disease, an autoimmune disease, an alloimmun response, a maternal-foetal immune response, an immune response to a neoantigen or to a protein which is being provided to an individual in therapy.

The said protein or polypeptide antigen to which an inappropriate immune response is present is typically a protein allergen or auto-antigen; and/or said protein or polypeptide antigen from which said first and/or said second polypeptide are derived is a protein allergen or auto-antigen. In one embodiment said protein or polypeptide antigen to which an inappropriate immune response is present and/or said protein or polypeptide antigen from which said first and/or said second polypeptides derive is selected from i) an allergen selected from: a plant allergen (particularly a grass allergen), animal dander allergens, a mold or fungal allergen, a dust allergen, an antibiotic or other drug, a stinging insect venom, an environmental allergen or a food allergen; or ii) an antigen selected from the major antigens associated with Acute disseminated encephalomyelitis (ADEM); Addison's disease; Ankylosing spondylitis; Antiphospholipid antibody syndrome (APS); Aplastic anemia; Autoimmune hepatitis; Autoimmune Oophoritis; Coeliac disease; Crohn's disease; Diabetes mellitus type 1; Gestational pemphigoid; Goodpasture's syndrome; Graves' disease; Guillain-Barré syndrome (GBS); Hashimoto's disease; Idiopathic thrombocytopenic purpura; Kawasaki's Disease; Lupus erythematosus; Multiple sclerosis; Myasthenia gravis; Opsoclonus myoclonus syndrome (OMS); Optic neuritis; Ord's thyroiditis; Pemphigus; Pernicious anaemia; Polyarthritis in dogs; Primary biliary cirrhosis; Rheumatoid arthritis; Reiter's syndrome; Sjögren's syndrome; Takayasu's arteritis; Temporal arteritis (also known as "giant cell arteritis"); Warm autoimmune hemolytic anemia; or Wegener's granulomatosis.

The said protein or polypeptide antigen to which an inappropriate immune response is present and/or said protein or polypeptide antigen from which said first and/or said second polypeptides derive may be selected from: cat dander protein Fel d1; House dust mite proteins Der p 1, Der p 2 and Der p 7; Ragweed protein amb a 1.1, a 1.2, a1.3 or a1.4; Rye grass proteins Lol p 1 and Lol p 5; Timothy grass proteins phl p 1 and phl p 5; Bermuda grass protein Cyn d 1; Alternaria alternata proteins Alt a 1, Alt a 2, Enolase (Alt a 6), Alt a 10, Alt a 13; Cladosporium herbarum proteins Cla h 6, Cla h 8; Birch protein Bet v1, Bet v 3, Bet v 4, Bet v 6 and P14; German Cockroach proteins Bla g 1, Bla g 2, Bla g 3, Bla g 4, Bla g 5 and Bla g 6; Mugwort protein Art v 1; Russian thistle protein Sal k 1 and Sal k 2; peanut Ara h 1, Ara h 2, Ara h 3, Ara h 4, Ara h 5, Ara h 6, plant profilins or lipid transfer proteins or a human leukocyte antigen.

Said first polypeptide imay be administered sequentially, separately or in combination with the second polypeptide.

The first polypeptide may be a fragment of the house dust mite protein Der p 1 or the ragweed protein Amb a 1 or the grass proteins Cyn d 1, Lol p 5, Phl p 1, and Phl p 5 or a homologous variant of said fragment. In one embodiment the first polypeptide is:

(i) a peptide of the sequence of HDM03D, HDM03E, HDM202, HDM03V, HDM03W, RGW07, RGW07B, RGW07C, RGW07D, Bio02A, Bio04A, Bio04B, Bio05B, Tim04A, Tim07B, Rye08A, Ber01, Ber02D, Ber02E, or Ber03A; or (ii) a variant of a peptide according to (i), wherein said variant is a peptide of length 7 to 30 amino acids that comprises a region consisting of:

any of the sequences of (i), or a sequence which has at least 65% homology to any of the sequences of (i); or (iii) a variant of a peptide according to (i), wherein said variant is a peptide of length 7 to 30 amino acids that comprises a region consisting of a sequence that represents either:

a fragment of any of the sequences of (i), or a homologue of a fragment of any of the sequences of (i), wherein said homologue has at least 65% homology to any 7 contiguous amino acids in any of the sequences of (i).

In one embodiment the first and/or said second polypeptide do not comprise an epitope capable of cross-linking IgG expressed on the cell surface of B cells or IgE expressed on the surface of mast cells or basophils and/or wherein the T cell epitope is the minimal MHC Class II-binding sequence of a T cell epitope derived from the protein or polypeptide antigen.

The first and/or said second polypeptide may have one or more modifications selected from the following:

(i) N terminal acetylation;

(ii) C terminal amidation;

(iii) one or more hydrogen on the side chain amines of Arginine and/or Lysine replaced with a methylene group;

(iv) glycosylation; and (v) phosphorylation.

The first and/or said second polypeptide may have been engineered to be soluble such that they comprise:

i) N terminal to the residues of the peptide which flank a T cell epitope: one to six contiguous amino acids corresponding to the two to six contiguous amino acids immediately N terminal to said residues in the sequence of the protein from which the peptide derives; and/or ii) C terminal to the residues of the peptide which flank a T cell epitope: one to six contiguous amino acids corresponding to the one to six contiguous amino acids immediately C terminal to the said residues in the sequence of the protein from which the peptide derives; or iii) both N and C terminal to the residues of the peptide which flank a T cell epitope, at least one amino acid selected from arginine, lysine, histidine, glutamate and aspartate, wherein the polypeptide has a solubility of at least 3.5 mg/ml and the T cell epitope has a solubility of less than 3.5 mg/ml.

The first and/or said second polypeptide may have been engineered to be soluble such that:

i) any cysteine residues in the native sequence of the peptide are replaced with serine or 2-aminobutyric acid; and/or ii) any hydrophobic residues in the up to three amino acids at the N or C terminus of the native sequence of the peptide, which are not comprised in a T cell epitope, are deleted; and/or iii) any two consecutive amino acids comprising the sequence Asp-Gly in the up to four amino acids at the N or C terminus of the native sequence of the peptide, which are not comprised in a T cell epitope, are deleted.

The first polypeptide and/or said second polypeptide are typically each present at a concentration in the range of 0.03 to 200 nmol/ml, 0.3 to 200 nmol/ml or 30 to 120 nmol/ml in the composition which is administered.

The first polypeptide may be defined with reference to another peptide (instead of by any of the other definitions used here that are based on amounts of IL-10 release versus whole polypeptide). In one embodiment the first polypeptide causes release of at least as much IL-10 as does peptide HDM202. This may be measured by using any suitable assay, such as the one described in Example 3.

The invention is illustrated by the following Examples:

Example 1

| Peptide | Parent molecule | Sequence | Residues in parent | SEQ ID NO: |
|---|---|---|---|---|
| HDM01 | Der p 1 | IDLRQMRTVTPIR | 112-124 | 75 |
| HDM01A | Der p 1 | IDLRQMRTVTPIRMQGGSG | 112-130 | 76 |
| HDM02A | Der p 1 | RTVTPIRMQGG**S**G | 118-130 | 77 |
| HDM02B | Der p 1 | RTVTPIRMQGGБ G | 118-130 | 78 |
| HDM03D | Der p 1 | RNQSLDLAEQELVD**S**ASQH | 149-167 | 1 |
| HDM03E | Der p 1 | RNQSLDLAEQELVDБ ASQH | 149-167 | 2 |
| HDM03F | Der p 1 | RNQSLDLAEQELVD**S**AS | 149-165 | 79 |
| HDM03G | Der p 1 | QSLDLAEQELVDБ ASQHG | 151-168 | 80 |
| HDM03H | Der p 1 | LDLAEQELVDБ ASQHG | 153-168 | 81 |
| HDM03J | Der p 1 | LAEQELVDБ ASQHG | 155-168 | 82 |
| HDM03K | Der p 1 | EQELVDБ ASQHG | 157-168 | 83 |
| HDM03L | Der p 1 | ELVDБ ASQHG | 159-168 | 84 |
| HDM03M | Der p 1 | RNQSLDLAEQELVDCASQHG | 149-168 | 85 |
| HDM03N | Der p 1 | RNQSLDLAEQELVDĈASQHG | 149-168 | 86 |
| HDM03P | Der p 1 | SAYLAHRNQSLDLAEQELVDCAS | 143-166 | 87 |
| HDM03R | Der p 1 | QSLDLAEQELVD**S**ASQHG | 151-168 | 88 |
| HDM03S | Der p 1 | LDLAEQELVD**S**ASQHG | 153-168 | 89 |
| HDM03T | Der p 1 | LAEQELVD**S**ASQHG | 155-168 | 90 |
| HDM03V | Der p 1 | EQELVDSASQHG | 157-168 | 3 |

-continued

| Peptide | Parent molecule | Sequence | Residues in parent | SEQ ID NO: |
|---|---|---|---|---|
| HDM03W | Der p 1 | ELVD**S**ASQHG | 159-168 | 4 |
| HDM06A | Der p 1 | RYVAREQS**S**RRP | 193-205 | 91 |
| HDM06B | Der p 1 | RYVAREQSБ RRP | 193-205 | 92 |
| HDM07 | Der p 1 | PNVNKIREALAQT | 220-232 | 93 |
| HDM09A | Der p 1 | REALAQTHSAIAVI | 226-239 | 94 |
| HDM19A | Der p 2 | DQVDVKD**S**ANHEIKK | 18-32 | 95 |
| HDM19B | Der p 2 | DQVDVKDБ ANHEIKK | 18-32 | 96 |
| HDM20A | Der p 2 | IIHRGKPFQLEA | 45-56 | 97 |
| HDM20B | Der p 2 | **S**IIHRGKPFQLEA | 44-56 | 98 |
| HDM21 | Der p 2 | KPFQLEAVFEANQNT | 50-64 | 99 |
| HDM21A | Der p 2 | KPFQLEAVFEANQNTK | 50-65 | 100 |
| HDM21B | Der p 2 | RGKPFQLEAVFEANQNT | 48-64 | 101 |
| HDM22A | Der p 2 | EAVFEANQNTKTAK | 55-68 | 102 |
| HDM23B | Der p 2 | GLEVDVPGIDPNA | 77-86 | 103 |
| HDM23C | Der p 2 | GLEVDVPGIDPNA**S**H | 77-88 | 104 |
| HDM26B | Der p 2 | GVLA**S**AIATHAKIR | 132-145 | 105 |
| HDM26C | Der p 2 | GVLAБ AIATHAKIR | 132-145 | 106 |
| HDM30 | Der p 7 | DKFERHIGIIDLK | 56-68 | 107 |
| HDM32 | Der p 7 | IDLKGELDMRNIQ | 65-77 | 108 |
| HDM33 | Der p 7 | LDMRNIQVRGLKQ | 71-83 | 109 |
| HDM34 | Der p 7 | RNIQVRGLKQMKRVG | 74-88 | 110 |
| HDM35A | Der p 7 | RGLKQMKRVGDANV | 79-80 | 111 |
| HDM39A | Der p 7 | HDDVVSMEYDLAYKL | 108-121 | 112 |
| HDM39B | Der p 7 | HDDVVSMEYDLAYKLGDLH | 108-125 | 113 |
| HDM40A | Der p 7 | VSMEYDLAYKLGDLH | 112-124 | 114 |
| HDM40B | Der p 7 | VSMEYDLAYKLGDL | 112-123 | 115 |
| HDM48 | Der p 7 | TAIFQDTVRAEMTK | 187-200 | 116 |
| HDM48A | Der p 7 | TAIFQDTVRAEMTKVLAP | 187-204 | 117 |
| HDM49 | Der p 7 | DTVRAEMTKVLAP | 192-204 | 118 |
| HDM51 | Der p 7 | VDFKGELAMRNIE | 65-77 | 119 |
| HDM51A | Der p 7 | VDFKGELAMRNIEAR | 65-79 | 120 |
| HDM100 | Der p 1 | RFGISNYCQIYPPNVNK | 208-224 | 121 |
| HDM100A | Der p 1 | RFGISNY**S**QIYPPNVNK | 208-224 | 122 |
| HDM100B | Der p 1 | RFGISNYБ QIYPPNVNK | 208-224 | 123 |
| HDM101 | Der p 1 | NYCQIYPPNVNKIREA | 213-228 | 124 |
| HDM101A | Der p 1 | NY**S**QIYPPNVNKIREA | 213-228 | 125 |
| HDM101B | Der p 1 | NYБ QIYPPNVNKIREA | 213-228 | 126 |

-continued

| Peptide | Parent molecule | Sequence | Residues in parent | SEQ ID NO: |
|---|---|---|---|---|
| HDM102 | Der p 1 | NAQRFGISNYCQI | 205-217 | 127 |
| HDM102A | Der p 1 | NAQRFGISNYSQI | 205-217 | 128 |
| HDM102B | Der p 1 | NAQRFGISNYБQI | 205-217 | 129 |
| HDM103 | Der p 2 | KGQQYDIKYTWNVPKIAP | 99-116 | 130 |
| HDM104 | Der p 2 | WNVPKIAPKSENV | 109-121 | 131 |
| HDM201 | Der p 1 | ESVKYVQSNGGAI | 52-64 | 132 |
| HDM202 | Der p 1 | DEFKNRFLMSAEAFE | 73-87 | 5 |
| HDM202D | Der p 1 | FKNRFLMSAEA | 75-85 | 133 |
| HDM202E | Der p 1 | FKNRFLMSAE | 75-84 | 134 |
| HDM202H | Der p 1 | EFKNRFLMSAE | 74-84 | 135 |
| HDM203A | Der p 1 | DLRQMRTVTPIRMQGGCGS | 113-131 | 136 |
| HDM203B | Der p 1 | DLRQMRTVTPIRMQGGSGS | 113-131 | 137 |
| HDM204 | Der p 1 | SAYLAYRNQSLDLA | 143-156 | 138 |
| HDM205 | Der p 1 | SYYRYVAREQS | 190-199 | 139 |
| HDM206 | Der p 1 | DNGYGYFAANIDLMMIEE | 296-313 | 140 |
| HDM206A | Der p 1 | NGYGYFAANIDLMM | 297-310 | 141 |
| HDM207 | Der p 7 | DMRNIQVRGLKQMKRVGD | 72-89 | 142 |

Б = 2-aminobutryic acid

Residues in bold in the above Table indicate alterations from the corresponding residue in the native sequence of the parent protein. These alterations reduce the formation of peptide dimers and improve solubility without diminishing the functionality of a peptide as a T cell epitope. The alterations shown are the replacement of a cysteine (C) in the native sequence with a serine (S) or 5-aminobutyric acid (Б), or cystine (Ĉ) as indicated. The "residues in parent" positions in the Table refer to the sequences of Der p 1, Der p 2 and Der p 7 as published in the NCBI database (NCBI accession nos: P08176, P49278 and P49273 respectively).

Those peptides indicated above which have an N terminal glutamate (E) or glutamine (Q) residue, for example HDM03K, L, V and W, may have this residue replaced with pyroglutamate to improve stability during manufacture, without affecting function of the peptide. The data from further testing of these peptides (Example 2) is typically obtained using peptides where such replacement has taken place.

Example 2

Ragweed

The peptides described below were identified by analysis of Amb a 1 to determine regions of the protein which comprise T cell epitopes. The following regions of interest were identified:

| REGION OF INTEREST | RESIDUES IN AMB A 1 | SEQUENCE |
|---|---|---|
| A | 178-189 | GMIKSNDGPPIL (SEQ ID NO: 143) |
| B | 202-213 | GSSQIWIDHCSL (SEQ ID NO: 144) |
| B | 205-216 | QIWIDHCSLSKS (SEQ ID NO: 145) |
| C | 343-354 | DKDLLENGAIFV (SEQ ID NO: 146) |
| C | 346-357 | LLENGAIFVTSG (SEQ ID NO: 147) |
| C | 349-360 | NGAIFVTSGSDP (SEQ ID NO: 148) |
| C | 352-363 | IFVTSGSDPVLT (SEQ ID NO: 149) |
| C | 355-366 | TSGSDPVLTPVQ (SEQ ID NO: 150) |
| D | 364-375 | PVQSAGMIPAEP (SEQ ID NO: 151) |
| D | 367-378 | SAGMIPAEPGEA (SEQ ID NO: 152) |
| E | 103-114 | EGTLRFAAAQNR (SEQ ID NO: 153) |
| E | 106-117 | LRFAAAQNRPLW (SEQ ID NO: 154) |
| F | 130-141 | QELVVNSDKTID (SEQ ID NO: 155) |
| F | 133-144 | VVNSDKTIDGRG (SEQ ID NO: 156) |
| F | 136-147 | SDKTIDGRGVKV (SEQ ID NO: 157) |
| F | 139-150 | TIDGRGVKVEII (SEQ ID NO: 158) |
| G | 376-387 | GEAAIKLTSSAG (SEQ ID NO: 159) |
| G | 379-390 | AIKLTSSAGVLS (SEQ ID NO: 160) |
| G | 382-393 | LTSSAGVLSCRP (SEQ ID NO: 161) |
| H | 226-237 | GSTHVTISNCKF (SEQ ID NO: 162) |
| I | 280-297 | HGFFQVVNNNYDRGTYA (SEQ ID NO: 163) |
| J | 38-48 | ETRRLTTSGAYN (SEQ ID NO: 164) |

These regions were then further analysed to find which of them were highly conserved between the 4 different Amb a1 isoforms as shown below (1.1, 1.2, 1.3 and 1.4). For the below sequences, the following text styles are used to indicate regions of interest: Region A, Region B, Region C, Region D, Region E, Region F, Region G, Region H, Region I, Region J Amb 1.1

(SEQ ID NO: 165)

MGIKHCCYILYFTLALVTLLQPVRSAEDLQEILPVNETRRLTTSGAYNII
DGCWRGKADWAENRKALADCAQGFGKGTVGGKDGDIYTVTSELDDDVANP
KEGTLRFGAAQNRPLWIIFERDMVIRLDKEMVVNSDKTID
GRGAKVEIINAGFTLNGVKNVIIHNINMHDVKVNPGGLIKSNDGPAAPR
AGSDGDAISISGSSQIWIDHC
SLSKSVDGLVDAKLGTTRLTVSNSLFTQHQFVLLFGAGDENIEDRG
MLATVAFNTFTDNVDQRMPRCR
HGFFQVVNNNYDKWGSYAIGGSASPTILSQGNRFCAPDERSKKNVLGRHG
EAAAESMKWNWRTNKDVLENGA
IFVASGVDPVLTPEQSAGMIPAEPGESALSLTSSAGVLSCQPGAPC

Amb 1.2

(SEQ ID NO: 166)

MGIKHCCYILYFTLALVTLLQPVRSAEDVEEFLPSANETRRSLKACEAHN
IIDKCWRCKADWANNRQALA
DCAQGFAKGTYGGKHGDVYTVTSDKDDDVANPKEGTLRFAAAQNRPLWI
IFKRNMVIHLNQELVVNSDKT
IDGRGVKVNIVNAGLTLMNVKNIIIHNINIHDIKVCPGGMIKSNDPPIL
RQQSDGDAINVAGSSQIWID
HCSLSKASDGLLDITLGSSHVTVSNCKFTQHQFVLLLGADDTHYQDKG
MLATVAFNMFTDNVDQRMPRCR
FGFFQVVNNNYDRWGTYAIGGSAPTILSQGNRFFAPDDIIKKNVLARTG
TGNAESMSWNWRTDRDLLEN
GAIFLPSGSDPVLTPEQKAGMIPAEPGEAVLRLTSSAGVLSCHQGAPC

Amb 1.3

(SEQ ID NO: 167)

MGIKQCCYILYFTLALVALLQPVRSAEGVGEILPSVNETRSLQACEALN
IIDKCWRGKADWENNRQALAD
CAQGFAKGTYGGKWGDVYTVTSNLDDDVANPKEGTLRFAAAQNRPLWII
FKNDMVINLNQELVVNSDKTI
DGRGVKVEIINGGLTLMNVKNIIIHNINIHDVKVLPGGMIKSNDGPPIL
RQASDGDTINVAGSSQIWIDH
CSLSKSFDGLVDVTLGSTHVTISNCKFTQQSKAILLGADDTHVQDKGMLA
TVAFNMFTDNVDQRMPRCRFGFFQVVNNNYDRWGTYAIGGSAPTILCQGN
RFLAPDDQIKKNVLARTGTGAAESMAWNWRSDKDLLENG
AIFVTSGSDPVLTPVQSAGMIPAEPGEAAIKLTSSAGVFSCHPGAPC

Amb 1.4

(SEQ ID NO: 168)

MGIKHCCYILYFTLALVTLLQPVRSAEDLQQILPSANETRSLTTCGTYN
IIDGCWRGKADWAENRKALAD
CAQGFAKGTIGGKDGDIYTVTSELDDDVANPKEGTLRFGAAQNRPLWI
IFARDMVIRLDRELAINNDKTI
DGRGAKVEIINAGFAIYNVKNIIIHNIIMHDIVVNPGGLIKSHDGPPVP
RKGSDGDAIGISGSSQIWIDH
CSLSKAVDGLIDAKHGSTHFTVSNCLFTQHQYLLLFWDFDERGMLCTVA
FNKFTDNVDQRMPNLRHGFVQVVNNNYERWGSYALGGSAGPTILSQGNR
FLASDIKKEVVGRYGESAMSESINWNWRSYMDVFEGAIFVPSGVDPV
LTPEQNAGMIPAEPGEAVLRLTSSAGVLSCQPGAPC

The following peptides were considered to be highly conserved and therefore taken forward for further testing:

| Peptide | Region of interest | Sequence | SEQ ID NO: |
|---|---|---|---|
| RGW01 | A | GMIKSNDGPPI | 169 |
| RGW01A | A | GLIKSHDGPPV | 170 |
| RGW01B | A | GLIKSNDGPAA | 171 |
| RGW02 | B | GSSQIWIDHSSLSKS | 172 |
| RGW02A | B | GSSQIWIDHCSLSKS | 173 |
| RGW02B | B | GGSQIWIDHCSLSKA | 174 |
| RGW03 | C | KDLLENGAIFVTSG | 175 |
| RGW03A | C | DVFENGAIFVPSG | 176 |
| RGW03B | C | RDLLENGAIFLPSG | 177 |
| RGW04 | D | KAGMIPAEPGEA | 178 |
| RGW4A | D | SAGMIPAEPGEA | 179 |
| RGW05 | E | KEGTLRFAAAQNRP | 180 |
| RGW05A | E | KEGTLRFGAAQNRP | 181 |
| RGW06 | F | VVNSDKTIDGRGVKVE | 182 |
| RGW06A | F | AINNDKTIDGRGAKVE | 183 |
| RGW07 | G | GEAAIKLTSSAGVLS | 6 |
| RGW07A | G | GEAVLRLTSSAGVLS | 7 |
| RGW07B | G | GESALSLTSSAGVLS | 8 |
| RGW07C | G | KGEAAIKLTSSAGVLSK | 9 |
| RGW07D | G | KGEAAIKLTSSAGVLSKK | 10 |
| RGW08 | H | GSTHVTISNSKF | 184 |
| RGW08A | H | GSTHVTISNCKF | 185 |
| RGW08B | H | GSTHFTVSNCLF | 186 |
| RGW08C | H | GSTHFTVSNSLF | 187 |
| RGW08D | H | GTTRLTVSNSLF | 188 |
| RGW09 | J | ETRRSLKTSGAYN | 189 |
| RGW10 | I | FGFFQVVNNNYD | 190 |
| RGW10A | I | HGFFQVVNNNYD | 191 |
| RGW11 | I | VNNNYDRWGTYA | 192 |
| RGW11A | I | VNNNYDKWGSYA | 193 |
| RGW11B | I | VNNNYERWGSYA | 194 |

Example 3

Cytokine Release Assay

Cytokine secretion profiles from PBMC's are analysed in response to the peptide stimulation using the peptides from Examples 1 and 2. Supernatants from the cytokine release assay were tested for the presence of IL-10, using either an ELISA assay or a multiplex bead array assay. A typical cytokine release assay requires $40\times10^6$ PBMC's per subject. In more detail, 250 μl of a 200 μg/ml solution of the appropriate antigen or peptide concentration is distributed into the appropriate wells of 48 well plates. Plates are then incubated in a humidified 5% CO2 incubator at 37° C. for a maximum of 4 hours. 250 μl of a $5\times10^6$ cell/ml PBMC suspension is then added to each well and the plates returned to the incubator for 5 days. Following stimulation, samples of culture supernatant are harvested for testing by ELISA or multiplex bead assay according to standard protocols.

Figure 2:
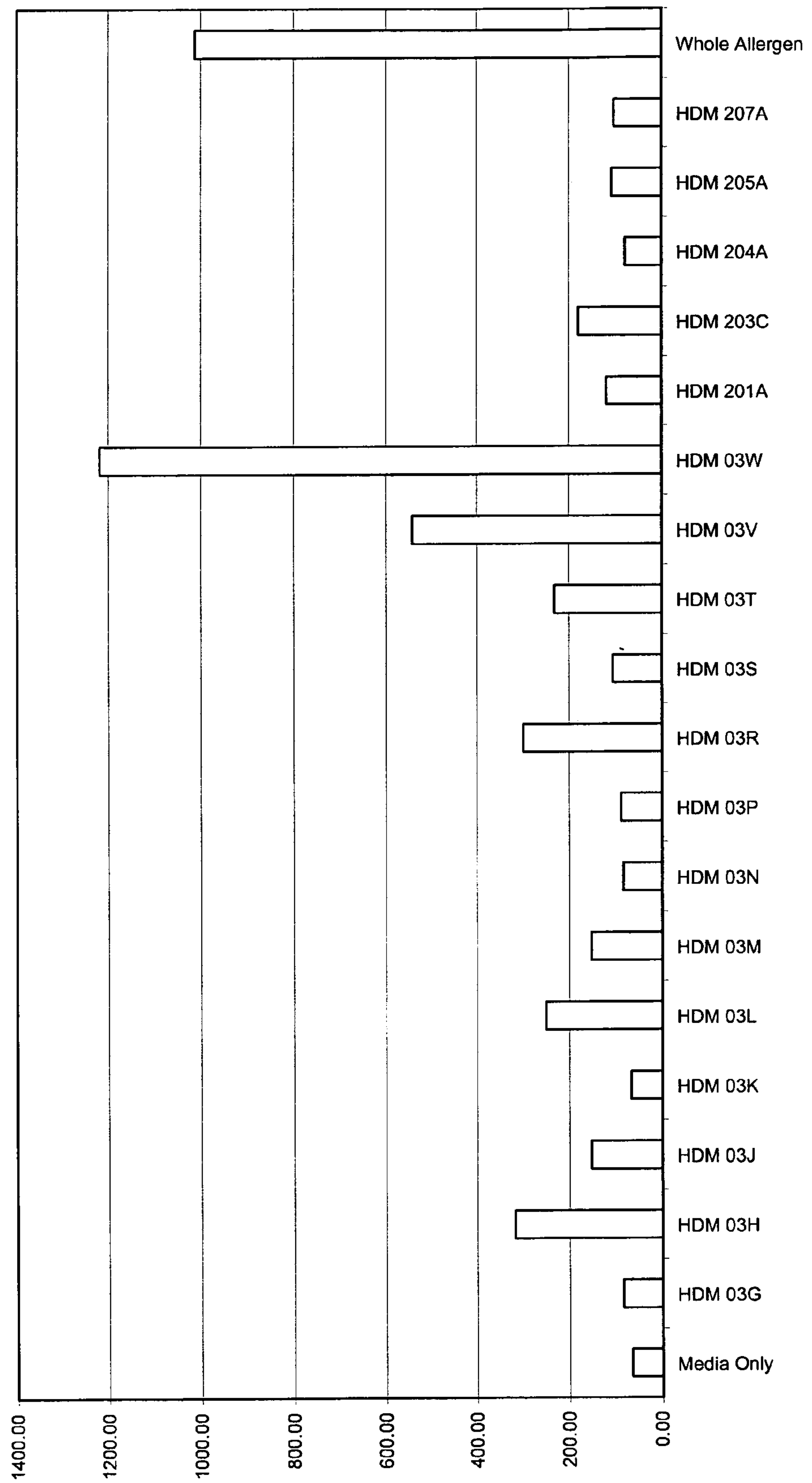
Figure 3:
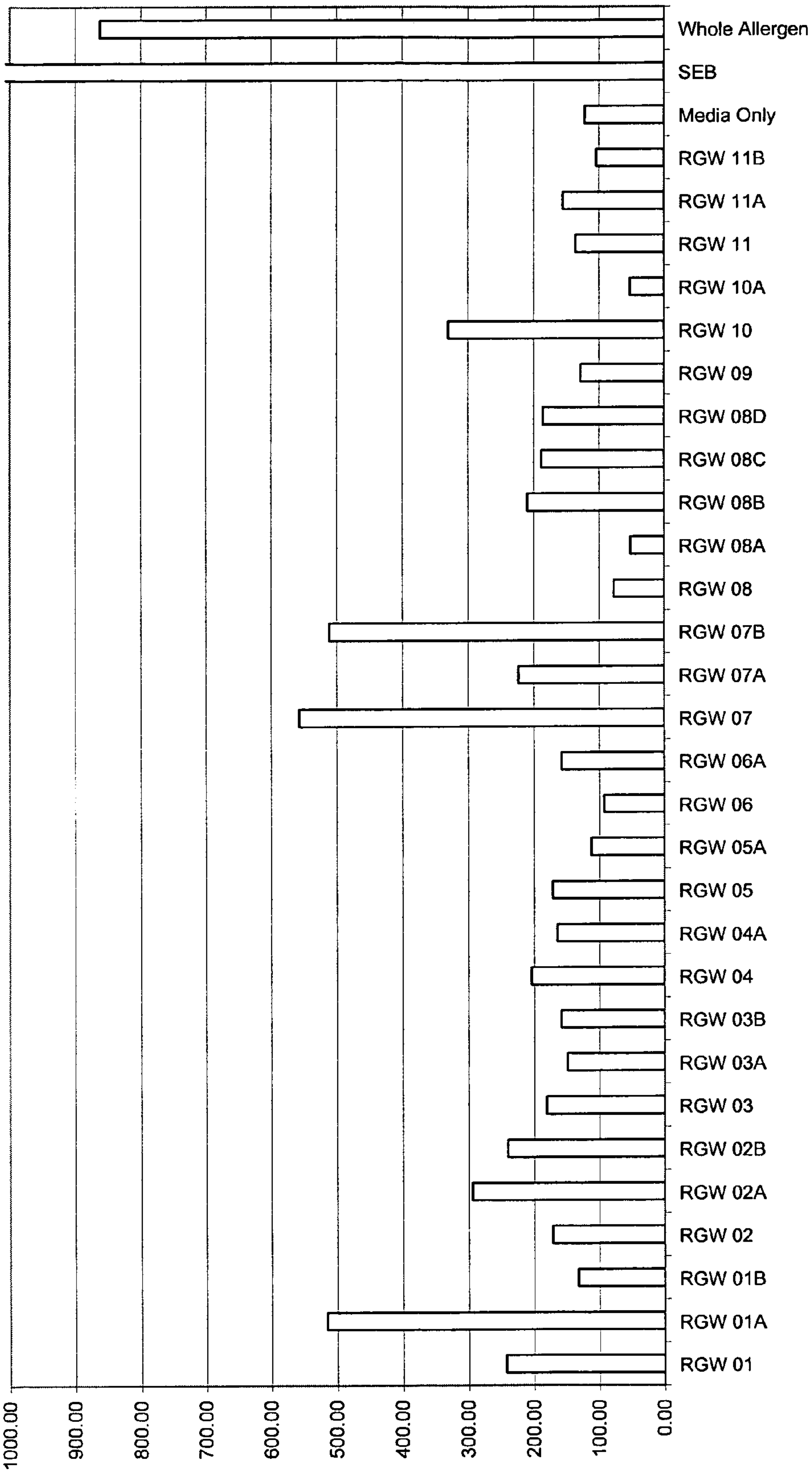
FIGS. 3 and 4 show mean IL-10 release (y axis, pg/ml) in response to the ragweed peptides shown on the x axis, for a population of ragweed allergic individuals.
Figure 4:
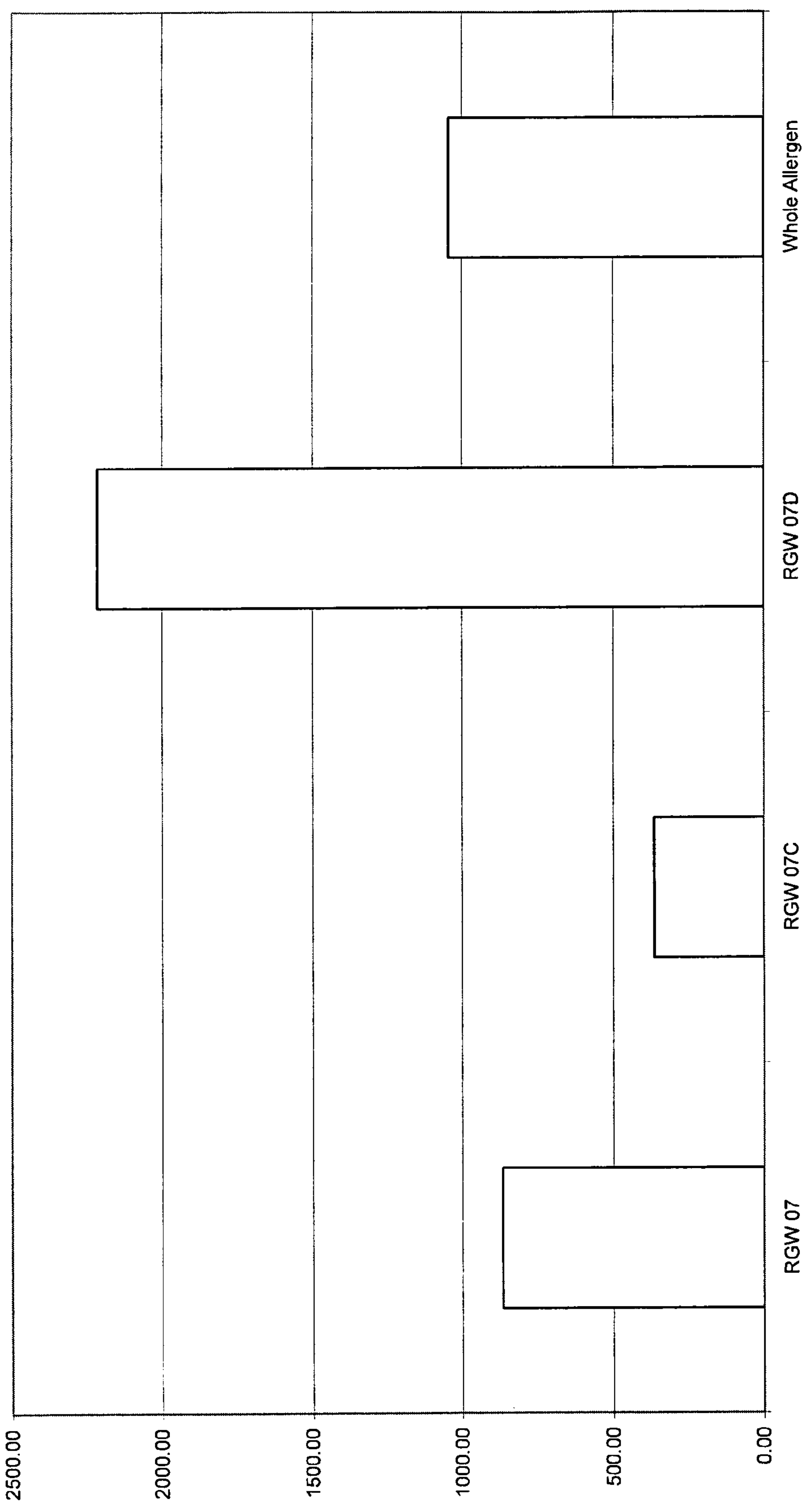

The results for the peptides of Example 1 are shown in FIGS. 1 and 2. As can be seen, peptides HDM03D, HDM03E, HDM202, HDM03V and HDM03W give rise to higher IL-10 production than other peptides. In addition, peptides HDM03E, HDM202 and HDM03W give rise to higher IL-10 release than whole allergen. The results for the peptides in Example 2 are shown in FIGS. 3 and 4. As can be seen, peptides RGW07, B, C and D give rise to higher IL-10 production than other peptides. In addition, peptide RGW07D gives rise to higher IL-10 release than whole allergen.

Example 4

In Vivo Efficacy of Peptides of the Invention for Treatment of Allergy

Peptides of the invention were evaluated for efficacy in treatment of allergy in a mouse model. Six groups of BALB/cJ mice were sensitised with repeat dosing of 1.5 micrograms of whole house dust mite (HDM) allergen intranasally (in 25 uL) for 5×2 days over 2 weeks. This served as a model system for investigation of allergic asthma caused by whole HDM allergen.

The sensitised mice were then left for one week before treatment with peptides of the invention. The treatment comprised intranasal delivery of HDM03D followed 30 minutes later by intranasal delivery of HDM202 daily for 5 days. Approximately 4 weeks later the mice were challenged with whole HDM allergen for 2 days (2×15 ug/25 uL intranasally) and outcomes were measured 48 hours later. 5 doses of HDM202 & HDM03D were evaluated (10, 1, 0.1, 0.01 & 0.001 ug per peptide).

In the treatment phase, there were 4 mice in the vehicle group, and 3 mice in each of the HDM03D/HDM202 groups except the 0.01 ug dose which had 2 mice/group. The outcomes measured were bronchial airway resistance following methacholine lung challenge (cm $H_20$/mL/s), a measure of respiratory function, and a quantitation of inflammatory cells in the bronchoalveolar lavage (BAL) fluid.

For measurement of airway resistance, 48 hours after intranasal challenge over 2 days (2×15 ug) with house dust mite whole allergen, total respiratory system resistance (Rrs) was measured in response to intranasal saline and increasing doses of intravenous methacholine (MCh) using the Flexivent rodent ventilator. Using the resulting Rrs-MCh dose-response curves, indices of airway reactivity (Slope Rrs) and maximal degree of bronchoconstriction at 25 MCh mg/mL (Max Rrs @ 25 mg/mL) were measured. Values are means+/−SE.

For quantitation of inflammatory cells, bronchoalveolar lavage fluid (BALF) was assessed for total and differential inflammatory cell counts. Sections of lung tissue were stained with hematoxylin and eosin (H&E) and morphometrically quantified using a custom computerized analysis system (Northern Eclipse).

Figure 5:
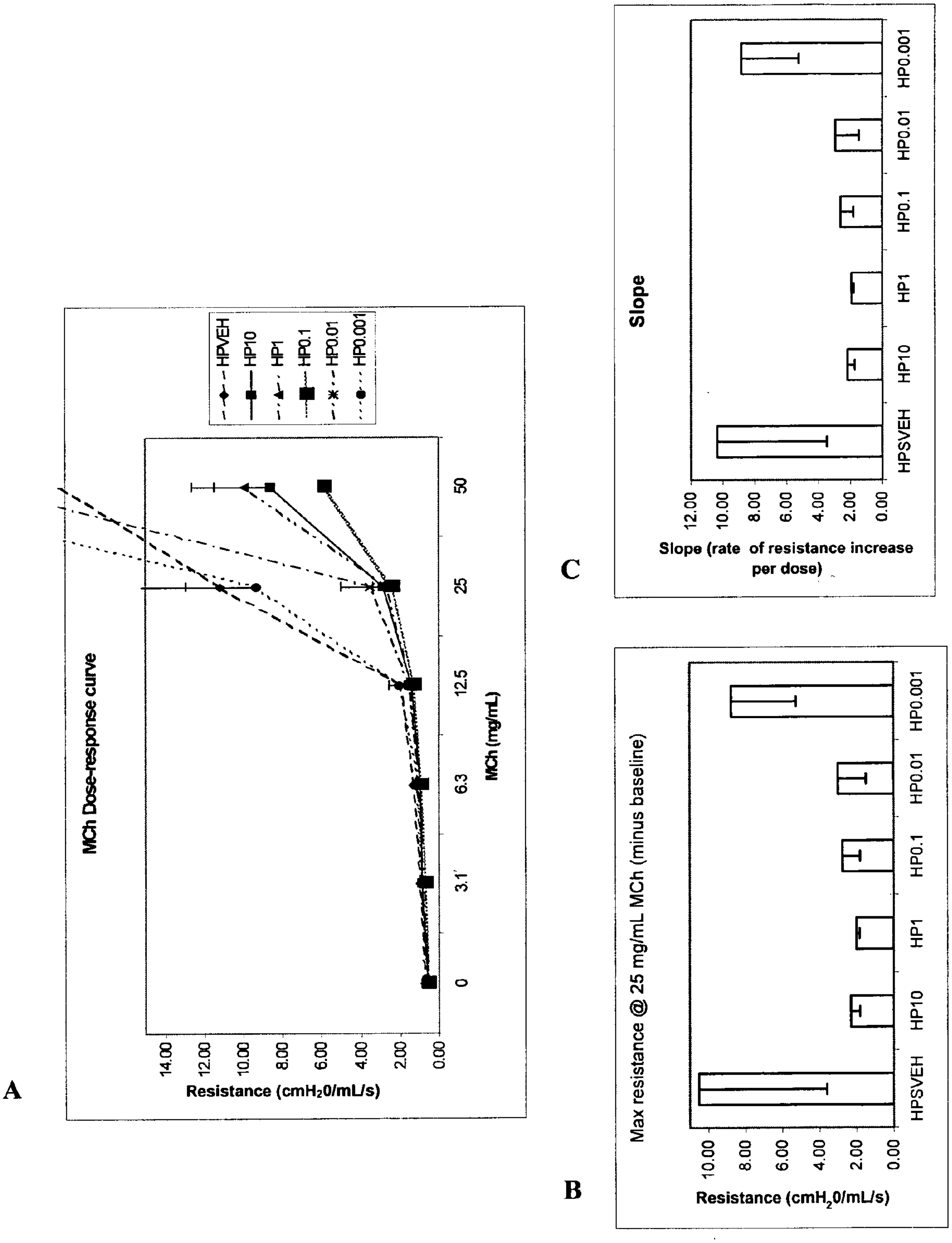
FIG. 5 shows bronchial airway resistance following methacholine lung challenge in mice treated with vehicle or doses of peptides HDM03D and HDM202.
Figure 6:
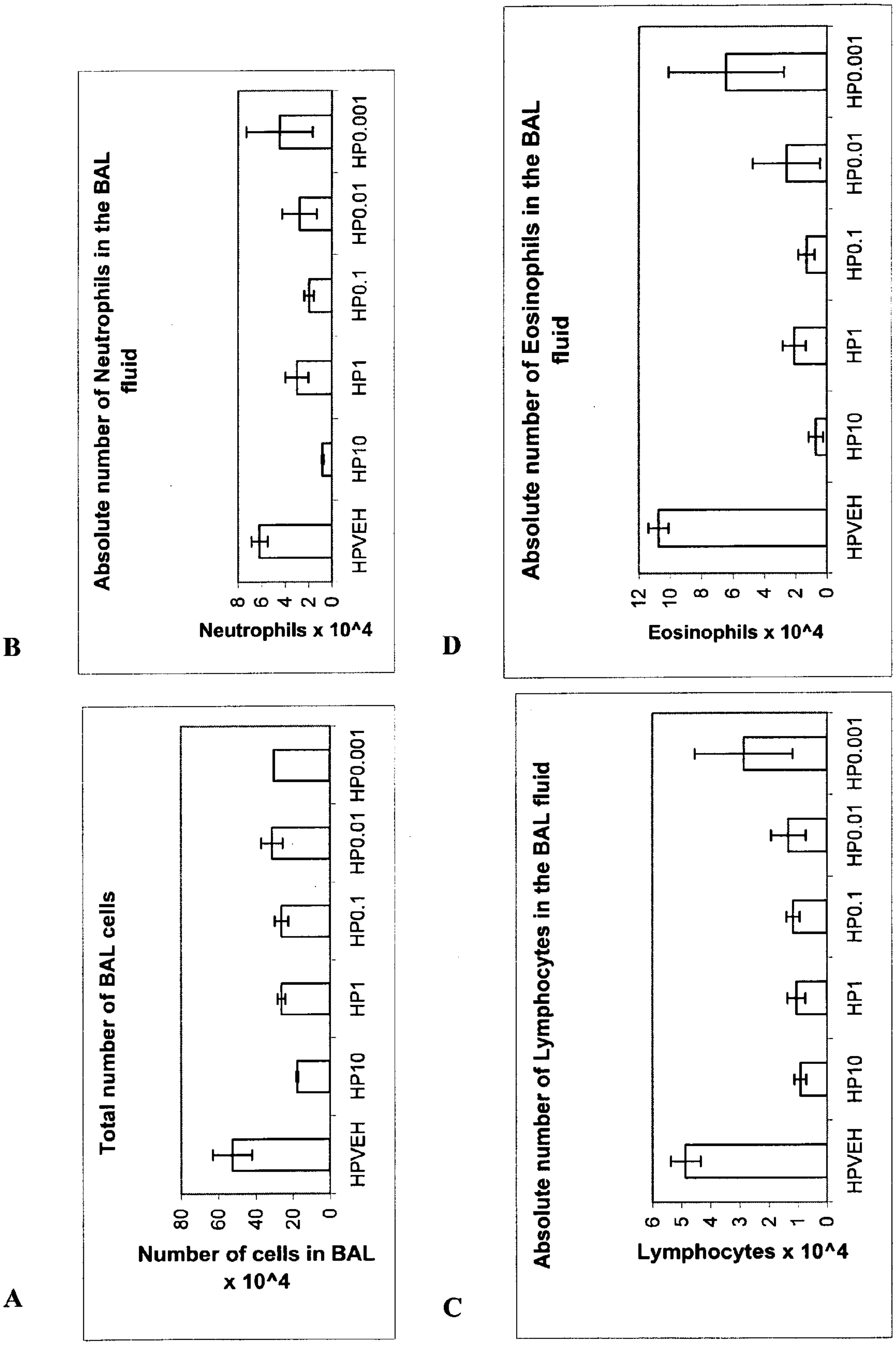
FIG. 6 shows quantitation of inflammatory cells in the bronchoalveolar lavage (BAL) fluid.

The results are shown in FIGS. 5 and 6. FIG. 5A shows that treatment with HDM03D & HDM202 resulted in a significant decrease in airway resistance with the 10, 1 and 0.1 ug doses being the most effective. When the 25 mg/ml methacholine challenge dose was analysed (FIG. 5B) there was a clear reduction in resistance at the top 4 doses of HDM peptides with no effect at the lowest dose of 0.001 ug. As shown in FIG. 5C, the slope or rate of resistance increase gave a similar pattern to the resistance.

As shown in FIG. 6A, HDM03D & HDM202 peptide treatment also resulted in a reduction in BAL total cells in all 5 dose groups. When this was further analysed in terms of individual cell populations, there was a dose responsive reduction in neutrophils (FIG. 6B), eosinophils (FIG. 6C) and lymphocytes (FIG. 6D).

The data therefore shows that treatment with HDM03D & HDM202 inhibited cellular infiltration into the bronchoalveolar space following allergen challenge and significantly reduced the increase in air resistance associated with allergic lung responses in asthma.

The invention claimed is:

1. A method of treating dust mite allergy comprising administering to a subject in need thereof a therapeutically effective amount of a polypeptide consisting of the sequence of ELVDSASQHG (HDM03W; SEQ ID NO: 4), or of the sequence ELVDSASQHG wherein the N terminal glutamate (E) residue is replaced with pyroglutamate (SEQ ID NO: 195).

2. A method of treating dust mite allergy comprising administering to a subject in need thereof a therapeutically effective amount of a polypeptide consisting of the sequence ELVDSASQHG wherein the N terminal glutamate (E) residue is replaced with pyroglutamate (SEQ ID NO: 195).

3. The method of claim 1, wherein the polypeptide consists of the sequence ELVDSASQHG wherein the N terminal glutamate (E) residue is replaced with pyroglutamate (SEQ ID NO: 195).

4. The method of claim 1 or 2 wherein the polypeptide is administered sequentially or in combination with a second polypeptide.

5. The method of claim 1 or 2 wherein the polypeptide is formulated with a carrier.

* * * * *

SEQUENCE LISTING

```
<160> NUMBER OF SEQ ID NOS: 195

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence: Synthetic
      HDM03D peptide

<400> SEQUENCE: 1

Arg Asn Gln Ser Leu Asp Leu Ala Glu Gln Glu Leu Val Asp Ser Ala
1               5                   10                  15

Ser Gln His


<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic
      HDM03E peptide
<220> FEATURE:
<221> NAME/KEY: MOD_RES
<222> LOCATION: (15)..(15)
<223> OTHER INFORMATION: 5-aminobutyric acid

<400> SEQUENCE: 2

Arg Asn Gln Ser Leu Asp Leu Ala Glu Gln Glu Leu Val Asp Xaa Ala
1               5                   10                  15
```

Ser Gln His

<210> SEQ ID NO 3
<211> LENGTH: 12
<212> TYPE: PRT
<213> ORGANISM: Dermatophagoides pteronyssinus

<400> SEQUENCE: 3

Glu Gln Glu Leu Val Asp Ser Ala Ser Gln His Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      HDM03W peptide

<400> SEQUENCE: 4

Glu Leu Val Asp Ser Ala Ser Gln His Gly
1               5                   10

<210> SEQ ID NO 5
<211> LENGTH: 15
<212> TYPE: PRT
<213> ORGANISM: Dermatophagoides pteronyssinus

<400> SEQUENCE: 5

Asp Glu Phe Lys Asn Arg Phe Leu Met Ser Ala Glu Ala Phe Glu
1               5                   10                  15

<210> SEQ ID NO 6
<211> LENGTH: 15
<212> TYPE: PRT
<213> ORGANISM: Ambrosia artemisiifolia

<400> SEQUENCE: 6

Gly Glu Ala Ala Ile Lys Leu Thr Ser Ser Ala Gly Val Leu Ser
1               5                   10                  15

<210> SEQ ID NO 7
<211> LENGTH: 15
<212> TYPE: PRT
<213> ORGANISM: Ambrosia artemisiifolia

<400> SEQUENCE: 7

Gly Glu Ala Val Leu Arg Leu Thr Ser Ser Ala Gly Val Leu Ser
1               5                   10                  15

<210> SEQ ID NO 8
<211> LENGTH: 15
<212> TYPE: PRT
<213> ORGANISM: Ambrosia artemisiifolia

<400> SEQUENCE: 8

Gly Glu Ser Ala Leu Ser Leu Thr Ser Ser Ala Gly Val Leu Ser
1               5                   10                  15

<210> SEQ ID NO 9
<211> LENGTH: 17
<212> TYPE: PRT
<213> ORGANISM: Ambrosia artemisiifolia

<400> SEQUENCE: 9

Lys Gly Glu Ala Ala Ile Lys Leu Thr Ser Ser Ala Gly Val Leu Ser
1 5 10 15

Lys

<210> SEQ ID NO 10
<211> LENGTH: 18
<212> TYPE: PRT
<213> ORGANISM: Ambrosia artemisiifolia

<400> SEQUENCE: 10

Lys Gly Glu Ala Ala Ile Lys Leu Thr Ser Ser Ala Gly Val Leu Ser
1 5 10 15

Lys Lys

<210> SEQ ID NO 11
<211> LENGTH: 320
<212> TYPE: PRT
<213> ORGANISM: Dermatophagoides pteronyssinus

<400> SEQUENCE: 11

Met Lys Ile Val Leu Ala Ile Ala Ser Leu Leu Ala Leu Ser Ala Val
1 5 10 15

Tyr Ala Arg Pro Ser Ser Ile Lys Thr Phe Glu Glu Tyr Lys Lys Ala
20 25 30

Phe Asn Lys Ser Tyr Ala Thr Phe Glu Asp Glu Glu Ala Ala Arg Lys
35 40 45

Asn Phe Leu Glu Ser Val Lys Tyr Val Gln Ser Asn Gly Gly Ala Ile
50 55 60

Asn His Leu Ser Asp Leu Ser Leu Asp Glu Phe Lys Asn Arg Phe Leu
65 70 75 80

Met Ser Ala Glu Ala Phe Glu His Leu Lys Thr Gln Phe Asp Leu Asn
85 90 95

Ala Glu Thr Asn Ala Cys Ser Ile Asn Gly Asn Ala Pro Ala Glu Ile
100 105 110

Asp Leu Arg Gln Met Arg Thr Val Thr Pro Ile Arg Met Gln Gly Gly
115 120 125

Cys Gly Ser Cys Trp Ala Phe Ser Gly Val Ala Ala Thr Glu Ser Ala
130 135 140

Tyr Leu Ala Tyr Arg Asn Gln Ser Leu Asp Leu Ala Glu Gln Glu Leu
145 150 155 160

Val Asp Cys Ala Ser Gln His Gly Cys His Gly Asp Thr Ile Pro Arg
165 170 175

Gly Ile Glu Tyr Ile Gln His Asn Gly Val Val Gln Glu Ser Tyr Tyr
180 185 190

Arg Tyr Val Ala Arg Glu Gln Ser Cys Arg Arg Pro Asn Ala Gln Arg
195 200 205

Phe Gly Ile Ser Asn Tyr Cys Gln Ile Tyr Pro Pro Asn Val Asn Lys
210 215 220

Ile Arg Glu Ala Leu Ala Gln Thr His Ser Ala Ile Ala Val Ile Ile
225 230 235 240

Gly Ile Lys Asp Leu Asp Ala Phe Arg His Tyr Asp Gly Arg Thr Ile
245 250 255

Ile Gln Arg Asp Asn Gly Tyr Gln Pro Asn Tyr His Ala Val Asn Ile
260 265 270

Val Gly Tyr Ser Asn Ala Gln Gly Val Asp Tyr Trp Ile Val Arg Asn
275 280 285

Ser Trp Asp Thr Asn Trp Gly Asp Asn Gly Tyr Gly Tyr Phe Ala Ala
    290                 295                 300

Asn Ile Asp Leu Met Met Ile Glu Glu Tyr Pro Tyr Val Val Ile Leu
305                 310                 315                 320

<210> SEQ ID NO 12
<211> LENGTH: 146
<212> TYPE: PRT
<213> ORGANISM: Dermatophagoides pteronyssinus

<400> SEQUENCE: 12

Met Met Tyr Lys Ile Leu Cys Leu Ser Leu Leu Val Ala Ala Val Ala
1               5                   10                  15

Arg Asp Gln Val Asp Val Lys Asp Cys Ala Asn His Glu Ile Lys Lys
            20                  25                  30

Val Leu Val Pro Gly Cys His Gly Ser Glu Pro Cys Ile Ile His Arg
        35                  40                  45

Gly Lys Pro Phe Gln Leu Glu Ala Val Phe Glu Ala Asn Gln Asn Thr
    50                  55                  60

Lys Thr Ala Lys Ile Glu Ile Lys Ala Ser Ile Asp Gly Leu Glu Val
65                  70                  75                  80

Asp Val Pro Gly Ile Asp Pro Asn Ala Cys His Tyr Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Val Thr Val Lys Val Met
        115                 120                 125

Gly Asp Asp Gly Val Leu Ala Cys Ala Ile Ala Thr His Ala Lys Ile
    130                 135                 140

Arg Asp
145

<210> SEQ ID NO 13
<211> LENGTH: 261
<212> TYPE: PRT
<213> ORGANISM: Dermatophagoides pteronyssinus

<400> SEQUENCE: 13

Met Ile Ile Tyr Asn Ile Leu Ile Val Leu Leu Leu Ala Ile Asn Thr
1               5                   10                  15

Leu Ala Asn Pro Ile Leu Pro Ala Ser Pro Asn Ala Thr Ile Val Gly
            20                  25                  30

Gly Glu Lys Ala Leu Ala Gly Glu Cys Pro Tyr Gln Ile Ser Leu Gln
        35                  40                  45

Ser Ser Ser His Phe Cys Gly Gly Thr Ile Leu Asp Glu Tyr Trp Ile
    50                  55                  60

Leu Thr Ala Ala His Cys Val Ala Gly Gln Thr Ala Ser Lys Leu Ser
65                  70                  75                  80

Ile Arg Tyr Asn Ser Leu Lys His Ser Leu Gly Gly Glu Lys Ile Ser
                85                  90                  95

Val Ala Lys Ile Phe Ala His Glu Lys Tyr Asp Ser Tyr Gln Ile Asp
            100                 105                 110

Asn Asp Ile Ala Leu Ile Lys Leu Lys Ser Pro Met Lys Leu Asn Gln
        115                 120                 125

Lys Asn Ala Lys Ala Val Gly Leu Pro Ala Lys Gly Ser Asp Val Lys
    130                 135                 140

Val Gly Asp Gln Val Arg Val Ser Gly Trp Gly Tyr Leu Glu Glu Gly
145 150 155 160

Ser Tyr Ser Leu Pro Ser Glu Leu Arg Arg Val Asp Ile Ala Val Val
165 170 175

Ser Arg Lys Glu Cys Asn Glu Leu Tyr Ser Lys Ala Asn Ala Glu Val
180 185 190

Thr Asp Asn Met Ile Cys Gly Gly Asp Val Ala Asn Gly Gly Lys Asp
195 200 205

Ser Cys Gln Gly Asp Ser Gly Gly Pro Val Val Asp Val Lys Asn Asn
210 215 220

Gln Val Val Gly Ile Val Ser Trp Gly Tyr Gly Cys Ala Arg Lys Gly
225 230 235 240

Tyr Pro Gly Val Tyr Thr Arg Val Gly Asn Phe Ile Asp Trp Ile Glu
245 250 255

Ser Lys Arg Ser Gln
260

<210> SEQ ID NO 14
<211> LENGTH: 19
<212> TYPE: PRT
<213> ORGANISM: Dermatophagoides pteronyssinus
<220> FEATURE:
<221> NAME/KEY: MOD_RES
<222> LOCATION: (3)..(3)
<223> OTHER INFORMATION: Any naturally occurring amino acid
<220> FEATURE:
<221> NAME/KEY: MOD_RES
<222> LOCATION: (10)..(10)
<223> OTHER INFORMATION: Any naturally occurring amino acid
<220> FEATURE:
<221> NAME/KEY: MOD_RES
<222> LOCATION: (16)..(16)
<223> OTHER INFORMATION: Any naturally occurring amino acid

<400> SEQUENCE: 14

Lys Tyr Xaa Asn Pro His Phe Ile Gly Xaa Arg Ser Val Ile Thr Xaa
1 5 10 15

Leu Met Glu

<210> SEQ ID NO 15
<211> LENGTH: 132
<212> TYPE: PRT
<213> ORGANISM: Dermatophagoides pteronyssinus

<400> SEQUENCE: 15

Met Lys Phe Ile Ile Ala Phe Phe Val Ala Thr Leu Ala Val Met Thr
1 5 10 15

Val Ser Gly Glu Asp Lys Lys His Asp Tyr Gln Asn Glu Phe Asp Phe
20 25 30

Leu Leu Met Glu Arg Ile His Glu Gln Ile Lys Lys Gly Glu Leu Ala
35 40 45

Leu Phe Tyr Leu Gln Glu Gln Ile Asn His Phe Glu Glu Lys Pro Thr
50 55 60

Lys Glu Met Lys Asp Lys Ile Val Ala Glu Met Asp Thr Ile Ile Ala
65 70 75 80

Met Ile Asp Gly Val Arg Gly Val Leu Asp Arg Leu Met Gln Arg Lys
85 90 95

Asp Leu Asp Ile Phe Glu Gln Tyr Asn Leu Glu Met Ala Lys Lys Ser
100 105 110

```
Gly Asp Ile Leu Glu Arg Asp Leu Lys Lys Glu Glu Ala Arg Val Lys
        115                 120                 125

Lys Ile Glu Val
    130


<210> SEQ ID NO 16
<211> LENGTH: 20
<212> TYPE: PRT
<213> ORGANISM: Dermatophagoides pteronyssinus
<220> FEATURE:
<221> NAME/KEY: MOD_RES
<222> LOCATION: (4)..(4)
<223> OTHER INFORMATION: Any naturally occurring amino acid

<400> SEQUENCE: 16

Ala Ile Gly Xaa Gln Pro Ala Ala Glu Ala Glu Ala Pro Phe Gln Ile
1               5                   10                  15

Ser Leu Met Lys
            20


<210> SEQ ID NO 17
<211> LENGTH: 215
<212> TYPE: PRT
<213> ORGANISM: Dermatophagoides pteronyssinus

<400> SEQUENCE: 17

Met Met Lys Leu Leu Leu Ile Ala Ala Ala Ala Phe Val Ala Val Ser
1               5                   10                  15

Ala Asp Pro Ile His Tyr Asp Lys Ile Thr Glu Glu Ile Asn Lys Ala
            20                  25                  30

Val Asp Glu Ala Val Ala Ala Ile Glu Lys Ser Glu Thr Phe Asp Pro
        35                  40                  45

Met Lys Val Pro Asp His Ser Asp Lys Phe Glu Arg His Ile Gly Ile
    50                  55                  60

Ile Asp Leu Lys Gly Glu Leu Asp Met Arg Asn Ile Gln Val Arg Gly
65                  70                  75                  80

Leu Lys Gln Met Lys Arg Val Gly Asp Ala Asn Val Lys Ser Glu Asp
                85                  90                  95

Gly Val Val Lys Ala His Leu Leu Val Gly Val His Asp Asp Val Val
            100                 105                 110

Ser Met Glu Tyr Asp Leu Ala Tyr Lys Leu Gly Asp Leu His Pro Asn
        115                 120                 125

Thr His Val Ile Ser Asp Ile Gln Asp Phe Val Val Glu Leu Ser Leu
    130                 135                 140

Glu Val Ser Glu Glu Gly Asn Met Thr Leu Thr Ser Phe Glu Val Arg
145                 150                 155                 160

Gln Phe Ala Asn Val Val Asn His Ile Gly Gly Leu Ser Ile Leu Asp
                165                 170                 175

Pro Ile Phe Ala Val Leu Ser Asp Val Leu Thr Ala Ile Phe Gln Asp
            180                 185                 190

Thr Val Arg Ala Glu Met Thr Lys Val Leu Ala Pro Ala Phe Lys Lys
        195                 200                 205

Glu Leu Glu Arg Asn Asn Gln
    210                 215


<210> SEQ ID NO 18
<211> LENGTH: 18
<212> TYPE: PRT
<213> ORGANISM: Dermatophagoides pteronyssinus
```

<400> SEQUENCE: 18

```
Ile Val Gly Gly Ser Asn Ala Ser Pro Gly Asp Ala Val Tyr Gln Ile
1               5                   10                  15

Ala Leu
```

<210> SEQ ID NO 19
<211> LENGTH: 319
<212> TYPE: PRT
<213> ORGANISM: Dermatophagoides farinae

<400> SEQUENCE: 19

```
Met Lys Phe Val Leu Ala Ile Ala Ser Leu Leu Val Leu Thr Val Tyr
1               5                   10                  15

Ala Arg Pro Ala Ser Ile Lys Thr Phe Glu Phe Lys Lys Ala Phe Asn
            20                  25                  30

Lys Asn Tyr Ala Thr Val Glu Glu Glu Glu Val Ala Arg Lys Asn Phe
        35                  40                  45

Leu Glu Ser Leu Lys Tyr Val Glu Ala Asn Lys Gly Ala Ile Asn His
    50                  55                  60

Leu Ser Asp Leu Ser Leu Asp Glu Phe Lys Asn Arg Tyr Leu Met Ser
65                  70                  75                  80

Ala Glu Ala Phe Glu Gln Leu Lys Thr Gln Phe Asp Leu Asn Ala Glu
                85                  90                  95

Thr Ser Ala Cys Arg Ile Asn Ser Val Asn Val Pro Ser Glu Leu Asp
            100                 105                 110

Leu Arg Ser Leu Arg Thr Val Thr Pro Ile Arg Met Gln Gly Gly Cys
        115                 120                 125

Gly Ser Cys Trp Ala Phe Ser Gly Val Ala Ala Thr Glu Ser Ala Tyr
    130                 135                 140

Leu Ala Tyr Arg Asn Thr Ser Leu Asp Leu Ser Glu Gln Glu Leu Val
145                 150                 155                 160

Asp Cys Ala Ser Gln His Gly Cys His Gly Asp Thr Ile Pro Arg Gly
                165                 170                 175

Ile Glu Tyr Ile Gln Gln Asn Gly Val Val Glu Glu Arg Ser Tyr Pro
            180                 185                 190

Tyr Val Ala Arg Glu Gln Arg Cys Arg Arg Pro Asn Ser Gln His Tyr
        195                 200                 205

Gly Ile Ser Asn Tyr Cys Gln Ile Tyr Pro Pro Asp Val Lys Gln Ile
    210                 215                 220

Arg Glu Ala Leu Thr Gln Thr His Thr Ala Ile Ala Val Ile Ile Gly
225                 230                 235                 240

Ile Lys Asp Leu Arg Ala Phe Gln His Tyr Asp Gly Arg Thr Ile Ile
                245                 250                 255

Gln His Asp Asn Gly Tyr Gln Pro Asn Tyr His Ala Val Asn Ile Val
            260                 265                 270

Gly Tyr Gly Ser Thr Gln Gly Asp Asp Tyr Trp Ile Val Arg Asn Ser
        275                 280                 285

Trp Asp Thr Thr Trp Gly Asp Ser Gly Tyr Gly Tyr Phe Gln Ala Gly
    290                 295                 300

Asn Asn Leu Met Met Ile Glu Gln Tyr Pro Tyr Val Val Ile Met
305                 310                 315
```

<210> SEQ ID NO 20
<211> LENGTH: 146

<212> TYPE: PRT
<213> ORGANISM: Dermatophagoides farinae

<400> SEQUENCE: 20

```
Met Ile Ser Lys Ile Leu Cys Leu Ser Leu Leu Val Ala Ala Val Val
1               5                   10                  15

Ala Asp Gln Val Asp Val Lys Asp Cys Ala Asn Asn Glu Ile Lys Lys
            20                  25                  30

Val Met Val Asp Gly Cys His Gly Ser Asp Pro Cys Ile Ile His Arg
        35                  40                  45

Gly Lys Pro Phe Thr Leu Glu Ala Leu Phe Asp Ala Asn Gln Asn Thr
    50                  55                  60

Lys Thr Ala Lys Ile Glu Ile Lys Ala Ser Leu Asp Gly Leu Glu Ile
65                  70                  75                  80

Asp Val Pro Gly Ile Asp Thr Asn Ala Cys His Phe Met Lys Cys Pro
                85                  90                  95

Leu Val Lys Gly Gln Gln Tyr Asp Ile Lys Tyr Thr Trp Asn Val Pro
            100                 105                 110

Lys Ile Ala Pro Lys Ser Glu Asn Val Val Val Thr Val Lys Leu Ile
        115                 120                 125

Gly Asp Asn Gly Val Leu Ala Cys Ala Ile Ala Thr His Gly Lys Ile
    130                 135                 140

Arg Asp
145
```

<210> SEQ ID NO 21
<211> LENGTH: 259
<212> TYPE: PRT
<213> ORGANISM: Dermatophagoides farinae

<400> SEQUENCE: 21

```
Met Met Ile Leu Thr Ile Val Val Leu Leu Ala Ala Asn Ile Leu Ala
1               5                   10                  15

Thr Pro Ile Leu Pro Ser Ser Pro Asn Ala Thr Ile Val Gly Gly Val
            20                  25                  30

Lys Ala Gln Ala Gly Asp Cys Pro Tyr Gln Ile Ser Leu Gln Ser Ser
        35                  40                  45

Ser His Phe Cys Gly Gly Ser Ile Leu Asp Glu Tyr Trp Ile Leu Thr
    50                  55                  60

Ala Ala His Cys Val Asn Gly Gln Ser Ala Lys Lys Leu Ser Ile Arg
65                  70                  75                  80

Tyr Asn Thr Leu Lys His Ala Ser Gly Gly Glu Lys Ile Gln Val Ala
                85                  90                  95

Glu Ile Tyr Gln His Glu Asn Tyr Asp Ser Met Thr Ile Asp Asn Asp
            100                 105                 110

Val Ala Leu Ile Lys Leu Lys Thr Pro Met Thr Leu Asp Gln Thr Asn
        115                 120                 125

Ala Lys Pro Val Pro Leu Pro Ala Gln Gly Ser Asp Val Lys Val Gly
    130                 135                 140

Asp Lys Ile Arg Val Ser Gly Trp Gly Tyr Leu Gln Glu Gly Ser Tyr
145                 150                 155                 160

Ser Leu Pro Ser Glu Leu Gln Arg Val Asp Ile Asp Val Val Ser Arg
                165                 170                 175

Glu Gln Cys Asp Gln Leu Tyr Ser Lys Ala Gly Ala Asp Val Ser Glu
            180                 185                 190
```

```
Asn Met Ile Cys Gly Gly Asp Val Ala Asn Gly Gly Val Asp Ser Cys
        195                 200                 205

Gln Gly Asp Ser Gly Gly Pro Val Val Asp Val Ala Thr Lys Gln Ile
    210                 215                 220

Val Gly Ile Val Ser Trp Gly Tyr Gly Cys Ala Arg Lys Gly Tyr Pro
225                 230                 235                 240

Gly Val Tyr Thr Arg Val Gly Asn Phe Val Asp Trp Ile Glu Ser Lys
                245                 250                 255

Arg Ser Gln


<210> SEQ ID NO 22
<211> LENGTH: 20
<212> TYPE: PRT
<213> ORGANISM: Dermatophagoides farinae

<400> SEQUENCE: 22

Ala Val Gly Gly Gln Asp Ala Asp Leu Ala Glu Ala Pro Phe Gln Ile
1               5                   10                  15

Ser Leu Leu Lys
            20


<210> SEQ ID NO 23
<211> LENGTH: 213
<212> TYPE: PRT
<213> ORGANISM: Dermatophagoides farinae

<400> SEQUENCE: 23

Met Met Lys Phe Leu Leu Ile Ala Ala Val Ala Phe Val Ala Val Ser
1               5                   10                  15

Ala Asp Pro Ile His Tyr Asp Lys Ile Thr Glu Glu Ile Asn Lys Ala
            20                  25                  30

Ile Asp Asp Ala Ile Ala Ala Ile Glu Gln Ser Glu Thr Ile Asp Pro
        35                  40                  45

Met Lys Val Pro Asp His Ala Asp Lys Phe Glu Arg His Val Gly Ile
    50                  55                  60

Val Asp Phe Lys Gly Glu Leu Ala Met Arg Asn Ile Glu Ala Arg Gly
65                  70                  75                  80

Leu Lys Gln Met Lys Arg Gln Gly Asp Ala Asn Val Lys Gly Glu Glu
                85                  90                  95

Gly Ile Val Lys Ala His Leu Leu Ile Gly Val His Asp Asp Ile Val
            100                 105                 110

Ser Met Glu Tyr Asp Leu Ala Tyr Lys Leu Gly Asp Leu His Pro Thr
        115                 120                 125

Thr His Val Ile Ser Asp Ile Gln Asp Phe Val Val Ala Leu Ser Leu
    130                 135                 140

Glu Ile Ser Asp Glu Gly Asn Ile Thr Met Thr Ser Phe Glu Val Arg
145                 150                 155                 160

Gln Phe Ala Asn Val Val Asn His Ile Gly Gly Leu Ser Ile Leu Asp
                165                 170                 175

Pro Ile Phe Gly Val Leu Ser Asp Val Leu Thr Ala Ile Phe Gln Asp
            180                 185                 190

Thr Val Arg Lys Glu Met Thr Lys Val Leu Ala Pro Ala Phe Lys Arg
        195                 200                 205

Glu Leu Glu Lys Asn
    210
```

<210> SEQ ID NO 24
<211> LENGTH: 138
<212> TYPE: PRT
<213> ORGANISM: Hevea brasiliensis

<400> SEQUENCE: 24

```
Met Ala Glu Asp Glu Asp Asn Gln Gln Gly Gln Gly Glu Gly Leu Lys
1               5                   10                  15

Tyr Leu Gly Phe Val Gln Asp Ala Ala Thr Tyr Ala Val Thr Thr Phe
            20                  25                  30

Ser Asn Val Tyr Leu Phe Ala Lys Asp Lys Ser Gly Pro Leu Gln Pro
        35                  40                  45

Gly Val Asp Ile Ile Glu Gly Pro Val Lys Asn Val Ala Val Pro Leu
    50                  55                  60

Tyr Asn Arg Phe Ser Tyr Ile Pro Asn Gly Ala Leu Lys Phe Val Asp
65                  70                  75                  80

Ser Thr Val Val Ala Ser Val Thr Ile Ile Asp Arg Ser Leu Pro Pro
                85                  90                  95

Ile Val Lys Asp Ala Ser Ile Gln Val Val Ser Ala Ile Arg Ala Ala
            100                 105                 110

Pro Glu Ala Ala Arg Ser Leu Ala Ser Ser Leu Pro Gly Gln Thr Lys
        115                 120                 125

Ile Leu Ala Lys Val Phe Tyr Gly Glu Asn
    130                 135
```

<210> SEQ ID NO 25
<211> LENGTH: 204
<212> TYPE: PRT
<213> ORGANISM: Hevea brasiliensis

<400> SEQUENCE: 25

```
Met Ala Glu Glu Val Glu Glu Glu Arg Leu Lys Tyr Leu Asp Phe Val
1               5                   10                  15

Arg Ala Ala Gly Val Tyr Ala Val Asp Ser Phe Ser Thr Leu Tyr Leu
            20                  25                  30

Tyr Ala Lys Asp Ile Ser Gly Pro Leu Lys Pro Gly Val Asp Thr Ile
        35                  40                  45

Glu Asn Val Val Lys Thr Val Val Thr Pro Val Tyr Tyr Ile Pro Leu
    50                  55                  60

Glu Ala Val Lys Phe Val Asp Lys Thr Val Asp Val Ser Val Thr Ser
65                  70                  75                  80

Leu Asp Gly Val Val Pro Pro Val Ile Lys Gln Val Ser Ala Gln Thr
                85                  90                  95

Tyr Ser Val Ala Gln Asp Ala Pro Arg Ile Val Leu Asp Val Ala Ser
            100                 105                 110

Ser Val Phe Asn Thr Gly Val Gln Glu Gly Ala Lys Ala Leu Tyr Ala
        115                 120                 125

Asn Leu Glu Pro Lys Ala Glu Gln Tyr Ala Val Ile Thr Trp Arg Ala
    130                 135                 140

Leu Asn Lys Leu Pro Leu Val Pro Gln Val Ala Asn Val Val Val Pro
145                 150                 155                 160

Thr Ala Val Tyr Phe Ser Glu Lys Tyr Asn Asp Val Val Arg Gly Thr
                165                 170                 175

Thr Glu Gln Gly Tyr Arg Val Ser Ser Tyr Leu Pro Leu Leu Pro Thr
            180                 185                 190

Glu Lys Ile Thr Lys Val Phe Gly Asp Glu Ala Ser
```

195 200

<210> SEQ ID NO 26
<211> LENGTH: 133
<212> TYPE: PRT
<213> ORGANISM: Parietaria judaica

<400> SEQUENCE: 26

Met Arg Thr Val Ser Met Ala Ala Leu Val Val Ile Ala Ala Ala Leu
1 5 10 15

Ala Trp Thr Ser Ser Ala Glu Pro Ala Pro Ala Pro Ala Pro Gly Glu
20 25 30

Glu Ala Cys Gly Lys Val Val Gln Asp Ile Met Pro Cys Leu His Phe
35 40 45

Val Lys Gly Glu Glu Lys Glu Pro Ser Lys Glu Cys Cys Ser Gly Thr
50 55 60

Lys Lys Leu Ser Glu Glu Val Lys Thr Thr Glu Gln Lys Arg Glu Ala
65 70 75 80

Cys Lys Cys Ile Val Arg Ala Thr Lys Gly Ile Ser Gly Ile Lys Asn
85 90 95

Glu Leu Val Ala Glu Val Pro Lys Lys Cys Asp Ile Lys Thr Thr Leu
100 105 110

Pro Pro Ile Thr Ala Asp Phe Asp Cys Ser Lys Ile Gln Ser Thr Ile
115 120 125

Phe Arg Gly Tyr Tyr
130

<210> SEQ ID NO 27
<211> LENGTH: 133
<212> TYPE: PRT
<213> ORGANISM: Parietaria judaica

<400> SEQUENCE: 27

Met Val Arg Ala Leu Met Pro Cys Leu Pro Phe Val Gln Gly Lys Glu
1 5 10 15

Lys Glu Pro Ser Lys Gly Cys Cys Ser Gly Ala Lys Arg Leu Asp Gly
20 25 30

Glu Thr Lys Thr Gly Pro Gln Arg Val His Ala Cys Glu Cys Ile Gln
35 40 45

Thr Ala Met Lys Thr Tyr Ser Asp Ile Asp Gly Lys Leu Val Ser Glu
50 55 60

Val Pro Lys His Cys Gly Ile Val Asp Ser Lys Leu Pro Pro Ile Asp
65 70 75 80

Val Asn Met Asp Cys Lys Thr Val Gly Val Val Pro Arg Gln Pro Gln
85 90 95

Leu Pro Val Ser Leu Arg His Gly Pro Val Thr Gly Pro Ser Asp Pro
100 105 110

Ala His Lys Ala Arg Leu Glu Arg Pro Gln Ile Arg Val Pro Pro Pro
115 120 125

Ala Pro Glu Lys Ala
130

<210> SEQ ID NO 28
<211> LENGTH: 133
<212> TYPE: PRT
<213> ORGANISM: Parietaria judaica

<400> SEQUENCE: 28

```
Met Arg Thr Val Ser Met Ala Ala Leu Val Val Ile Ala Ala Ala Leu
1               5                   10                  15

Ala Trp Thr Ser Ser Ala Glu Leu Ala Ser Ala Pro Ala Pro Gly Glu
            20                  25                  30

Gly Pro Cys Gly Lys Val Val His His Ile Met Pro Cys Leu Lys Phe
        35                  40                  45

Val Lys Gly Glu Glu Lys Glu Pro Ser Lys Ser Cys Cys Ser Gly Thr
    50                  55                  60

Lys Lys Leu Ser Glu Glu Val Lys Thr Thr Glu Gln Lys Arg Glu Ala
65                  70                  75                  80

Cys Lys Cys Ile Val Ala Ala Thr Lys Gly Ile Ser Gly Ile Lys Asn
                85                  90                  95

Glu Leu Val Ala Glu Val Pro Lys Lys Cys Gly Ile Thr Thr Thr Leu
            100                 105                 110

Pro Pro Ile Thr Ala Asp Phe Asp Cys Ser Lys Ile Glu Ser Thr Ile
        115                 120                 125

Phe Arg Gly Tyr Tyr
    130


<210> SEQ ID NO 29
<211> LENGTH: 176
<212> TYPE: PRT
<213> ORGANISM: Parietaria judaica

<400> SEQUENCE: 29

Met Arg Thr Val Ser Ala Pro Ser Ala Val Ala Leu Val Val Ile Val
1               5                   10                  15

Ala Ala Gly Leu Ala Trp Thr Ser Leu Ala Ser Val Ala Pro Pro Ala
            20                  25                  30

Pro Ala Pro Gly Ser Glu Glu Thr Cys Gly Thr Val Val Arg Ala Leu
        35                  40                  45

Met Pro Cys Leu Pro Phe Val Gln Gly Lys Glu Lys Glu Pro Ser Lys
    50                  55                  60

Gly Cys Cys Ser Gly Ala Lys Arg Leu Asp Gly Glu Thr Lys Thr Gly
65                  70                  75                  80

Leu Gln Arg Val His Ala Cys Glu Cys Ile Gln Thr Ala Met Lys Thr
                85                  90                  95

Tyr Ser Asp Ile Asp Gly Lys Leu Val Ser Glu Val Pro Lys His Cys
            100                 105                 110

Gly Ile Val Asp Ser Lys Leu Pro Pro Ile Asp Val Asn Met Asp Cys
        115                 120                 125

Lys Thr Leu Gly Val Val Pro Arg Gln Pro Gln Leu Pro Val Ser Leu
    130                 135                 140

Arg His Gly Pro Val Thr Gly Pro Ser Asp Pro Ala His Lys Ala Arg
145                 150                 155                 160

Leu Glu Arg Pro Gln Ile Arg Val Pro Pro Pro Ala Pro Glu Lys Ala
                165                 170                 175


<210> SEQ ID NO 30
<211> LENGTH: 138
<212> TYPE: PRT
<213> ORGANISM: Parietaria judaica

<400> SEQUENCE: 30

Met Arg Thr Val Ser Ala Arg Ser Ser Val Ala Leu Val Val Ile Val
1               5                   10                  15
```

```
Ala Ala Val Leu Val Trp Thr Ser Ser Ala Ser Val Ala Pro Ala Pro
            20                  25                  30

Ala Pro Gly Ser Glu Glu Thr Cys Gly Thr Val Val Gly Ala Leu Met
        35                  40                  45

Pro Cys Leu Pro Phe Val Gln Gly Lys Glu Lys Glu Pro Ser Lys Gly
    50                  55                  60

Cys Cys Ser Gly Ala Lys Arg Leu Asp Gly Glu Thr Lys Thr Gly Pro
65                  70                  75                  80

Gln Arg Val His Ala Cys Glu Cys Ile Gln Thr Ala Met Lys Thr Tyr
                85                  90                  95

Ser Asp Ile Asp Gly Lys Leu Val Ser Glu Val Pro Lys His Cys Gly
            100                 105                 110

Ile Val Asp Ser Lys Leu Pro Pro Ile Asp Val Asn Met Asp Cys Lys
        115                 120                 125

Thr Leu Gly Val Leu His Tyr Lys Gly Asn
    130                 135


<210> SEQ ID NO 31
<211> LENGTH: 143
<212> TYPE: PRT
<213> ORGANISM: Parietaria judaica

<400> SEQUENCE: 31

Met Val Arg Ala Leu Met Pro Cys Leu Pro Phe Val Gln Gly Lys Glu
1               5                   10                  15

Lys Glu Pro Ser Lys Gly Cys Cys Ser Gly Ala Lys Arg Leu Asp Gly
            20                  25                  30

Glu Thr Lys Thr Gly Pro Gln Arg Val His Ala Cys Glu Cys Ile Gln
        35                  40                  45

Thr Ala Met Lys Thr Tyr Ser Asp Ile Asp Gly Lys Leu Val Ser Glu
    50                  55                  60

Val Pro Lys His Cys Gly Ile Val Asp Ser Lys Leu Pro Pro Ile Asp
65                  70                  75                  80

Val Asn Met Asp Cys Lys Thr Val Gly Val Val Pro Arg Gln Pro Gln
                85                  90                  95

Leu Pro Val Ser Leu Arg His Gly Pro Val Thr Gly Pro Ser Arg Ser
            100                 105                 110

Arg Pro Pro Thr Lys His Gly Trp Arg Asp Pro Arg Leu Glu Phe Arg
        115                 120                 125

Pro Pro His Arg Lys Lys Pro Asn Pro Ala Phe Ser Thr Leu Gly
    130                 135                 140


<210> SEQ ID NO 32
<211> LENGTH: 227
<212> TYPE: PRT
<213> ORGANISM: Vespula vulgaris

<400> SEQUENCE: 32

Met Glu Ile Ser Gly Leu Val Tyr Leu Ile Ile Ile Val Thr Ile Ile
1               5                   10                  15

Asp Leu Pro Tyr Gly Lys Ala Asn Asn Tyr Cys Lys Ile Lys Cys Leu
            20                  25                  30

Lys Gly Gly Val His Thr Ala Cys Lys Tyr Gly Ser Leu Lys Pro Asn
        35                  40                  45

Cys Gly Asn Lys Val Val Val Ser Tyr Gly Leu Thr Lys Gln Glu Lys
    50                  55                  60
```

```
Gln Asp Ile Leu Lys Glu His Asn Asp Phe Arg Gln Lys Ile Ala Arg
65                  70                  75                  80

Gly Leu Glu Thr Arg Gly Asn Pro Gly Pro Gln Pro Pro Ala Lys Asn
                85                  90                  95

Met Lys Asn Leu Val Trp Asn Asp Glu Leu Ala Tyr Val Ala Gln Val
            100                 105                 110

Trp Ala Asn Gln Cys Gln Tyr Gly His Asp Thr Cys Arg Asp Val Ala
        115                 120                 125

Lys Tyr Gln Val Gly Gln Asn Val Ala Leu Thr Gly Ser Thr Ala Ala
    130                 135                 140

Lys Tyr Asp Asp Pro Val Lys Leu Val Lys Met Trp Glu Asp Glu Val
145                 150                 155                 160

Lys Asp Tyr Asn Pro Lys Lys Lys Phe Ser Gly Asn Asp Phe Leu Lys
                165                 170                 175

Thr Gly His Tyr Thr Gln Met Val Trp Ala Asn Thr Lys Glu Val Gly
            180                 185                 190

Cys Gly Ser Ile Lys Tyr Ile Gln Glu Lys Trp His Lys His Tyr Leu
        195                 200                 205

Val Cys Asn Tyr Gly Pro Ser Gly Asn Phe Met Asn Glu Glu Leu Tyr
    210                 215                 220

Gln Thr Lys
225


<210> SEQ ID NO 33
<211> LENGTH: 300
<212> TYPE: PRT
<213> ORGANISM: Vespula maculifrons

<400> SEQUENCE: 33

Gly Pro Lys Cys Pro Phe Asn Ser Asp Thr Val Ser Ile Ile Ile Glu
1               5                   10                  15

Thr Arg Glu Asn Arg Asn Arg Asp Leu Tyr Thr Leu Gln Thr Leu Gln
            20                  25                  30

Asn His Pro Glu Phe Lys Lys Lys Thr Ile Thr Arg Pro Val Val Phe
        35                  40                  45

Ile Thr His Gly Phe Thr Ser Ser Ala Ser Glu Lys Asn Phe Ile Asn
    50                  55                  60

Leu Ala Lys Ala Leu Val Asp Lys Asp Asn Tyr Met Val Ile Ser Ile
65                  70                  75                  80

Asp Trp Gln Thr Ala Ala Cys Thr Asn Glu Tyr Pro Gly Leu Lys Tyr
                85                  90                  95

Ala Tyr Tyr Pro Thr Ala Ala Ser Asn Thr Arg Leu Val Gly Gln Tyr
            100                 105                 110

Ile Ala Thr Ile Thr Gln Lys Leu Val Lys Asp Tyr Lys Ile Ser Met
        115                 120                 125

Ala Asn Ile Arg Leu Ile Gly His Ser Leu Gly Ala His Val Ser Gly
    130                 135                 140

Phe Ala Gly Lys Arg Val Gln Glu Leu Lys Leu Gly Lys Tyr Ser Glu
145                 150                 155                 160

Ile Ile Gly Leu Asp Pro Ala Arg Pro Ser Phe Asp Ser Asn His Cys
                165                 170                 175

Ser Glu Arg Leu Cys Glu Thr Asp Ala Glu Tyr Val Gln Ile Ile His
            180                 185                 190

Thr Ser Asn Tyr Leu Gly Thr Glu Lys Ile Leu Gly Thr Val Asp Phe
```

```
        195                 200                 205

Tyr Met Asn Asn Gly Lys Asn Asn Pro Gly Cys Gly Arg Phe Phe Ser
    210                 215                 220

Glu Val Cys Ser His Thr Arg Ala Val Ile Tyr Met Ala Glu Cys Ile
225                 230                 235                 240

Lys His Glu Cys Cys Leu Ile Gly Ile Pro Arg Ser Lys Ser Ser Gln
                245                 250                 255

Pro Ile Ser Arg Cys Thr Lys Gln Glu Cys Val Cys Val Gly Leu Asn
            260                 265                 270

Ala Lys Lys Tyr Pro Ser Arg Gly Ser Phe Tyr Val Pro Val Glu Ser
        275                 280                 285

Thr Ala Pro Phe Cys Asn Asn Lys Gly Lys Ile Ile
    290                 295                 300


<210> SEQ ID NO 34
<211> LENGTH: 336
<212> TYPE: PRT
<213> ORGANISM: Vespula vulgaris

<400> SEQUENCE: 34

Met Glu Glu Asn Met Asn Leu Lys Tyr Leu Leu Leu Phe Val Tyr Phe
1               5                   10                  15

Val Gln Val Leu Asn Cys Cys Tyr Gly His Gly Asp Pro Leu Ser Tyr
            20                  25                  30

Glu Leu Asp Arg Gly Pro Lys Cys Pro Phe Asn Ser Asp Thr Val Ser
        35                  40                  45

Ile Ile Ile Glu Thr Arg Glu Asn Arg Asn Arg Asp Leu Tyr Thr Leu
    50                  55                  60

Gln Thr Leu Gln Asn His Pro Glu Phe Lys Lys Lys Thr Ile Thr Arg
65                  70                  75                  80

Pro Val Val Phe Ile Thr His Gly Phe Thr Ser Ser Ala Ser Glu Thr
                85                  90                  95

Asn Phe Ile Asn Leu Ala Lys Ala Leu Val Asp Lys Asp Asn Tyr Met
            100                 105                 110

Val Ile Ser Ile Asp Trp Gln Thr Ala Ala Cys Thr Asn Glu Ala Ala
        115                 120                 125

Gly Leu Lys Tyr Leu Tyr Tyr Pro Thr Ala Ala Arg Asn Thr Arg Leu
    130                 135                 140

Val Gly Gln Tyr Ile Ala Thr Ile Thr Gln Lys Leu Val Lys His Tyr
145                 150                 155                 160

Lys Ile Ser Met Ala Asn Ile Arg Leu Ile Gly His Ser Leu Gly Ala
                165                 170                 175

His Ala Ser Gly Phe Ala Gly Lys Lys Val Gln Glu Leu Lys Leu Gly
            180                 185                 190

Lys Tyr Ser Glu Ile Ile Gly Leu Asp Pro Ala Arg Pro Ser Phe Asp
        195                 200                 205

Ser Asn His Cys Ser Glu Arg Leu Cys Glu Thr Asp Ala Glu Tyr Val
    210                 215                 220

Gln Ile Ile His Thr Ser Asn Tyr Leu Gly Thr Glu Lys Thr Leu Gly
225                 230                 235                 240

Thr Val Asp Phe Tyr Met Asn Asn Gly Lys Asn Gln Pro Gly Cys Gly
                245                 250                 255

Arg Phe Phe Ser Glu Val Cys Ser His Ser Arg Ala Val Ile Tyr Met
            260                 265                 270
```

Ala Glu Cys Ile Lys His Glu Cys Cys Leu Ile Gly Ile Pro Lys Ser
275 280 285

Lys Ser Ser Gln Pro Ile Ser Ser Cys Thr Lys Gln Glu Cys Val Cys
290 295 300

Val Gly Leu Asn Ala Lys Lys Tyr Pro Ser Arg Gly Ser Phe Tyr Val
305 310 315 320

Pro Val Glu Ser Thr Ala Pro Phe Cys Asn Asn Lys Gly Lys Ile Ile
325 330 335

<210> SEQ ID NO 35
<211> LENGTH: 331
<212> TYPE: PRT
<213> ORGANISM: Vespula vulgaris

<400> SEQUENCE: 35

Ser Glu Arg Pro Lys Arg Val Phe Asn Ile Tyr Trp Asn Val Pro Thr
1 5 10 15

Phe Met Cys His Gln Tyr Asp Leu Tyr Phe Asp Glu Val Thr Asn Phe
20 25 30

Asn Ile Lys Arg Asn Ser Lys Asp Asp Phe Gln Gly Asp Lys Ile Ala
35 40 45

Ile Phe Tyr Asp Pro Gly Glu Phe Pro Ala Leu Leu Ser Leu Lys Asp
50 55 60

Gly Lys Tyr Lys Lys Arg Asn Gly Gly Val Pro Gln Glu Gly Asn Ile
65 70 75 80

Thr Ile His Leu Gln Lys Phe Ile Glu Asn Leu Asp Lys Ile Tyr Pro
85 90 95

Asn Arg Asn Phe Ser Gly Ile Gly Val Ile Asp Phe Glu Arg Trp Arg
100 105 110

Pro Ile Phe Arg Gln Asn Trp Gly Asn Met Lys Ile His Lys Asn Phe
115 120 125

Ser Ile Asp Leu Val Arg Asn Glu His Pro Thr Trp Asn Lys Lys Met
130 135 140

Ile Glu Leu Glu Ala Ser Lys Arg Phe Glu Lys Tyr Ala Arg Phe Phe
145 150 155 160

Met Glu Glu Thr Leu Lys Leu Ala Lys Lys Thr Arg Lys Gln Ala Asp
165 170 175

Trp Gly Tyr Tyr Gly Tyr Pro Tyr Cys Phe Asn Met Ser Pro Asn Asn
180 185 190

Leu Val Pro Glu Cys Asp Val Thr Ala Met His Glu Asn Asp Lys Met
195 200 205

Ser Trp Leu Phe Asn Asn Gln Asn Val Leu Leu Pro Ser Val Tyr Val
210 215 220

Arg Gln Glu Leu Thr Pro Asp Gln Arg Ile Gly Leu Val Gln Gly Arg
225 230 235 240

Val Lys Glu Ala Val Arg Ile Ser Asn Asn Leu Lys His Ser Pro Lys
245 250 255

Val Leu Ser Tyr Trp Trp Tyr Val Tyr Gln Asp Glu Thr Asn Thr Phe
260 265 270

Leu Thr Glu Thr Asp Val Lys Lys Thr Phe Gln Glu Ile Val Ile Asn
275 280 285

Gly Gly Asp Gly Ile Ile Ile Trp Gly Ser Ser Ser Asp Val Asn Ser
290 295 300

Leu Ser Lys Cys Lys Arg Leu Gln Asp Tyr Leu Leu Thr Val Leu Gly
305 310 315 320

```
Pro Ile Ala Ile Asn Val Thr Glu Ala Val Asn
                325                 330


<210> SEQ ID NO 36
<211> LENGTH: 206
<212> TYPE: PRT
<213> ORGANISM: Vespula vulgaris

<400> SEQUENCE: 36

Lys Val Asn Tyr Cys Lys Ile Lys Cys Leu Lys Gly Gly Val His Thr
1               5                   10                  15

Ala Cys Lys Tyr Gly Thr Ser Thr Lys Pro Asn Cys Gly Lys Met Val
            20                  25                  30

Val Lys Ala Tyr Gly Leu Thr Glu Ala Glu Lys Gln Glu Ile Leu Lys
        35                  40                  45

Val His Asn Asp Phe Arg Gln Lys Val Ala Lys Gly Leu Glu Thr Arg
    50                  55                  60

Gly Asn Pro Gly Pro Gln Pro Pro Ala Lys Asn Met Asn Asn Leu Val
65                  70                  75                  80

Trp Asn Asp Glu Leu Ala Asn Ile Ala Gln Val Trp Ala Ser Gln Cys
                85                  90                  95

Asn Tyr Gly His Asp Thr Cys Lys Asp Thr Glu Lys Tyr Pro Val Gly
            100                 105                 110

Gln Asn Ile Ala Lys Arg Ser Thr Thr Ala Ala Leu Phe Asp Ser Pro
        115                 120                 125

Gly Lys Leu Val Lys Met Trp Glu Asn Glu Val Lys Asp Phe Asn Pro
    130                 135                 140

Asn Ile Glu Trp Ser Lys Asn Asn Leu Lys Lys Thr Gly His Tyr Thr
145                 150                 155                 160

Gln Met Val Trp Ala Lys Thr Lys Glu Ile Gly Cys Gly Ser Val Lys
                165                 170                 175

Tyr Val Lys Asp Glu Trp Tyr Thr His Tyr Leu Val Cys Asn Tyr Gly
            180                 185                 190

Pro Ser Gly Asn Phe Arg Asn Glu Lys Leu Tyr Glu Lys Lys
        195                 200                 205


<210> SEQ ID NO 37
<211> LENGTH: 206
<212> TYPE: PRT
<213> ORGANISM: Vespula vidua

<400> SEQUENCE: 37

Lys Val Asn Tyr Cys Lys Ile Lys Cys Leu Lys Gly Gly Val His Thr
1               5                   10                  15

Ala Cys Lys Tyr Gly Thr Ser Thr Lys Pro Asn Cys Gly Lys Met Val
            20                  25                  30

Val Lys Ala Tyr Gly Leu Thr Glu Ala Glu Lys Gln Glu Ile Leu Lys
        35                  40                  45

Val His Asn Asp Phe Arg Gln Lys Val Ala Lys Gly Leu Glu Thr Arg
    50                  55                  60

Gly Asn Pro Gly Pro Gln Pro Pro Ala Lys Asn Met Asn Asn Leu Val
65                  70                  75                  80

Trp Asn Asp Glu Leu Ala Asn Ile Ala Gln Val Trp Ala Ser Gln Cys
                85                  90                  95

Asn Tyr Gly His Asp Thr Cys Lys Asp Thr Glu Lys Tyr Pro Val Gly
            100                 105                 110
```

```
Gln Asn Ile Ala Lys Arg Ser Thr Thr Ala Ala Leu Phe Asp Ser Pro
        115                 120                 125

Gly Lys Leu Val Lys Met Trp Glu Asn Glu Val Lys Asp Phe Asn Pro
    130                 135                 140

Asn Ile Glu Trp Ser Lys Asn Asn Leu Lys Lys Thr Gly His Tyr Thr
145                 150                 155                 160

Gln Met Val Trp Ala Lys Thr Lys Glu Ile Gly Cys Gly Ser Val Lys
                165                 170                 175

Tyr Val Lys Asp Glu Trp Tyr Thr His Tyr Leu Val Cys Asn Tyr Gly
            180                 185                 190

Pro Ser Gly Asn Phe Arg Asn Glu Lys Leu Tyr Glu Lys Lys
        195                 200                 205


<210> SEQ ID NO 38
<211> LENGTH: 160
<212> TYPE: PRT
<213> ORGANISM: Betula pendula

<400> SEQUENCE: 38

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160


<210> SEQ ID NO 39
<211> LENGTH: 133
<212> TYPE: PRT
<213> ORGANISM: Betula pendula

<400> SEQUENCE: 39

Met Ser Trp Gln Thr Tyr Val Asp Glu His Leu Met Cys Asp Ile Asp
1               5                   10                  15

Gly Gln Ala Ser Asn Ser Leu Ala Ser Ala Ile Val Gly His Asp Gly
            20                  25                  30

Ser Val Trp Ala Gln Ser Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80
```

```
Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110

Thr Pro Gly Gln Cys Asn Met Val Val Glu Arg Leu Gly Asp Tyr Leu
        115                 120                 125

Ile Asp Gln Gly Leu
    130


<210> SEQ ID NO 40
<211> LENGTH: 205
<212> TYPE: PRT
<213> ORGANISM: Betula pendula

<400> SEQUENCE: 40

Met Pro Cys Ser Thr Glu Ala Met Glu Lys Ala Gly His Gly His Ala
1               5                   10                  15

Ser Thr Pro Arg Lys Arg Ser Leu Ser Asn Ser Ser Phe Arg Leu Arg
            20                  25                  30

Ser Glu Ser Leu Asn Thr Leu Arg Leu Arg Arg Ile Phe Asp Leu Phe
        35                  40                  45

Asp Lys Asn Ser Asp Gly Ile Ile Thr Val Asp Glu Leu Ser Arg Ala
    50                  55                  60

Leu Asn Leu Leu Gly Leu Glu Thr Asp Leu Ser Glu Leu Glu Ser Thr
65                  70                  75                  80

Val Lys Ser Phe Thr Arg Glu Gly Asn Ile Gly Leu Gln Phe Glu Asp
                85                  90                  95

Phe Ile Ser Leu His Gln Ser Leu Asn Asp Ser Tyr Phe Ala Tyr Gly
            100                 105                 110

Gly Glu Asp Glu Asp Asp Asn Glu Glu Asp Met Arg Lys Ser Ile Leu
        115                 120                 125

Ser Gln Glu Glu Ala Asp Ser Phe Gly Gly Phe Lys Val Phe Asp Glu
    130                 135                 140

Asp Gly Asp Gly Tyr Ile Ser Ala Arg Glu Leu Gln Met Val Leu Gly
145                 150                 155                 160

Lys Leu Gly Phe Ser Glu Gly Ser Glu Ile Asp Arg Val Glu Lys Met
                165                 170                 175

Ile Val Ser Val Asp Ser Asn Arg Asp Gly Arg Val Asp Phe Phe Glu
            180                 185                 190

Phe Lys Asp Met Met Arg Ser Val Leu Val Arg Ser Ser
        195                 200                 205


<210> SEQ ID NO 41
<211> LENGTH: 85
<212> TYPE: PRT
<213> ORGANISM: Betula pendula

<400> SEQUENCE: 41

Met Ala Asp Asp His Pro Gln Asp Lys Ala Glu Arg Glu Arg Ile Phe
1               5                   10                  15

Lys Arg Phe Asp Ala Asn Gly Asp Gly Lys Ile Ser Ala Ala Glu Leu
            20                  25                  30

Gly Glu Ala Leu Lys Thr Leu Gly Ser Ile Thr Pro Asp Glu Val Lys
        35                  40                  45

His Met Met Ala Glu Ile Asp Thr Asp Gly Asp Gly Phe Ile Ser Phe
    50                  55                  60
```

```
Gln Glu Phe Thr Asp Phe Gly Arg Ala Asn Arg Gly Leu Leu Lys Asp
65                  70                  75                  80

Val Ala Lys Ile Phe
                85


<210> SEQ ID NO 42
<211> LENGTH: 24
<212> TYPE: PRT
<213> ORGANISM: Quercus alba
<220> FEATURE:
<221> NAME/KEY: MOD_RES
<222> LOCATION: (5)..(5)
<223> OTHER INFORMATION: Any naturally occurring amino acid
<220> FEATURE:
<221> NAME/KEY: MOD_RES
<222> LOCATION: (17)..(17)
<223> OTHER INFORMATION: Any naturally occurring amino acid

<400> SEQUENCE: 42

Gly Val Phe Thr Xaa Glu Ser Gln Glu Thr Ser Val Ile Ala Pro Ala
1               5                   10                  15

Xaa Leu Phe Lys Ala Leu Phe Leu
            20


<210> SEQ ID NO 43
<211> LENGTH: 40
<212> TYPE: PRT
<213> ORGANISM: Carpinus betulus
<220> FEATURE:
<221> NAME/KEY: MOD_RES
<222> LOCATION: (39)..(39)
<223> OTHER INFORMATION: Any naturally occurring amino acid

<400> SEQUENCE: 43

Gly Val Phe Asn Tyr Glu Ala Glu Thr Pro Ser Val Ile Pro Ala Ala
1               5                   10                  15

Arg Leu Phe Lys Ser Tyr Val Leu Asp Gly Asp Lys Leu Ile Pro Lys
            20                  25                  30

Val Ala Pro Gln Ala Ile Xaa Lys
        35                  40


<210> SEQ ID NO 44
<211> LENGTH: 44
<212> TYPE: PRT
<213> ORGANISM: Alnus glutinosa

<400> SEQUENCE: 44

Gly Val Phe Asn Tyr Glu Ala Glu Thr Pro Ser Val Ile Pro Ala Ala
1               5                   10                  15

Arg Leu Phe Lys Ala Phe Ile Leu Asp Gly Asp Lys Leu Leu Pro Lys
            20                  25                  30

Val Ala Pro Glu Ala Val Ser Ser Val Glu Asn Ile
        35                  40


<210> SEQ ID NO 45
<211> LENGTH: 110
<212> TYPE: PRT
<213> ORGANISM: Betula pendula

<400> SEQUENCE: 45

Val Gln Cys Met Gln Val Trp Pro Pro Leu Gly Leu Lys Lys Phe Glu
1               5                   10                  15

Thr Leu Ser Tyr Leu Pro Pro Leu Ser Ser Glu Gln Leu Ala Lys Glu
```

```
            20                  25                  30

Val Asp Tyr Leu Leu Arg Lys Asn Leu Ile Pro Cys Leu Glu Phe Glu
        35                  40                  45

Leu Glu His Gly Phe Val Tyr Arg Glu His Asn Arg Ser Pro Gly Tyr
    50                  55                  60

Tyr Asp Gly Arg Tyr Trp Thr Met Trp Lys Leu Pro Met Phe Gly Cys
65                  70                  75                  80

Asn Asp Ser Ser Gln Val Leu Lys Glu Leu Glu Glu Cys Lys Lys Ala
                85                  90                  95

Tyr Pro Ser Ala Phe Ile Arg Ile Ile Gly Phe Asp Asp Lys
            100                 105                 110


<210> SEQ ID NO 46
<211> LENGTH: 373
<212> TYPE: PRT
<213> ORGANISM: Cryptomeria japonica

<400> SEQUENCE: 46

Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Asp Pro Val Asn Pro Pro Gly Thr Leu Arg Tyr
65                  70                  75                  80

Gly Ala Thr Arg Asp Arg Pro Leu Trp Ile Ile Phe Ser Gly Asn Met
                85                  90                  95

Asn Ile Lys Leu Lys Met Pro Met Tyr Ile Ala Gly Tyr Lys Thr Phe
            100                 105                 110

Asp Gly Arg Gly Ala Gln Val Tyr Ile Gly Asn Gly Gly Pro Cys Val
        115                 120                 125

Phe Ile Lys Arg Val Ser Asn Val Ile Ile His Gly Leu Tyr Leu Tyr
    130                 135                 140

Gly Cys Ser Thr Ser Val Leu Gly Asn Val Leu Ile Asn Glu Ser Phe
145                 150                 155                 160

Gly Val Glu Pro Val His Pro Gln Asp Gly Asp Ala Leu Thr Leu Arg
                165                 170                 175

Thr Ala Thr Asn Ile Trp Ile Asp His Asn Ser Phe Ser Asn Ser Ser
            180                 185                 190

Asp Gly Leu Val Asp Val Thr Leu Thr Ser Thr Gly Val Thr Ile Ser
        195                 200                 205

Asn Asn Leu Phe Phe Asn His His Lys Val Met Ser Leu Gly His Asp
    210                 215                 220

Asp Ala Tyr Ser Asp Asp Lys Ser Met Lys Val Thr Val Ala Phe Asn
225                 230                 235                 240

Gln Phe Gly Pro Asn Cys Gly Gln Arg Met Pro Arg Ala Arg Tyr Gly
                245                 250                 255

Leu Val His Val Ala Asn Asn Asn Tyr Asp Pro Trp Thr Ile Tyr Ala
            260                 265                 270

Ile Gly Gly Ser Ser Asn Pro Thr Ile Leu Ser Glu Gly Asn Ser Phe
        275                 280                 285
```

-continued

```
Thr Ala Pro Asn Glu Ser Tyr Lys Lys Gln Val Thr Ile Arg Ile Gly
    290                 295                 300

Cys Lys Thr Ser Ser Ser Cys Ser Asn Trp Val Trp Gln Ser Thr Gln
305                 310                 315                 320

Asp Val Phe Tyr Asn Gly Ala Tyr Phe Val Ser Ser Gly Lys Tyr Glu
                325                 330                 335

Gly Gly Asn Ile Tyr Thr Lys Lys Glu Ala Phe Asn Val Glu Asn Gly
            340                 345                 350

Asn Ala Thr Pro His Leu Thr Gln Asn Ala Gly Val Leu Thr Cys Ser
        355                 360                 365

Leu Ser Lys Arg Cys
    370


<210> SEQ ID NO 47
<211> LENGTH: 374
<212> TYPE: PRT
<213> ORGANISM: Cryptomeria japonica

<400> SEQUENCE: 47

Met Asp Ser Pro Cys Leu Val Ala Leu Leu Val Leu Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Asp Pro Val Asn Pro Ala Pro Gly Thr Leu Arg
65                  70                  75                  80

Tyr Gly Ala Thr Arg Asp Arg Pro Leu Trp Ile Ile Phe Ser Gly Asn
                85                  90                  95

Met Asn Ile Lys Leu Lys Met Pro Met Tyr Ile Ala Gly Tyr Lys Thr
            100                 105                 110

Phe Asp Gly Arg Gly Ala Gln Val Tyr Ile Gly Asn Gly Gly Pro Cys
        115                 120                 125

Val Phe Ile Lys Arg Val Ser Asn Val Ile Ile His Gly Leu His Leu
    130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
            180                 185                 190

Ser Asp Gly Leu Val Asp Val Thr Leu Ser Ser Thr Gly Val Thr Ile
        195                 200                 205

Ser Asn Asn Leu Phe Phe Asn His His Lys Val Met Leu Leu Gly His
    210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
                245                 250                 255

Gly Leu Val His Val Ala Asn Asn Asn Tyr Asp Pro Trp Thr Ile Tyr
            260                 265                 270

Ala Ile Gly Gly Ser Ser Asn Pro Thr Ile Leu Ser Glu Gly Asn Ser
        275                 280                 285
```

```
Phe Thr Ala Pro Asn Glu Ser Tyr Lys Lys Gln Val Thr Ile Arg Ile
    290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
                325                 330                 335

Glu Gly Gly Asn Ile Tyr Thr Lys Lys Glu Ala Phe Asn Val Glu Asn
            340                 345                 350

Gly Asn Ala Thr Pro Gln Leu Thr Lys Asn Ala Gly Val Leu Thr Cys
        355                 360                 365

Ser Leu Ser Lys Arg Cys
    370


<210> SEQ ID NO 48
<211> LENGTH: 514
<212> TYPE: PRT
<213> ORGANISM: Cryptomeria japonica

<400> SEQUENCE: 48

Met Ala Met Lys Leu Ile Ala Pro Met Ala Phe Leu Ala Met Gln Leu
1               5                   10                  15

Ile Ile Met Ala Ala Ala Glu Asp Gln Ser Ala Gln Ile Met Leu Asp
            20                  25                  30

Ser Val Val Glu Lys Tyr Leu Arg Ser Asn Arg Ser Leu Arg Lys Val
        35                  40                  45

Glu His Ser Arg His Asp Ala Ile Asn Ile Phe Asn Val Glu Lys Tyr
    50                  55                  60

Gly Ala Val Gly Asp Gly Lys His Asp Cys Thr Glu Ala Phe Ser Thr
65                  70                  75                  80

Ala Trp Gln Ala Ala Cys Lys Asn Pro Ser Ala Met Leu Leu Val Pro
                85                  90                  95

Gly Ser Lys Lys Phe Val Val Asn Asn Leu Phe Phe Asn Gly Pro Cys
            100                 105                 110

Gln Pro His Phe Thr Phe Lys Val Asp Gly Ile Ile Ala Ala Tyr Gln
        115                 120                 125

Asn Pro Ala Ser Trp Lys Asn Asn Arg Ile Trp Leu Gln Phe Ala Lys
    130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
        195                 200                 205

Leu Val Phe Gly Asn Cys Glu Gly Val Lys Ile Ile Gly Ile Ser Ile
    210                 215                 220

Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
            260                 265                 270

Ile Cys Gly Pro Gly His Gly Ile Ser Ile Gly Ser Leu Gly Arg Glu
```

```
        275                 280                 285

Asn Ser Arg Ala Glu Val Ser Tyr Val His Val Asn Gly Ala Lys Phe
    290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350

Cys Gln Asn Gln Arg Ser Ala Val Gln Ile Gln Asp Val Thr Tyr Lys
        355                 360                 365

Asn Ile Arg Gly Thr Ser Ala Thr Ala Ala Ala Ile Gln Leu Lys Cys
    370                 375                 380

Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
                405                 410                 415

Gly Tyr Phe Ser Gly His Val Ile Pro Ala Cys Lys Asn Leu Ser Pro
            420                 425                 430

Ser Ala Lys Arg Lys Glu Ser Lys Ser His Lys His Pro Lys Thr Val
        435                 440                 445

Met Val Glu Asn Met Arg Ala Tyr Asp Lys Gly Asn Arg Thr Arg Ile
    450                 455                 460

Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Ile Cys Ser Cys His Gly Lys Ile Tyr
            500                 505                 510

His Pro


<210> SEQ ID NO 49
<211> LENGTH: 514
<212> TYPE: PRT
<213> ORGANISM: Cryptomeria japonica

<400> SEQUENCE: 49

Met Ala Met Lys Phe Ile Ala Pro Met Ala Phe Val Ala Met Gln Leu
1               5                   10                  15

Ile Ile Met Ala Ala Ala Glu Asp Gln Ser Ala Gln Ile Met Leu Asp
            20                  25                  30

Ser Asp Ile Glu Gln Tyr Leu Arg Ser Asn Arg Ser Leu Arg Lys Val
        35                  40                  45

Glu His Ser Arg His Asp Ala Ile Asn Ile Phe Asn Val Glu Lys Tyr
    50                  55                  60

Gly Ala Val Gly Asp Gly Lys His Asp Cys Thr Glu Ala Phe Ser Thr
65                  70                  75                  80

Ala Trp Gln Ala Ala Cys Lys Lys Pro Ser Ala Met Leu Leu Val Pro
                85                  90                  95

Gly Asn Lys Lys Phe Val Val Asn Asn Leu Phe Phe Asn Gly Pro Cys
            100                 105                 110

Gln Pro His Phe Thr Phe Lys Val Asp Gly Ile Ile Ala Ala Tyr Gln
        115                 120                 125

Asn Pro Ala Ser Trp Lys Asn Asn Arg Ile Trp Leu Gln Phe Ala Lys
```

```
    130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
        195                 200                 205

Leu Val Phe Gly Asn Cys Glu Gly Val Lys Ile Ile Gly Ile Ser Ile
    210                 215                 220

Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
            260                 265                 270

Ile Cys Gly Pro Gly His Gly Ile Ser Ile Gly Ser Leu Gly Arg Glu
        275                 280                 285

Asn Ser Arg Ala Glu Val Ser Tyr Val His Val Asn Gly Ala Lys Phe
    290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350

Cys Gln Asn Gln Arg Ser Ala Val Gln Ile Gln Asp Val Thr Tyr Lys
        355                 360                 365

Asn Ile Arg Gly Thr Ser Ala Thr Ala Ala Ala Ile Gln Leu Lys Cys
    370                 375                 380

Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
                405                 410                 415

Gly Tyr Phe Ser Gly His Val Ile Pro Ala Cys Lys Asn Leu Ser Pro
            420                 425                 430

Ser Ala Lys Arg Lys Glu Ser Lys Ser His Lys His Pro Lys Thr Val
        435                 440                 445

Met Val Lys Asn Met Gly Ala Tyr Asp Lys Gly Asn Arg Thr Arg Ile
    450                 455                 460

Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Met Cys Ser Arg His Gly Lys Ile Tyr
            500                 505                 510

His Pro
```

<210> SEQ ID NO 50
<211> LENGTH: 373
<212> TYPE: PRT
<213> ORGANISM: Cryptomeria japonica

<400> SEQUENCE: 50

Met Asp Ser Pro Cys Leu Val Ala Leu Leu Val Leu Ser Phe Val Ile
1 5 10 15

Gly Ser Cys Phe Ser Asp Asn Pro Ile Asp Ser Cys Trp Arg Gly Asp
20 25 30

Ser Asn Trp Ala Gln Asn Arg Met Lys Leu Ala Asp Cys Ala Val Gly
35 40 45

Phe Gly Ser Ser Thr Met Gly Gly Lys Gly Gly Asp Leu Tyr Thr Val
50 55 60

Thr Asn Ser Asp Asp Asp Pro Val Asn Pro Pro Gly Thr Leu Arg Tyr
65 70 75 80

Gly Ala Thr Arg Asp Arg Pro Leu Trp Ile Ile Phe Ser Gly Asn Met
85 90 95

Asn Ile Lys Leu Lys Met Pro Met Tyr Ile Ala Gly Tyr Lys Thr Phe
100 105 110

Asp Gly Arg Gly Ala Gln Val Tyr Ile Gly Asn Gly Gly Pro Cys Val
115 120 125

Phe Ile Lys Arg Val Ser Asn Val Ile Ile His Gly Leu His Leu Tyr
130 135 140

Gly Cys Ser Thr Ser Val Leu Gly Asn Val Leu Ile Asn Glu Ser Phe
145 150 155 160

Gly Val Glu Pro Val His Pro Gln Asp Gly Asp Ala Leu Thr Leu Arg
165 170 175

Thr Ala Thr Asn Ile Trp Ile Asp His Asn Ser Phe Ser Asn Ser Ser
180 185 190

Asp Gly Leu Val Asp Val Thr Leu Ser Ser Thr Gly Val Thr Ile Ser
195 200 205

Asn Asn Leu Phe Phe Asn His His Lys Val Met Leu Leu Gly His Asp
210 215 220

Asp Ala Tyr Ser Asp Asp Lys Ser Met Lys Val Thr Val Ala Phe Asn
225 230 235 240

Gln Phe Gly Pro Asn Cys Gly Gln Arg Met Pro Arg Ala Arg Tyr Gly
245 250 255

Leu Val His Val Ala Asn Asn Asn Tyr Asp Pro Trp Thr Ile Tyr Ala
260 265 270

Ile Gly Gly Ser Ser Asn Pro Thr Ile Leu Ser Glu Gly Asn Ser Phe
275 280 285

Thr Ala Pro Asn Glu Ser Tyr Lys Lys Gln Val Thr Ile Arg Ile Gly
290 295 300

Cys Lys Thr Ser Ser Ser Cys Ser Asn Trp Val Trp Gln Ser Thr Gln
305 310 315 320

Asp Val Phe Tyr Asn Gly Ala Tyr Phe Val Ser Ser Gly Lys Tyr Glu
325 330 335

Gly Gly Asn Ile Tyr Thr Lys Lys Glu Ala Phe Asn Val Glu Asn Gly
340 345 350

Asn Ala Thr Pro Gln Leu Thr Lys Asn Ala Gly Val Leu Thr Cys Ser
355 360 365

Leu Ser Lys Arg Cys
370

<210> SEQ ID NO 51
<211> LENGTH: 374
<212> TYPE: PRT
<213> ORGANISM: Cryptomeria japonica

<400> SEQUENCE: 51

Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
            20                  25                  30

Ser Asn Trp Ala Gln Asn Arg Met Lys Leu Ala Asp Cys Ala Val Gly
        35                  40                  45

Phe Gly Ser Ser Thr Met Gly Gly Lys Gly Gly Asp Leu Tyr Thr Val
    50                  55                  60

Thr Asn Ser Asp Asp Asp Pro Val Asn Pro Ala Pro Gly Thr Leu Arg
65                  70                  75                  80

Tyr Gly Ala Thr Arg Asp Arg Pro Leu Trp Ile Ile Phe Ser Gly Asn
                85                  90                  95

Met Asn Ile Lys Leu Lys Met Pro Met Tyr Ile Ala Gly Tyr Lys Thr
            100                 105                 110

Phe Asp Gly Arg Gly Ala Gln Val Tyr Ile Gly Asn Gly Gly Pro Cys
        115                 120                 125

Val Phe Ile Lys Arg Val Ser Asn Val Ile Ile His Gly Leu Tyr Leu
    130                 135                 140

Tyr Gly Cys Ser Thr Ser Val Leu Gly Asn Val Leu Ile Asn Glu Ser
145                 150                 155                 160

Phe Gly Val Glu Pro Val His Pro Gln Asp Gly Asp Ala Leu Thr Leu
                165                 170                 175

Arg Thr Ala Thr Asn Ile Trp Ile Asp His Asn Ser Phe Ser Asn Ser
            180                 185                 190

Ser Asp Gly Leu Val Asp Val Thr Leu Thr Ser Thr Gly Val Thr Ile
        195                 200                 205

Ser Asn Asn Leu Phe Phe Asn His His Lys Val Met Ser Leu Gly His
    210                 215                 220

Asp Asp Ala Tyr Ser Asp Asp Lys Ser Met Lys Val Thr Val Ala Phe
225                 230                 235                 240

Asn Gln Phe Gly Pro Asn Cys Gly Gln Arg Met Pro Arg Ala Arg Tyr
                245                 250                 255

Gly Leu Val His Val Ala Asn Asn Asn Tyr Asp Pro Trp Thr Ile Tyr
            260                 265                 270

Ala Ile Gly Gly Ser Ser Asn Pro Thr Ile Leu Ser Glu Gly Asn Ser
        275                 280                 285

Phe Thr Ala Pro Asn Glu Ser Tyr Lys Lys Gln Val Thr Ile Arg Ile
    290                 295                 300

Gly Cys Lys Thr Ser Ser Ser Cys Ser Asn Trp Val Trp Gln Ser Thr
305                 310                 315                 320

Gln Asp Val Phe Tyr Asn Gly Ala Tyr Phe Val Ser Ser Gly Lys Tyr
                325                 330                 335

Glu Gly Gly Asn Ile Tyr Thr Lys Lys Glu Ala Phe Asn Val Glu Asn
            340                 345                 350

Gly Asn Ala Thr Pro His Leu Thr Gln Asn Ala Gly Val Leu Thr Cys
        355                 360                 365

Ser Leu Ser Lys Arg Cys
    370

<210> SEQ ID NO 52
<211> LENGTH: 145
<212> TYPE: PRT

<213> ORGANISM: Olea europaea

<400> SEQUENCE: 52

Glu Asp Ile Pro Gln Pro Pro Val Ser Gln Phe His Ile Gln Gly Gln
1 5 10 15

Val Tyr Cys Asp Thr Cys Arg Ala Gly Phe Ile Thr Glu Leu Ser Glu
20 25 30

Phe Ile Pro Gly Ala Ser Leu Arg Leu Gln Cys Lys Asp Lys Glu Asn
35 40 45

Gly Asp Val Thr Phe Thr Glu Val Gly Tyr Thr Arg Ala Glu Gly Leu
50 55 60

Tyr Ser Met Leu Val Glu Arg Asp His Lys Asn Glu Phe Cys Glu Ile
65 70 75 80

Thr Leu Ile Ser Ser Gly Arg Lys Asp Cys Asn Glu Ile Pro Thr Glu
85 90 95

Gly Trp Ala Lys Pro Ser Leu Lys Phe Lys Leu Asn Thr Val Asn Gly
100 105 110

Thr Thr Arg Thr Val Asn Pro Leu Gly Phe Phe Lys Lys Glu Ala Leu
115 120 125

Pro Lys Cys Ala Gln Val Tyr Asn Lys Leu Gly Met Tyr Pro Pro Asn
130 135 140

Met
145

<210> SEQ ID NO 53
<211> LENGTH: 626
<212> TYPE: PRT
<213> ORGANISM: Arachis hypogaea

<400> SEQUENCE: 53

Met Arg Gly Arg Val Ser Pro Leu Met Leu Leu Leu Gly Ile Leu Val
1 5 10 15

Leu Ala Ser Val Ser Ala Thr His Ala Lys Ser Ser Pro Tyr Gln Lys
20 25 30

Lys Thr Glu Asn Pro Cys Ala Gln Arg Cys Leu Gln Ser Cys Gln Gln
35 40 45

Glu Pro Asp Asp Leu Lys Gln Lys Ala Cys Glu Ser Arg Cys Thr Lys
50 55 60

Leu Glu Tyr Asp Pro Arg Cys Val Tyr Asp Pro Arg Gly His Thr Gly
65 70 75 80

Thr Thr Asn Gln Arg Ser Pro Pro Gly Glu Arg Thr Arg Gly Arg Gln
85 90 95

Pro Gly Asp Tyr Asp Asp Asp Arg Arg Gln Pro Arg Arg Glu Glu Gly
100 105 110

Gly Arg Trp Gly Pro Ala Gly Pro Arg Glu Arg Glu Arg Glu Glu Asp
115 120 125

Trp Arg Gln Pro Arg Glu Asp Trp Arg Arg Pro Ser His Gln Gln Pro
130 135 140

Arg Lys Ile Arg Pro Glu Gly Arg Glu Gly Glu Gln Glu Trp Gly Thr
145 150 155 160

Pro Gly Ser His Val Arg Glu Glu Thr Ser Arg Asn Asn Pro Phe Tyr
165 170 175

Phe Pro Ser Arg Arg Phe Ser Thr Arg Tyr Gly Asn Gln Asn Gly Arg
180 185 190

Ile Arg Val Leu Gln Arg Phe Asp Gln Arg Ser Arg Gln Phe Gln Asn

-continued

```
        195                 200                 205

Leu Gln Asn His Arg Ile Val Gln Ile Glu Ala Lys Pro Asn Thr Leu
    210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
        275                 280                 285

Ser Met Pro Val Asn Thr Pro Gly Gln Phe Glu Asp Phe Phe Pro Ala
    290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Glu Gln Glu Glu Arg Gly Gln Arg Arg
            340                 345                 350

Trp Ser Thr Arg Ser Ser Glu Asn Asn Glu Gly Val Ile Val Lys Val
        355                 360                 365

Ser Lys Glu His Val Glu Glu Leu Thr Lys His Ala Lys Ser Val Ser
    370                 375                 380

Lys Lys Gly Ser Glu Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415

Val Lys Pro Asp Lys Lys Asn Pro Gln Leu Gln Asp Leu Asp Met Met
            420                 425                 430

Leu Thr Cys Val Glu Ile Lys Glu Gly Ala Leu Met Leu Pro His Phe
        435                 440                 445

Asn Ser Lys Ala Met Val Ile Val Val Val Asn Lys Gly Thr Gly Asn
    450                 455                 460

Leu Glu Leu Val Ala Val Arg Lys Glu Gln Gln Gln Arg Gly Arg Arg
465                 470                 475                 480

Glu Glu Glu Glu Asp Glu Asp Glu Glu Glu Glu Gly Ser Asn Arg Glu
                485                 490                 495

Val Arg Arg Tyr Thr Ala Arg Leu Lys Glu Gly Asp Val Phe Ile Met
            500                 505                 510

Pro Ala Ala His Pro Val Ala Ile Asn Ala Ser Ser Glu Leu His Leu
        515                 520                 525

Leu Gly Phe Gly Ile Asn Ala Glu Asn Asn His Arg Ile Phe Leu Ala
    530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Glu Lys Leu Ile Lys Asn
                565                 570                 575

Gln Lys Glu Ser His Phe Val Ser Ala Arg Pro Gln Ser Gln Ser Gln
            580                 585                 590

Ser Pro Ser Ser Pro Glu Lys Glu Ser Pro Glu Lys Glu Asp Gln Glu
        595                 600                 605

Glu Glu Asn Gln Gly Gly Lys Gly Pro Leu Leu Ser Ile Leu Lys Ala
    610                 615                 620
```

Phe Asn
625

<210> SEQ ID NO 54
<211> LENGTH: 392
<212> TYPE: PRT
<213> ORGANISM: Ambrosia artemisiifolia

<400> SEQUENCE: 54

Met Gly Ile Lys His Cys Cys Tyr Ile Leu Tyr Phe Thr Leu Ala Leu
1 5 10 15

Val Thr Leu Leu Gln Pro Val Arg Ser Ala Glu Asp Leu Gln Gln Ile
20 25 30

Leu Pro Ser Ala Asn Glu Thr Arg Ser Leu Thr Thr Cys Gly Thr Tyr
35 40 45

Asn Ile Ile Asp Gly Cys Trp Arg Gly Lys Ala Asp Trp Ala Glu Asn
50 55 60

Arg Lys Ala Leu Ala Asp Cys Ala Gln Gly Phe Ala Lys Gly Thr Ile
65 70 75 80

Gly Gly Lys Asp Gly Asp Ile Tyr Thr Val Thr Ser Glu Leu Asp Asp
85 90 95

Asp Val Ala Asn Pro Lys Glu Gly Thr Leu Arg Phe Gly Ala Ala Gln
100 105 110

Asn Arg Pro Leu Trp Ile Ile Phe Ala Arg Asp Met Val Ile Arg Leu
115 120 125

Asp Arg Glu Leu Ala Ile Asn Asn Asp Lys Thr Ile Asp Gly Arg Gly
130 135 140

Ala Lys Val Glu Ile Ile Asn Ala Gly Phe Ala Ile Tyr Asn Val Lys
145 150 155 160

Asn Ile Ile Ile His Asn Ile Ile Met His Asp Ile Val Val Asn Pro
165 170 175

Gly Gly Leu Ile Lys Ser His Asp Gly Pro Pro Val Pro Arg Lys Gly
180 185 190

Ser Asp Gly Asp Ala Ile Gly Ile Ser Gly Gly Ser Gln Ile Trp Ile
195 200 205

Asp His Cys Ser Leu Ser Lys Ala Val Asp Gly Leu Ile Asp Ala Lys
210 215 220

His Gly Ser Thr His Phe Thr Val Ser Asn Cys Leu Phe Thr Gln His
225 230 235 240

Gln Tyr Leu Leu Leu Phe Trp Asp Phe Asp Glu Arg Gly Met Leu Cys
245 250 255

Thr Val Ala Phe Asn Lys Phe Thr Asp Asn Val Asp Gln Arg Met Pro
260 265 270

Asn Leu Arg His Gly Phe Val Gln Val Val Asn Asn Asn Tyr Glu Arg
275 280 285

Trp Gly Ser Tyr Ala Leu Gly Gly Ser Ala Gly Pro Thr Ile Leu Ser
290 295 300

Gln Gly Asn Arg Phe Leu Ala Ser Asp Ile Lys Lys Glu Val Val Gly
305 310 315 320

Arg Tyr Gly Glu Ser Ala Met Ser Glu Ser Ile Asn Trp Asn Trp Arg
325 330 335

Ser Tyr Met Asp Val Phe Glu Asn Gly Ala Ile Phe Val Pro Ser Gly
340 345 350

Val Asp Pro Val Leu Thr Pro Glu Gln Asn Ala Gly Met Ile Pro Ala

```
        355                 360                 365

Glu Pro Gly Glu Ala Val Leu Arg Leu Thr Ser Ser Ala Gly Val Leu
    370                 375                 380

Ser Cys Gln Pro Gly Ala Pro Cys
385                 390


<210> SEQ ID NO 55
<211> LENGTH: 397
<212> TYPE: PRT
<213> ORGANISM: Ambrosia artemisiifolia

<400> SEQUENCE: 55

Met Gly Ile Lys His Cys Cys Tyr Ile Leu Tyr Phe Thr Leu Ala Leu
1               5                   10                  15

Val Thr Leu Val Gln Ala Gly Arg Leu Gly Glu Glu Val Asp Ile Leu
            20                  25                  30

Pro Ser Pro Asn Asp Thr Arg Arg Ser Leu Gln Gly Cys Glu Ala His
        35                  40                  45

Asn Ile Ile Asp Lys Cys Trp Arg Cys Lys Pro Asp Trp Ala Glu Asn
    50                  55                  60

Arg Gln Ala Leu Gly Asn Cys Ala Gln Gly Phe Gly Lys Ala Thr His
65                  70                  75                  80

Gly Gly Lys Trp Gly Asp Ile Tyr Met Val Thr Ser Asp Gln Asp Asp
                85                  90                  95

Asp Val Val Asn Pro Lys Glu Gly Thr Leu Arg Phe Gly Ala Thr Gln
            100                 105                 110

Asp Arg Pro Leu Trp Ile Ile Phe Gln Arg Asp Met Ile Ile Tyr Leu
        115                 120                 125

Gln Gln Glu Met Val Val Thr Ser Asp Lys Thr Ile Asp Gly Arg Gly
    130                 135                 140

Ala Lys Val Glu Leu Val Tyr Gly Gly Ile Thr Leu Met Asn Val Lys
145                 150                 155                 160

Asn Val Ile Ile His Asn Ile Asp Ile His Asp Val Arg Val Leu Pro
                165                 170                 175

Gly Gly Arg Ile Lys Ser Asn Gly Gly Pro Ala Ile Pro Arg His Gln
            180                 185                 190

Ser Asp Gly Asp Ala Ile His Val Thr Gly Ser Ser Asp Ile Trp Ile
        195                 200                 205

Asp His Cys Thr Leu Ser Lys Ser Phe Asp Gly Leu Val Asp Val Asn
    210                 215                 220

Trp Gly Ser Thr Gly Val Thr Ile Ser Asn Cys Lys Phe Thr His His
225                 230                 235                 240

Glu Lys Ala Val Leu Leu Gly Ala Ser Asp Thr His Phe Gln Asp Leu
                245                 250                 255

Lys Met His Val Thr Leu Ala Tyr Asn Ile Phe Thr Asn Thr Val His
            260                 265                 270

Glu Arg Met Pro Arg Cys Arg Phe Gly Phe Phe Gln Ile Val Asn Asn
        275                 280                 285

Phe Tyr Asp Arg Trp Asp Lys Tyr Ala Ile Gly Gly Ser Ser Asn Pro
    290                 295                 300

Thr Ile Leu Ser Gln Gly Asn Lys Phe Val Ala Pro Asp Phe Ile Tyr
305                 310                 315                 320

Lys Lys Asn Val Cys Leu Arg Thr Gly Ala Gln Glu Pro Glu Trp Met
                325                 330                 335
```

-continued

```
Thr Trp Asn Trp Arg Thr Gln Asn Asp Val Leu Glu Asn Gly Ala Ile
            340                 345                 350

Phe Val Ala Ser Gly Ser Asp Pro Val Leu Thr Ala Glu Gln Asn Ala
        355                 360                 365

Gly Met Met Gln Ala Glu Pro Gly Asp Met Val Pro Gln Leu Thr Met
    370                 375                 380

Asn Ala Gly Val Leu Thr Cys Ser Pro Gly Ala Pro Cys
385                 390                 395


<210> SEQ ID NO 56
<211> LENGTH: 397
<212> TYPE: PRT
<213> ORGANISM: Ambrosia artemisiifolia

<400> SEQUENCE: 56

Met Gly Ile Lys Gln Cys Cys Tyr Ile Leu Tyr Phe Thr Leu Ala Leu
1               5                   10                  15

Val Ala Leu Leu Gln Pro Val Arg Ser Ala Glu Gly Val Gly Glu Ile
            20                  25                  30

Leu Pro Ser Val Asn Glu Thr Arg Ser Leu Gln Ala Cys Glu Ala Leu
        35                  40                  45

Asn Ile Ile Asp Lys Cys Trp Arg Gly Lys Ala Asp Trp Glu Asn Asn
    50                  55                  60

Arg Gln Ala Leu Ala Asp Cys Ala Gln Gly Phe Ala Lys Gly Thr Tyr
65                  70                  75                  80

Gly Gly Lys Trp Gly Asp Val Tyr Thr Val Thr Ser Asn Leu Asp Asp
                85                  90                  95

Asp Val Ala Asn Pro Lys Glu Gly Thr Leu Arg Phe Ala Ala Ala Gln
            100                 105                 110

Asn Arg Pro Leu Trp Ile Ile Phe Lys Asn Asp Met Val Ile Asn Leu
        115                 120                 125

Asn Gln Glu Leu Val Val Asn Ser Asp Lys Thr Ile Asp Gly Arg Gly
    130                 135                 140

Val Lys Val Glu Ile Ile Asn Gly Gly Leu Thr Leu Met Asn Val Lys
145                 150                 155                 160

Asn Ile Ile Ile His Asn Ile Asn Ile His Asp Val Lys Val Leu Pro
                165                 170                 175

Gly Gly Met Ile Lys Ser Asn Asp Gly Pro Pro Ile Leu Arg Gln Ala
            180                 185                 190

Ser Asp Gly Asp Thr Ile Asn Val Ala Gly Ser Ser Gln Ile Trp Ile
        195                 200                 205

Asp His Cys Ser Leu Ser Lys Ser Phe Asp Gly Leu Val Asp Val Thr
    210                 215                 220

Leu Gly Ser Thr His Val Thr Ile Ser Asn Cys Lys Phe Thr Gln Gln
225                 230                 235                 240

Ser Lys Ala Ile Leu Leu Gly Ala Asp Asp Thr His Val Gln Asp Lys
                245                 250                 255

Gly Met Leu Ala Thr Val Ala Phe Asn Met Phe Thr Asp Asn Val Asp
            260                 265                 270

Gln Arg Met Pro Arg Cys Arg Phe Gly Phe Phe Gln Val Val Asn Asn
        275                 280                 285

Asn Tyr Asp Arg Trp Gly Thr Tyr Ala Ile Gly Gly Ser Ser Ala Pro
    290                 295                 300

Thr Ile Leu Cys Gln Gly Asn Arg Phe Leu Ala Pro Asp Asp Gln Ile
305                 310                 315                 320
```

```
Lys Lys Asn Val Leu Ala Arg Thr Gly Thr Gly Ala Ala Glu Ser Met
                325                 330                 335

Ala Trp Asn Trp Arg Ser Asp Lys Asp Leu Leu Glu Asn Gly Ala Ile
            340                 345                 350

Phe Val Thr Ser Gly Ser Asp Pro Val Leu Thr Pro Val Gln Ser Ala
        355                 360                 365

Gly Met Ile Pro Ala Glu Pro Gly Glu Ala Ala Ile Lys Leu Thr Ser
    370                 375                 380

Ser Ala Gly Val Phe Ser Cys His Pro Gly Ala Pro Cys
385                 390                 395


<210> SEQ ID NO 57
<211> LENGTH: 398
<212> TYPE: PRT
<213> ORGANISM: Ambrosia artemisiifolia

<400> SEQUENCE: 57

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Val Glu Glu Phe
            20                  25                  30

Leu Pro Ser Ala Asn Glu Thr Arg Arg Ser Leu Lys Ala Cys Glu Ala
        35                  40                  45

His Asn Ile Ile Asp Lys Cys Trp Arg Cys Lys Ala Asp Trp Ala Asn
    50                  55                  60

Asn Arg Gln Ala Leu Ala Asp Cys Ala Gln Gly Phe Ala Lys Gly Thr
65                  70                  75                  80

Tyr Gly Gly Lys His Gly Asp Val Tyr Thr Val Thr Ser Asp Lys Asp
                85                  90                  95

Asp Asp Val Ala Asn Pro Lys Glu Gly Thr Leu Arg Phe Ala Ala Ala
            100                 105                 110

Gln Asn Arg Pro Leu Trp Ile Ile Phe Lys Arg Asn Met Val Ile His
        115                 120                 125

Leu Asn Gln Glu Leu Val Val Asn Ser Asp Lys Thr Ile Asp Gly Arg
    130                 135                 140

Gly Val Lys Val Asn Ile Val Asn Ala Gly Leu Thr Leu Met Asn Val
145                 150                 155                 160

Lys Asn Ile Ile Ile His Asn Ile Asn Ile His Asp Ile Lys Val Cys
                165                 170                 175

Pro Gly Gly Met Ile Lys Ser Asn Asp Gly Pro Pro Ile Leu Arg Gln
            180                 185                 190

Gln Ser Asp Gly Asp Ala Ile Asn Val Ala Gly Ser Ser Gln Ile Trp
        195                 200                 205

Ile Asp His Cys Ser Leu Ser Lys Ala Ser Asp Gly Leu Leu Asp Ile
    210                 215                 220

Thr Leu Gly Ser Ser His Val Thr Val Ser Asn Cys Lys Phe Thr Gln
225                 230                 235                 240

His Gln Phe Val Leu Leu Leu Gly Ala Asp Asp Thr His Tyr Gln Asp
                245                 250                 255

Lys Gly Met Leu Ala Thr Val Ala Phe Asn Met Phe Thr Asp His Val
            260                 265                 270

Asp Gln Arg Met Pro Arg Cys Arg Phe Gly Phe Phe Gln Val Val Asn
        275                 280                 285

Asn Asn Tyr Asp Arg Trp Gly Thr Tyr Ala Ile Gly Gly Ser Ser Ala
```

```
    290                 295                 300

Pro Thr Ile Leu Ser Gln Gly Asn Arg Phe Phe Ala Pro Asp Asp Ile
305                 310                 315                 320

Ile Lys Lys Asn Val Leu Ala Arg Thr Gly Thr Gly Asn Ala Glu Ser
                325                 330                 335

Met Ser Trp Asn Trp Arg Thr Asp Arg Asp Leu Leu Glu Asn Gly Ala
            340                 345                 350

Ile Phe Leu Pro Ser Gly Ser Asp Pro Val Leu Thr Pro Glu Gln Lys
        355                 360                 365

Ala Gly Met Ile Pro Ala Glu Pro Gly Glu Ala Val Leu Arg Leu Thr
    370                 375                 380

Ser Ser Ala Gly Val Leu Ser Cys His Gln Gly Ala Pro Cys
385                 390                 395


<210> SEQ ID NO 58
<211> LENGTH: 396
<212> TYPE: PRT
<213> ORGANISM: Ambrosia artemisiifolia

<400> SEQUENCE: 58

Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Glu Ile
            20                  25                  30

Leu Pro Val Asn Glu Thr Arg Arg Leu Thr Thr Ser Gly Ala Tyr Asn
        35                  40                  45

Ile Ile Asp Gly Cys Trp Arg Gly Lys Ala Asp Trp Ala Glu Asn Arg
    50                  55                  60

Lys Ala Leu Ala Asp Cys Ala Gln Gly Phe Gly Lys Gly Thr Val Gly
65                  70                  75                  80

Gly Lys Asp Gly Asp Ile Tyr Thr Val Thr Ser Glu Leu Asp Asp Asp
                85                  90                  95

Val Ala Asn Pro Lys Glu Gly Thr Leu Arg Phe Gly Ala Ala Gln Asn
            100                 105                 110

Arg Pro Leu Trp Ile Ile Phe Glu Arg Asp Met Val Ile Arg Leu Asp
        115                 120                 125

Lys Glu Met Val Val Asn Ser Asp Lys Thr Ile Asp Gly Arg Gly Ala
    130                 135                 140

Lys Val Glu Ile Ile Asn Ala Gly Phe Thr Leu Asn Gly Val Lys Asn
145                 150                 155                 160

Val Ile Ile His Asn Ile Asn Met His Asp Val Lys Val Asn Pro Gly
                165                 170                 175

Gly Leu Ile Lys Ser Asn Asp Gly Pro Ala Ala Pro Arg Ala Gly Ser
            180                 185                 190

Asp Gly Asp Ala Ile Ser Ile Ser Gly Ser Ser Gln Ile Trp Ile Asp
        195                 200                 205

His Cys Ser Leu Ser Lys Ser Val Asp Gly Leu Val Asp Ala Lys Leu
    210                 215                 220

Gly Thr Thr Arg Leu Thr Val Ser Asn Ser Leu Phe Thr Gln His Gln
225                 230                 235                 240

Phe Val Leu Leu Phe Gly Ala Gly Asp Glu Asn Ile Glu Asp Arg Gly
                245                 250                 255

Met Leu Ala Thr Val Ala Phe Asn Thr Phe Thr Asp Asn Val Asp Gln
            260                 265                 270
```

```
Arg Met Pro Arg Cys Arg His Gly Phe Phe Gln Val Val Asn Asn Asn
        275                 280                 285

Tyr Asp Lys Trp Gly Ser Tyr Ala Ile Gly Gly Ser Ala Ser Pro Thr
    290                 295                 300

Ile Leu Ser Gln Gly Asn Arg Phe Cys Ala Pro Asp Glu Arg Ser Lys
305                 310                 315                 320

Lys Asn Val Leu Gly Arg His Gly Glu Ala Ala Ala Glu Ser Met Lys
                325                 330                 335

Trp Asn Trp Arg Thr Asn Lys Asp Val Leu Glu Asn Gly Ala Ile Phe
            340                 345                 350

Val Ala Ser Gly Val Asp Pro Val Leu Thr Pro Glu Gln Ser Ala Gly
        355                 360                 365

Met Ile Pro Ala Glu Pro Gly Glu Ser Ala Leu Ser Leu Thr Ser Ser
    370                 375                 380

Ala Gly Val Leu Ser Cys Gln Pro Gly Ala Pro Cys
385                 390                 395


<210> SEQ ID NO 59
<211> LENGTH: 174
<212> TYPE: PRT
<213> ORGANISM: Canis familiaris

<400> SEQUENCE: 59

Met Lys Thr Leu Leu Leu Thr Ile Gly Phe Ser Leu Ile Ala Ile Leu
1               5                   10                  15

Gln Ala Gln Asp Thr Pro Ala Leu Gly Lys Asp Thr Val Ala Val Ser
            20                  25                  30

Gly Lys Trp Tyr Leu Lys Ala Met Thr Ala Asp Gln Glu Val Pro Glu
        35                  40                  45

Lys Pro Asp Ser Val Thr Pro Met Ile Leu Lys Ala Gln Lys Gly Gly
    50                  55                  60

Asn Leu Glu Ala Lys Ile Thr Met Leu Thr Asn Gly Gln Cys Gln Asn
65                  70                  75                  80

Ile Thr Val Val Leu His Lys Thr Ser Glu Pro Gly Lys Tyr Thr Ala
                85                  90                  95

Tyr Glu Gly Gln Arg Val Val Phe Ile Gln Pro Ser Pro Val Arg Asp
            100                 105                 110

His Tyr Ile Leu Tyr Cys Glu Gly Glu Leu His Gly Arg Gln Ile Arg
        115                 120                 125

Met Ala Lys Leu Leu Gly Arg Asp Pro Glu Gln Ser Gln Glu Ala Leu
    130                 135                 140

Glu Asp Phe Arg Glu Phe Ser Arg Ala Lys Gly Leu Asn Gln Glu Ile
145                 150                 155                 160

Leu Glu Leu Ala Gln Ser Glu Thr Cys Ser Pro Gly Gly Gln
                165                 170


<210> SEQ ID NO 60
<211> LENGTH: 24
<212> TYPE: PRT
<213> ORGANISM: Canis familiaris

<400> SEQUENCE: 60

Glu Ala Tyr Lys Ser Glu Ile Ala His Arg Tyr Asn Asp Leu Gly Glu
1               5                   10                  15

Glu His Phe Arg Gly Leu Val Leu
            20
```

<210> SEQ ID NO 61
<211> LENGTH: 265
<212> TYPE: PRT
<213> ORGANISM: Canis familiaris

<400> SEQUENCE: 61

Leu Ser Ser Ala Lys Glu Arg Phe Lys Cys Ala Ser Leu Gln Lys Phe
1 5 10 15

Gly Asp Arg Ala Phe Lys Ala Trp Ser Val Ala Arg Leu Ser Gln Arg
20 25 30

Phe Pro Lys Ala Asp Phe Ala Glu Ile Ser Lys Val Val Thr Asp Leu
35 40 45

Thr Lys Val His Lys Glu Cys Cys His Gly Asp Leu Leu Glu Cys Ala
50 55 60

Asp Asp Arg Ala Asp Leu Ala Lys Tyr Met Cys Glu Asn Gln Asp Ser
65 70 75 80

Ile Ser Thr Lys Leu Lys Glu Cys Cys Asp Lys Pro Val Leu Glu Lys
85 90 95

Ser Gln Cys Leu Ala Glu Val Glu Arg Asp Glu Leu Pro Gly Asp Leu
100 105 110

Pro Ser Leu Ala Ala Asp Phe Val Glu Asp Lys Glu Val Cys Lys Asn
115 120 125

Tyr Gln Glu Ala Lys Asp Val Phe Leu Gly Thr Phe Leu Tyr Glu Tyr
130 135 140

Ser Arg Arg His Pro Glu Tyr Ser Val Ser Leu Leu Leu Arg Leu Ala
145 150 155 160

Lys Glu Tyr Glu Ala Thr Leu Glu Lys Cys Cys Ala Thr Asp Asp Pro
165 170 175

Pro Thr Cys Tyr Ala Lys Val Leu Asp Glu Phe Lys Pro Leu Val Asp
180 185 190

Glu Pro Gln Asn Leu Val Lys Thr Asn Cys Glu Leu Phe Glu Lys Leu
195 200 205

Gly Glu Tyr Gly Phe Gln Asn Ala Leu Leu Val Arg Tyr Thr Lys Lys
210 215 220

Ala Pro Gln Val Ser Thr Pro Thr Leu Val Val Glu Val Ser Arg Lys
225 230 235 240

Leu Gly Lys Val Gly Thr Lys Cys Cys Lys Lys Pro Glu Ser Glu Arg
245 250 255

Met Ser Cys Ala Asp Asp Phe Leu Ser
260 265

<210> SEQ ID NO 62
<211> LENGTH: 180
<212> TYPE: PRT
<213> ORGANISM: Canis familiaris

<400> SEQUENCE: 62

Met Gln Leu Leu Leu Leu Thr Val Gly Leu Ala Leu Ile Cys Gly Leu
1 5 10 15

Gln Ala Gln Glu Gly Asn His Glu Glu Pro Gln Gly Gly Leu Glu Glu
20 25 30

Leu Ser Gly Arg Trp His Ser Val Ala Leu Ala Ser Asn Lys Ser Asp
35 40 45

Leu Ile Lys Pro Trp Gly His Phe Arg Val Phe Ile His Ser Met Ser
50 55 60

Ala Lys Asp Gly Asn Leu His Gly Asp Ile Leu Ile Pro Gln Asp Gly
65 70 75 80

Gln Cys Glu Lys Val Ser Leu Thr Ala Phe Lys Thr Ala Thr Ser Asn
85 90 95

Lys Phe Asp Leu Glu Tyr Trp Gly His Asn Asp Leu Tyr Leu Ala Glu
100 105 110

Val Asp Pro Lys Ser Tyr Leu Ile Leu Tyr Met Ile Asn Gln Tyr Asn
115 120 125

Asp Asp Thr Ser Leu Val Ala His Leu Met Val Arg Asp Leu Ser Arg
130 135 140

Gln Gln Asp Phe Leu Pro Ala Phe Glu Ser Val Cys Glu Asp Ile Gly
145 150 155 160

Leu His Lys Asp Gln Ile Val Val Leu Ser Asp Asp Asp Arg Cys Gln
165 170 175

Gly Ser Arg Asp
180

<210> SEQ ID NO 63
<211> LENGTH: 187
<212> TYPE: PRT
<213> ORGANISM: Equus caballus

<400> SEQUENCE: 63

Met Lys Leu Leu Leu Leu Cys Leu Gly Leu Ile Leu Val Cys Ala Gln
1 5 10 15

Gln Glu Glu Asn Ser Asp Val Ala Ile Arg Asn Phe Asp Ile Ser Lys
20 25 30

Ile Ser Gly Glu Trp Tyr Ser Ile Phe Leu Ala Ser Asp Val Lys Glu
35 40 45

Lys Ile Glu Glu Asn Gly Ser Met Arg Val Phe Val Asp Val Ile Arg
50 55 60

Ala Leu Asp Asn Ser Ser Leu Tyr Ala Glu Tyr Gln Thr Lys Val Asn
65 70 75 80

Gly Glu Cys Thr Glu Phe Pro Met Val Phe Asp Lys Thr Glu Glu Asp
85 90 95

Gly Val Tyr Ser Leu Asn Tyr Asp Gly Tyr Asn Val Phe Arg Ile Ser
100 105 110

Glu Phe Glu Asn Asp Glu His Ile Ile Leu Tyr Leu Val Asn Phe Asp
115 120 125

Lys Asp Arg Pro Phe Gln Leu Phe Glu Phe Tyr Ala Arg Glu Pro Asp
130 135 140

Val Ser Pro Glu Ile Lys Glu Glu Phe Val Lys Ile Val Gln Lys Arg
145 150 155 160

Gly Ile Val Lys Glu Asn Ile Ile Asp Leu Thr Lys Ile Asp Arg Cys
165 170 175

Phe Gln Leu Arg Gly Asn Gly Val Ala Gln Ala
180 185

<210> SEQ ID NO 64
<211> LENGTH: 29
<212> TYPE: PRT
<213> ORGANISM: Equus caballus
<220> FEATURE:
<221> NAME/KEY: MOD_RES
<222> LOCATION: (3)..(3)
<223> OTHER INFORMATION: Any naturally occurring amino acid
<220> FEATURE:
<221> NAME/KEY: MOD_RES
<222> LOCATION: (28)..(28)
<223> OTHER INFORMATION: Any naturally occurring amino acid

<400> SEQUENCE: 64

```
Ser Gln Xaa Pro Gln Ser Glu Thr Asp Tyr Ser Gln Leu Ser Gly Glu
1               5                   10                  15

Trp Asn Thr Ile Tyr Gly Ala Ala Ser Asn Ile Xaa Lys
            20                  25
```

<210> SEQ ID NO 65
<211> LENGTH: 211
<212> TYPE: PRT
<213> ORGANISM: Euroglyphus maynei

<400> SEQUENCE: 65

```
Thr Tyr Ala Cys Ser Ile Asn Ser Val Ser Leu Pro Ser Glu Leu Asp
1               5                   10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ser Thr Glu Ser Ala Tyr
        35                  40                  45

Leu Ala Tyr Arg Asn Met Ser Leu Asp Leu Ala Glu Gln Glu Leu Val
    50                  55                  60

Asp Cys Ala Ser Gln Asn Gly Cys His Gly Asp Thr Ile Pro Arg Gly
65                  70                  75                  80

Ile Glu Tyr Ile Gln Gln Asn Gly Val Val Gln Glu His Tyr Tyr Pro
                85                  90                  95

Tyr Val Ala Arg Glu Gln Ser Cys His Arg Pro Asn Ala Gln Arg Tyr
            100                 105                 110

Gly Leu Lys Asn Tyr Cys Gln Ile Ser Pro Pro Asp Ser Asn Lys Ile
        115                 120                 125

Arg Gln Ala Leu Thr Gln Thr His Thr Ala Val Ala Val Ile Ile Gly
    130                 135                 140

Ile Lys Asp Leu Asn Ala Phe Arg His Tyr Asp Gly Arg Thr Ile Met
145                 150                 155                 160

Gln His Asp Asn Gly Tyr Gln Pro Asn Tyr His Ala Val Asn Ile Val
                165                 170                 175

Gly Tyr Gly Asn Thr Gln Gly Val Asp Tyr Trp Ile Val Arg Asn Ser
            180                 185                 190

Trp Asp Thr Thr Trp Gly Asp Asn Gly Tyr Gly Tyr Phe Ala Ala Asn
        195                 200                 205

Ile Asn Leu
    210
```

<210> SEQ ID NO 66
<211> LENGTH: 211
<212> TYPE: PRT
<213> ORGANISM: Euroglyphus maynei

<400> SEQUENCE: 66

```
Thr Tyr Ala Cys Ser Ile Asn Ser Val Ser Leu Pro Ser Glu Leu Asp
1               5                   10                  15

Leu Arg Ser Leu Arg Thr Val Thr Pro Ile Arg Met Gln Gly Gly Cys
            20                  25                  30

Gly Ser Cys Trp Ala Phe Ser Gly Val Ala Ser Thr Glu Ser Ala Tyr
        35                  40                  45

Leu Ala Tyr Arg Asn Met Ser Leu Asp Leu Ala Glu Gln Glu Leu Val
```

```
    50                  55                  60

Asp Cys Ala Ser Gln Asn Gly Cys His Gly Asp Thr Ile Pro Arg Gly
65                  70                  75                  80

Ile Glu Tyr Ile Gln Gln Asn Gly Val Val Gln Glu His Tyr Tyr Pro
                85                  90                  95

Tyr Val Ala Arg Glu Gln Ser Cys His Arg Pro Asn Ala Gln Arg Tyr
            100                 105                 110

Gly Leu Lys Asn Tyr Cys Gln Ile Ser Pro Pro Asp Ser Asn Lys Ile
        115                 120                 125

Arg Gln Ala Leu Thr Gln Thr His Thr Ala Val Ala Val Ile Ile Gly
    130                 135                 140

Ile Lys Asp Leu Asn Ala Phe Arg His Tyr Asp Gly Arg Thr Ile Met
145                 150                 155                 160

Gln His Asp Asn Gly Tyr Gln Pro Asn Tyr His Ala Val Asn Ile Val
                165                 170                 175

Gly Tyr Gly Asn Thr Gln Gly Val Asp Tyr Trp Ile Val Arg Asn Ser
            180                 185                 190

Trp Asp Thr Thr Trp Gly Asp Asn Gly Tyr Gly Tyr Phe Ala Ala Asn
        195                 200                 205

Ile Asn Leu
    210


<210> SEQ ID NO 67
<211> LENGTH: 211
<212> TYPE: PRT
<213> ORGANISM: Euroglyphus maynei

<400> SEQUENCE: 67

Glu Thr Asn Ala Cys Ser Ile Asn Gly Asn Ala Pro Ala Glu Ile Asp
1               5                   10                  15

Leu Arg Gln Met Arg Thr Val Thr Pro Ile Arg Met Gln Gly Gly Cys
            20                  25                  30

Gly Ser Cys Trp Ala Phe Ser Gly Val Ala Ala Thr Glu Ser Ala Tyr
        35                  40                  45

Leu Ala Tyr Arg Asn Gln Ser Leu Asp Leu Ala Glu Gln Glu Leu Val
    50                  55                  60

Asp Cys Ala Ser Gln His Gly Cys His Gly Asp Thr Ile Pro Arg Gly
65                  70                  75                  80

Ile Glu Tyr Ile Gln His Asn Gly Val Val Gln Glu Ser Tyr Tyr Arg
                85                  90                  95

Tyr Val Ala Arg Glu Gln Ser Cys Arg Arg Pro Asn Ala Gln Arg Phe
            100                 105                 110

Gly Ile Ser Asn Tyr Cys Gln Ile Tyr Pro Pro Asn Ala Asn Lys Ile
        115                 120                 125

Arg Glu Ala Leu Ala Gln Thr His Ser Ala Ile Ala Val Ile Ile Gly
    130                 135                 140

Ile Lys Asp Leu Asp Ala Phe Arg His Tyr Asp Gly Arg Thr Ile Ile
145                 150                 155                 160

Gln Arg Asp Asn Gly Tyr Gln Pro Asn Tyr His Ala Val Asn Ile Val
                165                 170                 175

Gly Tyr Ser Asn Ala Gln Gly Val Asp Tyr Trp Ile Val Arg Asn Ser
            180                 185                 190

Trp Asp Thr Asn Trp Gly Asp Asn Gly Tyr Gly Tyr Phe Ala Ala Asn
        195                 200                 205
```

Ile Asp Leu
210

<210> SEQ ID NO 68
<211> LENGTH: 212
<212> TYPE: PRT
<213> ORGANISM: Euroglyphus maynei

<400> SEQUENCE: 68

Glu Thr Ser Ala Cys Arg Ile Asn Ser Val Asn Val Pro Ser Glu Leu
1 5 10 15

Asp Leu Arg Ser Leu Arg Thr Val Thr Pro Ile Arg Met Gln Gly Gly
20 25 30

Cys Gly Ser Cys Trp Ala Phe Ser Gly Val Ala Ala Thr Glu Ser Ala
35 40 45

Tyr Leu Ala Tyr Arg Asn Thr Ser Leu Asp Leu Ser Glu Gln Glu Leu
50 55 60

Val Asp Cys Ala Ser Gln His Gly Cys His Gly Asp Thr Ile Pro Arg
65 70 75 80

Gly Ile Glu Tyr Ile Gln Gln Asn Gly Val Val Glu Glu Arg Ser Tyr
85 90 95

Pro Tyr Val Ala Arg Glu Gln Gln Cys Arg Arg Pro Asn Ser Gln His
100 105 110

Tyr Gly Ile Ser Asn Tyr Cys Gln Ile Tyr Pro Pro Asp Val Lys Gln
115 120 125

Ile Arg Glu Ala Leu Thr Gln Thr His Thr Ala Ile Ala Val Ile Ile
130 135 140

Gly Ile Lys Asp Leu Arg Ala Phe Gln His Tyr Asp Gly Arg Thr Ile
145 150 155 160

Ile Gln His Asp Asn Gly Tyr Gln Pro Asn Tyr His Ala Val Asn Ile
165 170 175

Val Gly Tyr Gly Ser Thr Gln Gly Val Asp Tyr Trp Ile Val Arg Asn
180 185 190

Ser Trp Asp Thr Thr Trp Gly Asp Ser Gly Tyr Gly Tyr Phe Gln Ala
195 200 205

Gly Asn Asn Leu
210

<210> SEQ ID NO 69
<211> LENGTH: 685
<212> TYPE: PRT
<213> ORGANISM: Periplaneta americana

<400> SEQUENCE: 69

Met Lys Thr Ala Leu Val Phe Ala Ala Val Val Ala Phe Val Ala Ala
1 5 10 15

Arg Phe Pro Asp His Lys Asp Tyr Lys Gln Leu Ala Asp Lys Gln Phe
20 25 30

Leu Ala Lys Gln Arg Asp Val Leu Arg Leu Phe His Arg Val His Gln
35 40 45

His Asn Ile Leu Asn Asp Gln Val Glu Val Gly Ile Pro Met Thr Ser
50 55 60

Lys Gln Thr Ser Ala Thr Thr Val Pro Pro Ser Gly Glu Ala Val His
65 70 75 80

Gly Val Leu Gln Glu Gly His Ala Arg Pro Arg Gly Glu Pro Phe Ser
85 90 95

```
Val Asn Tyr Glu Lys His Arg Glu Gln Ala Ile Met Leu Tyr Asp Leu
            100                 105                 110

Leu Tyr Phe Ala Asn Asp Tyr Asp Thr Phe Tyr Lys Thr Ala Cys Trp
        115                 120                 125

Ala Arg Asp Arg Val Asn Glu Gly Met Phe Met Tyr Ser Phe Ser Ile
    130                 135                 140

Ala Val Phe His Arg Asp Asp Met Gln Gly Val Met Leu Pro Pro Pro
145                 150                 155                 160

Tyr Glu Val Tyr Pro Tyr Leu Phe Val Asp His Asp Val Ile His Met
                165                 170                 175

Ala Gln Lys Tyr Trp Met Lys Asn Ala Gly Ser Gly Glu His His Ser
            180                 185                 190

His Val Ile Pro Val Asn Phe Thr Leu Arg Thr Gln Asp His Leu Leu
        195                 200                 205

Ala Tyr Phe Thr Ser Asp Val Asn Leu Asn Ala Phe Asn Thr Tyr Tyr
    210                 215                 220

Arg Tyr Tyr Tyr Pro Ser Trp Tyr Asn Thr Thr Leu Tyr Gly His Asn
225                 230                 235                 240

Ile Asp Arg Arg Gly Glu Gln Phe Tyr Tyr Thr Tyr Lys Gln Ile Tyr
                245                 250                 255

Ala Arg Tyr Phe Leu Glu Arg Leu Ser Asn Asp Leu Pro Asp Val Tyr
            260                 265                 270

Pro Phe Tyr Tyr Ser Lys Pro Val Lys Ser Ala Tyr Asn Pro Asn Leu
        275                 280                 285

Arg Tyr His Asn Gly Glu Glu Met Pro Val Arg Pro Ser Asn Met Tyr
    290                 295                 300

Val Thr Asn Phe Asp Leu Tyr Tyr Ile Ala Asp Ile Lys Asn Tyr Glu
305                 310                 315                 320

Lys Arg Val Glu Asp Ala Ile Asp Phe Gly Tyr Ala Phe Asp Glu His
                325                 330                 335

Met Lys Pro His Ser Leu Tyr His Asp Val His Gly Met Glu Tyr Leu
            340                 345                 350

Ala Asp Met Ile Glu Gly Asn Met Asp Ser Pro Asn Phe Tyr Phe Tyr
        355                 360                 365

Gly Ser Ile Tyr His Met Tyr His Ser Met Ile Gly His Ile Val Asp
    370                 375                 380

Pro Tyr His Lys Met Gly Leu Ala Pro Ser Leu Glu His Pro Glu Thr
385                 390                 395                 400

Val Leu Arg Asp Pro Val Phe Tyr Gln Leu Trp Lys Arg Val Asp His
                405                 410                 415

Leu Phe Gln Lys Tyr Lys Asn Arg Leu Pro Arg Tyr Thr His Asp Glu
            420                 425                 430

Leu Ala Phe Glu Gly Val Lys Val Glu Asn Val Asp Val Gly Lys Leu
        435                 440                 445

Tyr Thr Tyr Phe Glu Gln Tyr Asp Met Ser Leu Asp Met Ala Val Tyr
    450                 455                 460

Val Asn Asn Val Asp Gln Ile Ser Asn Val Asp Val Gln Leu Ala Val
465                 470                 475                 480

Arg Leu Asn His Lys Pro Phe Thr Tyr Asn Ile Glu Val Ser Ser Asp
                485                 490                 495

Lys Ala Gln Asp Val Tyr Val Ala Val Phe Leu Gly Pro Lys Tyr Asp
            500                 505                 510

Tyr Leu Gly Arg Glu Tyr Asp Leu Asn Asp Arg Arg His Tyr Phe Val
```

```
        515                 520                 525

Glu Met Asp Arg Phe Pro Tyr His Val Gly Ala Gly Lys Thr Val Ile
    530                 535                 540

Glu Arg Asn Ser His Asp Ser Asn Ile Ile Ala Pro Glu Arg Asp Ser
545                 550                 555                 560

Tyr Arg Thr Phe Tyr Lys Lys Val Gln Glu Ala Tyr Glu Gly Lys Ser
                565                 570                 575

Gln Tyr Tyr Val Asp Lys Gly His Asn Tyr Cys Gly Tyr Pro Glu Asn
            580                 585                 590

Leu Leu Ile Pro Lys Gly Lys Lys Gly Gly Gln Ala Tyr Thr Phe Tyr
        595                 600                 605

Val Ile Val Thr Pro Tyr Val Lys Gln Asp Glu His Asp Phe Glu Pro
    610                 615                 620

Tyr Asn Tyr Lys Ala Phe Ser Tyr Cys Gly Val Gly Ser Glu Arg Lys
625                 630                 635                 640

Tyr Pro Asp Asn Lys Pro Leu Gly Tyr Pro Phe Asp Arg Lys Ile Tyr
                645                 650                 655

Ser Asn Asp Phe Tyr Thr Pro Asn Met Tyr Phe Lys Asp Val Ile Ile
            660                 665                 670

Phe His Lys Lys Tyr Asp Glu Val Gly Val Gln Gly His
        675                 680                 685


<210> SEQ ID NO 70
<211> LENGTH: 446
<212> TYPE: PRT
<213> ORGANISM: Periplaneta americana

<400> SEQUENCE: 70

Ile Asn Glu Ile His Ser Ile Ile Gly Leu Pro Pro Phe Val Pro Pro
1               5                   10                  15

Ser Arg Arg His Ala Arg Arg Gly Val Gly Ile Asn Gly Leu Ile Asp
            20                  25                  30

Asp Val Ile Ala Ile Leu Pro Val Asp Glu Leu Lys Ala Leu Phe Gln
        35                  40                  45

Glu Lys Leu Glu Thr Ser Pro Asp Phe Lys Ala Leu Tyr Asp Ala Ile
    50                  55                  60

Arg Ser Pro Glu Phe Gln Ser Ile Ile Ser Thr Leu Asn Ala Met Gln
65                  70                  75                  80

Arg Ser Glu His His Gln Asn Leu Arg Asp Lys Gly Val Asp Val Asp
                85                  90                  95

His Phe Ile Gln Leu Ile Arg Ala Leu Phe Gly Leu Ser Arg Ala Ala
            100                 105                 110

Arg Asn Leu Gln Asp Asp Leu Asn Asp Phe Leu His Ser Leu Glu Pro
        115                 120                 125

Ile Ser Pro Arg His Arg His Gly Leu Pro Arg Gln Arg Arg Arg Ser
    130                 135                 140

Ala Arg Val Ser Ala Tyr Leu His Ala Asp Asp Phe His Lys Ile Ile
145                 150                 155                 160

Thr Thr Ile Glu Ala Leu Pro Glu Phe Ala Asn Phe Tyr Asn Phe Leu
                165                 170                 175

Lys Glu His Gly Leu Asp Val Val Asp Tyr Ile Asn Glu Ile His Ser
            180                 185                 190

Ile Ile Gly Leu Pro Pro Phe Val Pro Pro Ser Arg Arg His Ala Arg
        195                 200                 205
```

-continued

```
Arg Gly Val Gly Ile Asn Gly Leu Ile Asp Asp Val Ile Ala Ile Leu
    210                 215                 220

Pro Val Asp Glu Leu Lys Ala Leu Phe Gln Glu Lys Leu Glu Thr Ser
225                 230                 235                 240

Pro Asp Phe Lys Ala Leu Tyr Asp Ala Ile Arg Ser Pro Glu Phe Gln
                245                 250                 255

Ser Ile Ile Ser Thr Leu Asn Ala Met Pro Glu Tyr Gln Glu Leu Leu
            260                 265                 270

Gln Asn Leu Arg Asp Lys Gly Val Asp Val Asp His Phe Ile Arg Val
        275                 280                 285

Asp Gln Gly Thr Leu Arg Thr Leu Ser Ser Gly Gln Arg Asn Leu Gln
    290                 295                 300

Asp Asp Leu Asn Asp Phe Leu Ala Leu Ile Pro Thr Asp Gln Ile Leu
305                 310                 315                 320

Ala Ile Ala Met Asp Tyr Leu Ala Asn Asp Ala Glu Val Gln Glu Leu
                325                 330                 335

Val Ala Tyr Leu Gln Ser Asp Asp Phe His Lys Ile Ile Thr Thr Ile
            340                 345                 350

Glu Ala Leu Pro Glu Phe Ala Asn Phe Tyr Asn Phe Leu Lys Glu His
        355                 360                 365

Gly Leu Asp Val Val Asp Tyr Ile Asn Glu Ile His Ser Ile Ile Gly
    370                 375                 380

Leu Pro Pro Phe Val Pro Pro Ser Gln Arg His Ala Arg Arg Gly Val
385                 390                 395                 400

Gly Ile Asn Gly Leu Ile Asp Asp Val Ile Ala Ile Leu Pro Val Asp
                405                 410                 415

Glu Leu Lys Ala Leu Phe Gln Glu Lys Leu Glu Thr Ser Pro Asp Phe
            420                 425                 430

Lys Ala Leu Tyr Asp Ala Ile Asp Leu Arg Ser Ser Arg Ala
        435                 440                 445


<210> SEQ ID NO 71
<211> LENGTH: 352
<212> TYPE: PRT
<213> ORGANISM: Blattella germanica

<400> SEQUENCE: 71

Met Ile Gly Leu Lys Leu Val Thr Val Leu Phe Ala Val Ala Thr Ile
1               5                   10                  15

Thr His Ala Ala Glu Leu Gln Arg Val Pro Leu Tyr Lys Leu Val His
            20                  25                  30

Val Phe Ile Asn Thr Gln Tyr Ala Gly Ile Thr Lys Ile Gly Asn Gln
        35                  40                  45

Asn Phe Leu Thr Val Phe Asp Ser Thr Ser Cys Asn Val Val Val Ala
    50                  55                  60

Ser Gln Glu Cys Val Gly Gly Ala Cys Val Cys Pro Asn Leu Gln Lys
65                  70                  75                  80

Tyr Glu Lys Leu Lys Pro Lys Tyr Ile Ser Asp Gly Asn Val Gln Val
                85                  90                  95

Lys Phe Phe Asp Thr Gly Ser Ala Val Gly Arg Gly Ile Glu Asp Ser
            100                 105                 110

Leu Thr Ile Ser Asn Leu Thr Thr Ser Gln Gln Asp Ile Val Leu Ala
        115                 120                 125

Asp Glu Leu Ser Gln Glu Val Cys Ile Leu Ser Ala Asp Val Val Val
    130                 135                 140
```

```
Gly Ile Ala Ala Pro Gly Cys Pro Asn Ala Leu Lys Gly Lys Thr Val
145                 150                 155                 160

Leu Glu Asn Phe Val Glu Glu Asn Leu Ile Ala Pro Val Phe Ser Ile
                165                 170                 175

His His Ala Arg Phe Gln Asp Gly Glu His Phe Gly Glu Ile Ile Phe
            180                 185                 190

Gly Gly Ser Asp Trp Lys Tyr Val Asp Gly Glu Phe Thr Tyr Val Pro
        195                 200                 205

Leu Val Gly Asp Asp Ser Trp Lys Phe Arg Leu Asp Gly Val Lys Ile
    210                 215                 220

Gly Asp Thr Thr Val Ala Pro Ala Gly Thr Gln Ala Ile Ile Asp Thr
225                 230                 235                 240

Ser Lys Ala Ile Ile Val Gly Pro Lys Ala Tyr Val Asn Pro Ile Asn
                245                 250                 255

Glu Ala Ile Gly Cys Val Val Glu Lys Thr Thr Thr Arg Arg Ile Cys
            260                 265                 270

Lys Leu Asp Cys Ser Lys Ile Pro Ser Leu Pro Asp Val Thr Phe Val
        275                 280                 285

Ile Asn Gly Arg Asn Phe Asn Ile Ser Ser Gln Tyr Tyr Ile Gln Gln
    290                 295                 300

Asn Gly Asn Leu Cys Tyr Ser Gly Phe Gln Pro Cys Gly His Ser Asp
305                 310                 315                 320

His Phe Phe Ile Gly Asp Phe Phe Val Asp His Tyr Tyr Ser Glu Phe
                325                 330                 335

Asn Trp Glu Asn Lys Thr Met Gly Phe Gly Arg Ser Val Glu Ser Val
            340                 345                 350


<210> SEQ ID NO 72
<211> LENGTH: 182
<212> TYPE: PRT
<213> ORGANISM: Blattella germanica

<400> SEQUENCE: 72

Ala Val Leu Ala Leu Cys Ala Thr Asp Thr Leu Ala Asn Glu Asp Cys
1               5                   10                  15

Phe Arg His Glu Ser Leu Val Pro Asn Leu Asp Tyr Glu Arg Phe Arg
            20                  25                  30

Gly Ser Trp Ile Ile Ala Ala Gly Thr Ser Glu Ala Leu Thr Gln Tyr
        35                  40                  45

Lys Cys Trp Ile Asp Arg Phe Ser Tyr Asp Asp Ala Leu Val Ser Lys
    50                  55                  60

Tyr Thr Asp Ser Gln Gly Lys Asn Arg Thr Thr Ile Arg Gly Arg Thr
65                  70                  75                  80

Lys Phe Glu Gly Asn Lys Phe Thr Ile Asp Tyr Asn Asp Lys Gly Lys
                85                  90                  95

Ala Phe Ser Ala Pro Tyr Ser Val Leu Ala Thr Asp Tyr Glu Asn Tyr
            100                 105                 110

Ala Ile Val Glu Gly Cys Pro Ala Ala Ala Asn Gly His Val Ile Tyr
        115                 120                 125

Val Gln Ile Arg Phe Ser Val Arg Arg Phe His Pro Lys Leu Gly Asp
    130                 135                 140

Lys Glu Met Ile Gln His Tyr Thr Leu Asp Gln Val Asn Gln His Lys
145                 150                 155                 160

Lys Ala Ile Glu Glu Asp Leu Lys His Phe Asn Leu Lys Tyr Glu Asp
```

```
            165                 170                 175

Leu His Ser Thr Cys His
            180


<210> SEQ ID NO 73
<211> LENGTH: 200
<212> TYPE: PRT
<213> ORGANISM: Blattella germanica

<400> SEQUENCE: 73

Tyr Lys Leu Thr Tyr Cys Pro Val Lys Ala Leu Gly Glu Pro Ile Arg
1               5                   10                  15

Phe Leu Leu Ser Tyr Gly Glu Lys Asp Phe Glu Asp Tyr Arg Phe Gln
            20                  25                  30

Glu Gly Asp Trp Pro Asn Leu Lys Pro Ser Met Pro Phe Gly Lys Thr
        35                  40                  45

Pro Val Leu Glu Ile Asp Gly Lys Gln Thr His Gln Ser Val Ala Ile
    50                  55                  60

Ser Arg Tyr Leu Gly Lys Gln Phe Gly Leu Ser Gly Lys Asp Asp Trp
65                  70                  75                  80

Glu Asn Leu Glu Ile Asp Met Ile Val Asp Thr Ile Ser Asp Phe Arg
                85                  90                  95

Ala Ala Ile Ala Asn Tyr His Tyr Asp Ala Asp Glu Asn Ser Lys Gln
            100                 105                 110

Lys Lys Trp Asp Pro Leu Lys Lys Glu Thr Ile Pro Tyr Tyr Thr Lys
        115                 120                 125

Lys Phe Asp Glu Val Val Lys Ala Asn Gly Gly Tyr Leu Ala Ala Gly
    130                 135                 140

Lys Leu Thr Trp Ala Asp Phe Tyr Phe Val Ala Ile Leu Asp Tyr Leu
145                 150                 155                 160

Asn His Met Ala Lys Glu Asp Leu Val Ala Asn Gln Pro Asn Leu Lys
                165                 170                 175

Ala Leu Arg Glu Lys Val Leu Gly Leu Pro Ala Ile Lys Ala Trp Val
            180                 185                 190

Ala Lys Arg Pro Pro Thr Asp Leu
        195                 200


<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Lys Lys Gly Glu Ala Ala Ile Lys Leu Thr Ser Ser Ala Gly Val Leu
1               5                   10                  15

Ser Lys


<210> SEQ ID NO 75
<211> LENGTH: 13
<212> TYPE: PRT
<213> ORGANISM: Dermatophagoides pteronyssinus

<400> SEQUENCE: 75

Ile Asp Leu Arg Gln Met Arg Thr Val Thr Pro Ile Arg
1               5                   10
```

<210> SEQ ID NO 76
<211> LENGTH: 19
<212> TYPE: PRT
<213> ORGANISM: Dermatophagoides pteronyssinus

<400> SEQUENCE: 76

Ile Asp Leu Arg Gln Met Arg Thr Val Thr Pro Ile Arg Met Gln Gly
1 5 10 15

Gly Ser Gly

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic HDM02A peptide

<400> SEQUENCE: 77

Arg Thr Val Thr Pro Ile Arg Met Gln Gly Gly Ser Gly
1 5 10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic HDM02B peptide
<220> FEATURE:
<221> NAME/KEY: MOD_RES
<222> LOCATION: (12)..(12)
<223> OTHER INFORMATION: 5-aminobutyric acid

<400> SEQUENCE: 78

Arg Thr Val Thr Pro Ile Arg Met Gln Gly Gly Xaa Gly
1 5 10

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic HDM03F peptide

<400> SEQUENCE: 79

Arg Asn Gln Ser Leu Asp Leu Ala Glu Gln Glu Leu Val Asp Ser Ala
1 5 10 15

Ser

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic HDM03G peptide
<220> FEATURE:
<221> NAME/KEY: MOD_RES
<222> LOCATION: (13)..(13)
<223> OTHER INFORMATION: 5-aminobutyric acid

<400> SEQUENCE: 80

Gln Ser Leu Asp Leu Ala Glu Gln Glu Leu Val Asp Xaa Ala Ser Gln
1 5 10 15

His Gly

<210> SEQ ID NO 81
<211> LENGTH: 16
<212> TYPE: PRT
<213> ORGANISM: Artificial Sequence
<220> FEATURE:
<223> OTHER INFORMATION: Description of Artificial Sequence: Synthetic
HDM03H peptide
<220> FEATURE:
<221> NAME/KEY: MOD_RES
<222> LOCATION: (11)..(11)
<223> OTHER INFORMATION: 5-aminobutyric acid

<400> SEQUENCE: 81

Leu Asp Leu Ala Glu Gln Glu Leu Val Asp Xaa Ala Ser Gln His Gly
1 5 10 15

<210> SEQ ID NO 82
<211> LENGTH: 14
<212> TYPE: PRT
<213> ORGANISM: Artificial Sequence
<220> FEATURE:
<223> OTHER INFORMATION: Description of Artificial Sequence: Synthetic
HDM03J peptide
<220> FEATURE:
<221> NAME/KEY: MOD_RES
<222> LOCATION: (9)..(9)
<223> OTHER INFORMATION: 5-aminobutyric acid

<400> SEQUENCE: 82

Leu Ala Glu Gln Glu Leu Val Asp Xaa Ala Ser Gln His Gly
1 5 10

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
HDM03K peptide
<220> FEATURE:
<221> NAME/KEY: MOD_RES
<222> LOCATION: (7)..(7)
<223> OTHER INFORMATION: 5-aminobutyric acid

<400> SEQUENCE: 83

Glu Gln Glu Leu Val Asp Xaa Ala Ser Gln His Gly
1 5 10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
HDM03L peptide
<220> FEATURE:
<221> NAME/KEY: MOD_RES
<222> LOCATION: (5)..(5)
<223> OTHER INFORMATION: 5-aminobutyric acid

<400> SEQUENCE: 84

Glu Leu Val Asp Xaa Ala Ser Gln His Gly
1 5 10

<210> SEQ ID NO 85
<211> LENGTH: 20
<212> TYPE: PRT
<213> ORGANISM: Dermatophagoides pteronyssinus

<400> SEQUENCE: 85

Arg Asn Gln Ser Leu Asp Leu Ala Glu Gln Glu Leu Val Asp Cys Ala
1 5 10 15

Ser Gln His Gly
20

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic HDM03N peptide
<220> FEATURE:
<221> NAME/KEY: MOD_RES
<222> LOCATION: (15)..(15)
<223> OTHER INFORMATION: Cystine

<400> SEQUENCE: 86

Arg Asn Gln Ser Leu Asp Leu Ala Glu Gln Glu Leu Val Asp Xaa Ala
1 5 10 15

Ser Gln His Gly
20

<210> SEQ ID NO 87
<211> LENGTH: 23
<212> TYPE: PRT
<213> ORGANISM: Dermatophagoides pteronyssinus

<400> SEQUENCE: 87

Ser Ala Tyr Leu Ala His Arg Asn Gln Ser Leu Asp Leu Ala Glu Gln
1 5 10 15

Glu Leu Val Asp Cys Ala Ser
20

<210> SEQ ID NO 88
<211> LENGTH: 18
<212> TYPE: PRT
<213> ORGANISM: Artificial Sequence
<220> FEATURE:
<223> OTHER INFORMATION: Description of Artificial Sequence: Synthetic HDM03R peptide

<400> SEQUENCE: 88

Gln Ser Leu Asp Leu Ala Glu Gln Glu Leu Val Asp Ser Ala Ser Gln
1 5 10 15

His Gly

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic HDM03S peptide

<400> SEQUENCE: 89

Leu Asp Leu Ala Glu Gln Glu Leu Val Asp Ser Ala Ser Gln His Gly
1 5 10 15

<210> SEQ ID NO 90
<211> LENGTH: 14
<212> TYPE: PRT
<213> ORGANISM: Artificial Sequence

```
<220> FEATURE:
<223> OTHER INFORMATION: Description of Artificial Sequence: Synthetic
      HDM03T peptide

<400> SEQUENCE: 90

Leu Ala Glu Gln Glu Leu Val Asp Ser Ala Ser Gln His Gly
1               5                   10


<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      HDM06A peptide

<400> SEQUENCE: 91

Arg Tyr Val Ala Arg Glu Gln Ser Ser Arg Arg Pro
1               5                   10


<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      HDM06B peptide
<220> FEATURE:
<221> NAME/KEY: MOD_RES
<222> LOCATION: (9)..(9)
<223> OTHER INFORMATION: 5-aminobutyric acid

<400> SEQUENCE: 92

Arg Tyr Val Ala Arg Glu Gln Ser Xaa Arg Arg Pro
1               5                   10


<210> SEQ ID NO 93
<211> LENGTH: 13
<212> TYPE: PRT
<213> ORGANISM: Dermatophagoides pteronyssinus

<400> SEQUENCE: 93

Pro Asn Val Asn Lys Ile Arg Glu Ala Leu Ala Gln Thr
1               5                   10


<210> SEQ ID NO 94
<211> LENGTH: 14
<212> TYPE: PRT
<213> ORGANISM: Dermatophagoides pteronyssinus

<400> SEQUENCE: 94

Arg Glu Ala Leu Ala Gln Thr His Ser Ala Ile Ala Val Ile
1               5                   10


<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      HDM19A peptide

<400> SEQUENCE: 95

Asp Gln Val Asp Val Lys Asp Ser Ala Asn His Glu Ile Lys Lys
1               5                   10                  15


<210> SEQ ID NO 96
```

<211> LENGTH: 15
<212> TYPE: PRT
<213> ORGANISM: Artificial Sequence
<220> FEATURE:
<223> OTHER INFORMATION: Description of Artificial Sequence: Synthetic HDM19B peptide
<220> FEATURE:
<221> NAME/KEY: MOD_RES
<222> LOCATION: (8)..(8)
<223> OTHER INFORMATION: 5-aminobutyric acid

<400> SEQUENCE: 96

Asp Gln Val Asp Val Lys Asp Xaa Ala Asn His Glu Ile Lys Lys
1 5 10 15

<210> SEQ ID NO 97
<211> LENGTH: 12
<212> TYPE: PRT
<213> ORGANISM: Dermatophagoides pteronyssinus

<400> SEQUENCE: 97

Ile Ile His Arg Gly Lys Pro Phe Gln Leu Glu Ala
1 5 10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic HDM20B peptide

<400> SEQUENCE: 98

Ser Ile Ile His Arg Gly Lys Pro Phe Gln Leu Glu Ala
1 5 10

<210> SEQ ID NO 99
<211> LENGTH: 15
<212> TYPE: PRT
<213> ORGANISM: Dermatophagoides pteronyssinus

<400> SEQUENCE: 99

Lys Pro Phe Gln Leu Glu Ala Val Phe Glu Ala Asn Gln Asn Thr
1 5 10 15

<210> SEQ ID NO 100
<211> LENGTH: 16
<212> TYPE: PRT
<213> ORGANISM: Dermatophagoides pteronyssinus

<400> SEQUENCE: 100

Lys Pro Phe Gln Leu Glu Ala Val Phe Glu Ala Asn Gln Asn Thr Lys
1 5 10 15

<210> SEQ ID NO 101
<211> LENGTH: 17
<212> TYPE: PRT
<213> ORGANISM: Dermatophagoides pteronyssinus

<400> SEQUENCE: 101

Arg Gly Lys Pro Phe Gln Leu Glu Ala Val Phe Glu Ala Asn Gln Asn
1 5 10 15

Thr

<210> SEQ ID NO 102
<211> LENGTH: 14

<212> TYPE: PRT
<213> ORGANISM: Dermatophagoides pteronyssinus

<400> SEQUENCE: 102

Glu Ala Val Phe Glu Ala Asn Gln Asn Thr Lys Thr Ala Lys
1 5 10

<210> SEQ ID NO 103
<211> LENGTH: 13
<212> TYPE: PRT
<213> ORGANISM: Dermatophagoides pteronyssinus

<400> SEQUENCE: 103

Gly Leu Glu Val Asp Val Pro Gly Ile Asp Pro Asn Ala
1 5 10

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
HDM23C peptide

<400> SEQUENCE: 104

Gly Leu Glu Val Asp Val Pro Gly Ile Asp Pro Asn Ala Ser His
1 5 10 15

<210> SEQ ID NO 105
<211> LENGTH: 14
<212> TYPE: PRT
<213> ORGANISM: Artificial Sequence
<220> FEATURE:
<223> OTHER INFORMATION: Description of Artificial Sequence: Synthetic
HDM26B peptide

<400> SEQUENCE: 105

Gly Val Leu Ala Ser Ala Ile Ala Thr His Ala Lys Ile Arg
1 5 10

<210> SEQ ID NO 106
<211> LENGTH: 14
<212> TYPE: PRT
<213> ORGANISM: Artificial Sequence
<220> FEATURE:
<223> OTHER INFORMATION: Description of Artificial Sequence: Synthetic
HDM26C peptide
<220> FEATURE:
<221> NAME/KEY: MOD_RES
<222> LOCATION: (5)..(5)
<223> OTHER INFORMATION: 5-aminobutyric acid

<400> SEQUENCE: 106

Gly Val Leu Ala Xaa Ala Ile Ala Thr His Ala Lys Ile Arg
1 5 10

<210> SEQ ID NO 107
<211> LENGTH: 13
<212> TYPE: PRT
<213> ORGANISM: Dermatophagoides pteronyssinus

<400> SEQUENCE: 107

Asp Lys Phe Glu Arg His Ile Gly Ile Ile Asp Leu Lys
1 5 10

<210> SEQ ID NO 108
<211> LENGTH: 13

<212> TYPE: PRT
<213> ORGANISM: Dermatophagoides pteronyssinus

<400> SEQUENCE: 108

Ile Asp Leu Lys Gly Glu Leu Asp Met Arg Asn Ile Gln
1 5 10

<210> SEQ ID NO 109
<211> LENGTH: 13
<212> TYPE: PRT
<213> ORGANISM: Dermatophagoides pteronyssinus

<400> SEQUENCE: 109

Leu Asp Met Arg Asn Ile Gln Val Arg Gly Leu Lys Gln
1 5 10

<210> SEQ ID NO 110
<211> LENGTH: 15
<212> TYPE: PRT
<213> ORGANISM: Dermatophagoides pteronyssinus

<400> SEQUENCE: 110

Arg Asn Ile Gln Val Arg Gly Leu Lys Gln Met Lys Arg Val Gly
1 5 10 15

<210> SEQ ID NO 111
<211> LENGTH: 14
<212> TYPE: PRT
<213> ORGANISM: Dermatophagoides pteronyssinus

<400> SEQUENCE: 111

Arg Gly Leu Lys Gln Met Lys Arg Val Gly Asp Ala Asn Val
1 5 10

<210> SEQ ID NO 112
<211> LENGTH: 15
<212> TYPE: PRT
<213> ORGANISM: Dermatophagoides pteronyssinus

<400> SEQUENCE: 112

His Asp Asp Val Val Ser Met Glu Tyr Asp Leu Ala Tyr Lys Leu
1 5 10 15

<210> SEQ ID NO 113
<211> LENGTH: 19
<212> TYPE: PRT
<213> ORGANISM: Dermatophagoides pteronyssinus

<400> SEQUENCE: 113

His Asp Asp Val Val Ser Met Glu Tyr Asp Leu Ala Tyr Lys Leu Gly
1 5 10 15

Asp Leu His

<210> SEQ ID NO 114
<211> LENGTH: 15
<212> TYPE: PRT
<213> ORGANISM: Dermatophagoides pteronyssinus

<400> SEQUENCE: 114

Val Ser Met Glu Tyr Asp Leu Ala Tyr Lys Leu Gly Asp Leu His
1 5 10 15

<210> SEQ ID NO 115
<211> LENGTH: 14

<212> TYPE: PRT
<213> ORGANISM: Dermatophagoides pteronyssinus

<400> SEQUENCE: 115

Val Ser Met Glu Tyr Asp Leu Ala Tyr Lys Leu Gly Asp Leu
1 5 10

<210> SEQ ID NO 116
<211> LENGTH: 14
<212> TYPE: PRT
<213> ORGANISM: Dermatophagoides pteronyssinus

<400> SEQUENCE: 116

Thr Ala Ile Phe Gln Asp Thr Val Arg Ala Glu Met Thr Lys
1 5 10

<210> SEQ ID NO 117
<211> LENGTH: 18
<212> TYPE: PRT
<213> ORGANISM: Dermatophagoides pteronyssinus

<400> SEQUENCE: 117

Thr Ala Ile Phe Gln Asp Thr Val Arg Ala Glu Met Thr Lys Val Leu
1 5 10 15

Ala Pro

<210> SEQ ID NO 118
<211> LENGTH: 13
<212> TYPE: PRT
<213> ORGANISM: Dermatophagoides pteronyssinus

<400> SEQUENCE: 118

Asp Thr Val Arg Ala Glu Met Thr Lys Val Leu Ala Pro
1 5 10

<210> SEQ ID NO 119
<211> LENGTH: 13
<212> TYPE: PRT
<213> ORGANISM: Dermatophagoides pteronyssinus

<400> SEQUENCE: 119

Val Asp Phe Lys Gly Glu Leu Ala Met Arg Asn Ile Glu
1 5 10

<210> SEQ ID NO 120
<211> LENGTH: 15
<212> TYPE: PRT
<213> ORGANISM: Dermatophagoides pteronyssinus

<400> SEQUENCE: 120

Val Asp Phe Lys Gly Glu Leu Ala Met Arg Asn Ile Glu Ala Arg
1 5 10 15

<210> SEQ ID NO 121
<211> LENGTH: 17
<212> TYPE: PRT
<213> ORGANISM: Dermatophagoides pteronyssinus

<400> SEQUENCE: 121

Arg Phe Gly Ile Ser Asn Tyr Cys Gln Ile Tyr Pro Pro Asn Val Asn
1 5 10 15

Lys

<210> SEQ ID NO 122
<211> LENGTH: 17
<212> TYPE: PRT
<213> ORGANISM: Artificial Sequence
<220> FEATURE:
<223> OTHER INFORMATION: Description of Artificial Sequence: Synthetic
HDM100A peptide

<400> SEQUENCE: 122

Arg Phe Gly Ile Ser Asn Tyr Ser Gln Ile Tyr Pro Pro Asn Val Asn
1 5 10 15

Lys

<210> SEQ ID NO 123
<211> LENGTH: 17
<212> TYPE: PRT
<213> ORGANISM: Artificial Sequence
<220> FEATURE:
<223> OTHER INFORMATION: Description of Artificial Sequence: Synthetic
HDM100B peptide
<220> FEATURE:
<221> NAME/KEY: MOD_RES
<222> LOCATION: (8)..(8)
<223> OTHER INFORMATION: 5-aminobutyric acid

<400> SEQUENCE: 123

Arg Phe Gly Ile Ser Asn Tyr Xaa Gln Ile Tyr Pro Pro Asn Val Asn
1 5 10 15

Lys

<210> SEQ ID NO 124
<211> LENGTH: 16
<212> TYPE: PRT
<213> ORGANISM: Dermatophagoides pteronyssinus

<400> SEQUENCE: 124

Asn Tyr Cys Gln Ile Tyr Pro Pro Asn Val Asn Lys Ile Arg Glu Ala
1 5 10 15

<210> SEQ ID NO 125
<211> LENGTH: 16
<212> TYPE: PRT
<213> ORGANISM: Artificial Sequence
<220> FEATURE:
<223> OTHER INFORMATION: Description of Artificial Sequence: Synthetic
HDM101A peptide

<400> SEQUENCE: 125

Asn Tyr Ser Gln Ile Tyr Pro Pro Asn Val Asn Lys Ile Arg Glu Ala
1 5 10 15

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
HDM101B peptide
<220> FEATURE:
<221> NAME/KEY: MOD_RES
<222> LOCATION: (3)..(3)
<223> OTHER INFORMATION: 5-aminobutyric acid

<400> SEQUENCE: 126

Asn Tyr Xaa Gln Ile Tyr Pro Pro Asn Val Asn Lys Ile Arg Glu Ala
1 5 10 15

<210> SEQ ID NO 127
<211> LENGTH: 13
<212> TYPE: PRT
<213> ORGANISM: Dermatophagoides pteronyssinus

<400> SEQUENCE: 127

Asn Ala Gln Arg Phe Gly Ile Ser Asn Tyr Cys Gln Ile
1               5                   10

<210> SEQ ID NO 128
<211> LENGTH: 13
<212> TYPE: PRT
<213> ORGANISM: Artificial Sequence
<220> FEATURE:
<223> OTHER INFORMATION: Description of Artificial Sequence: Synthetic
      HDM102A peptide

<400> SEQUENCE: 128

Asn Ala Gln Arg Phe Gly Ile Ser Asn Tyr Ser Gln Ile
1               5                   10

<210> SEQ ID NO 129
<211> LENGTH: 13
<212> TYPE: PRT
<213> ORGANISM: Artificial Sequence
<220> FEATURE:
<223> OTHER INFORMATION: Description of Artificial Sequence: Synthetic
      HDM102B peptide
<220> FEATURE:
<221> NAME/KEY: MOD_RES
<222> LOCATION: (11)..(11)
<223> OTHER INFORMATION: 5-aminobutyric acid

<400> SEQUENCE: 129

Asn Ala Gln Arg Phe Gly Ile Ser Asn Tyr Xaa Gln Ile
1               5                   10

<210> SEQ ID NO 130
<211> LENGTH: 18
<212> TYPE: PRT
<213> ORGANISM: Dermatophagoides pteronyssinus

<400> SEQUENCE: 130

Lys Gly Gln Gln Tyr Asp Ile Lys Tyr Thr Trp Asn Val Pro Lys Ile
1               5                   10                  15

Ala Pro

<210> SEQ ID NO 131
<211> LENGTH: 13
<212> TYPE: PRT
<213> ORGANISM: Dermatophagoides pteronyssinus

<400> SEQUENCE: 131

Trp Asn Val Pro Lys Ile Ala Pro Lys Ser Glu Asn Val
1               5                   10

<210> SEQ ID NO 132
<211> LENGTH: 13
<212> TYPE: PRT
<213> ORGANISM: Dermatophagoides pteronyssinus

<400> SEQUENCE: 132

Glu Ser Val Lys Tyr Val Gln Ser Asn Gly Gly Ala Ile
1               5                   10

<210> SEQ ID NO 133

<211> LENGTH: 11
<212> TYPE: PRT
<213> ORGANISM: Dermatophagoides pteronyssinus

<400> SEQUENCE: 133

Phe Lys Asn Arg Phe Leu Met Ser Ala Glu Ala
1 5 10

<210> SEQ ID NO 134
<211> LENGTH: 10
<212> TYPE: PRT
<213> ORGANISM: Dermatophagoides pteronyssinus

<400> SEQUENCE: 134

Phe Lys Asn Arg Phe Leu Met Ser Ala Glu
1 5 10

<210> SEQ ID NO 135
<211> LENGTH: 11
<212> TYPE: PRT
<213> ORGANISM: Dermatophagoides pteronyssinus

<400> SEQUENCE: 135

Glu Phe Lys Asn Arg Phe Leu Met Ser Ala Glu
1 5 10

<210> SEQ ID NO 136
<211> LENGTH: 19
<212> TYPE: PRT
<213> ORGANISM: Dermatophagoides pteronyssinus

<400> SEQUENCE: 136

Asp Leu Arg Gln Met Arg Thr Val Thr Pro Ile Arg Met Gln Gly Gly
1 5 10 15

Cys Gly Ser

<210> SEQ ID NO 137
<211> LENGTH: 19
<212> TYPE: PRT
<213> ORGANISM: Artificial Sequence
<220> FEATURE:
<223> OTHER INFORMATION: Description of Artificial Sequence: Synthetic
HDM203B peptide

<400> SEQUENCE: 137

Asp Leu Arg Gln Met Arg Thr Val Thr Pro Ile Arg Met Gln Gly Gly
1 5 10 15

Ser Gly Ser

<210> SEQ ID NO 138
<211> LENGTH: 14
<212> TYPE: PRT
<213> ORGANISM: Dermatophagoides pteronyssinus

<400> SEQUENCE: 138

Ser Ala Tyr Leu Ala Tyr Arg Asn Gln Ser Leu Asp Leu Ala
1 5 10

<210> SEQ ID NO 139
<211> LENGTH: 11
<212> TYPE: PRT
<213> ORGANISM: Dermatophagoides pteronyssinus

<400> SEQUENCE: 139

Ser Tyr Tyr Arg Tyr Val Ala Arg Glu Gln Ser
1 5 10

<210> SEQ ID NO 140
<211> LENGTH: 18
<212> TYPE: PRT
<213> ORGANISM: Dermatophagoides pteronyssinus

<400> SEQUENCE: 140

Asp Asn Gly Tyr Gly Tyr Phe Ala Ala Asn Ile Asp Leu Met Met Ile
1 5 10 15

Glu Glu

<210> SEQ ID NO 141
<211> LENGTH: 14
<212> TYPE: PRT
<213> ORGANISM: Dermatophagoides pteronyssinus

<400> SEQUENCE: 141

Asn Gly Tyr Gly Tyr Phe Ala Ala Asn Ile Asp Leu Met Met
1 5 10

<210> SEQ ID NO 142
<211> LENGTH: 18
<212> TYPE: PRT
<213> ORGANISM: Dermatophagoides pteronyssinus

<400> SEQUENCE: 142

Asp Met Arg Asn Ile Gln Val Arg Gly Leu Lys Gln Met Lys Arg Val
1 5 10 15

Gly Asp

<210> SEQ ID NO 143
<211> LENGTH: 12
<212> TYPE: PRT
<213> ORGANISM: Ambrosia artemisiifolia

<400> SEQUENCE: 143

Gly Met Ile Lys Ser Asn Asp Gly Pro Pro Ile Leu
1 5 10

<210> SEQ ID NO 144
<211> LENGTH: 12
<212> TYPE: PRT
<213> ORGANISM: Ambrosia artemisiifolia

<400> SEQUENCE: 144

Gly Ser Ser Gln Ile Trp Ile Asp His Cys Ser Leu
1 5 10

<210> SEQ ID NO 145
<211> LENGTH: 12
<212> TYPE: PRT
<213> ORGANISM: Ambrosia artemisiifolia

<400> SEQUENCE: 145

Gln Ile Trp Ile Asp His Cys Ser Leu Ser Lys Ser
1 5 10

<210> SEQ ID NO 146
<211> LENGTH: 12
<212> TYPE: PRT
<213> ORGANISM: Ambrosia artemisiifolia

<400> SEQUENCE: 146

Asp Lys Asp Leu Leu Glu Asn Gly Ala Ile Phe Val
1 5 10

<210> SEQ ID NO 147
<211> LENGTH: 12
<212> TYPE: PRT
<213> ORGANISM: Ambrosia artemisiifolia

<400> SEQUENCE: 147

Leu Leu Glu Asn Gly Ala Ile Phe Val Thr Ser Gly
1 5 10

<210> SEQ ID NO 148
<211> LENGTH: 12
<212> TYPE: PRT
<213> ORGANISM: Ambrosia artemisiifolia

<400> SEQUENCE: 148

Asn Gly Ala Ile Phe Val Thr Ser Gly Ser Asp Pro
1 5 10

<210> SEQ ID NO 149
<211> LENGTH: 12
<212> TYPE: PRT
<213> ORGANISM: Ambrosia artemisiifolia

<400> SEQUENCE: 149

Ile Phe Val Thr Ser Gly Ser Asp Pro Val Leu Thr
1 5 10

<210> SEQ ID NO 150
<211> LENGTH: 12
<212> TYPE: PRT
<213> ORGANISM: Ambrosia artemisiifolia

<400> SEQUENCE: 150

Thr Ser Gly Ser Asp Pro Val Leu Thr Pro Val Gln
1 5 10

<210> SEQ ID NO 151
<211> LENGTH: 12
<212> TYPE: PRT
<213> ORGANISM: Ambrosia artemisiifolia

<400> SEQUENCE: 151

Pro Val Gln Ser Ala Gly Met Ile Pro Ala Glu Pro
1 5 10

<210> SEQ ID NO 152
<211> LENGTH: 12
<212> TYPE: PRT
<213> ORGANISM: Ambrosia artemisiifolia

<400> SEQUENCE: 152

Ser Ala Gly Met Ile Pro Ala Glu Pro Gly Glu Ala
1 5 10

<210> SEQ ID NO 153
<211> LENGTH: 12
<212> TYPE: PRT
<213> ORGANISM: Ambrosia artemisiifolia

<400> SEQUENCE: 153

Glu Gly Thr Leu Arg Phe Ala Ala Ala Gln Asn Arg
1 5 10

<210> SEQ ID NO 154
<211> LENGTH: 12
<212> TYPE: PRT
<213> ORGANISM: Ambrosia artemisiifolia

<400> SEQUENCE: 154

Leu Arg Phe Ala Ala Ala Gln Asn Arg Pro Leu Trp
1 5 10

<210> SEQ ID NO 155
<211> LENGTH: 12
<212> TYPE: PRT
<213> ORGANISM: Ambrosia artemisiifolia

<400> SEQUENCE: 155

Gln Glu Leu Val Val Asn Ser Asp Lys Thr Ile Asp
1 5 10

<210> SEQ ID NO 156
<211> LENGTH: 12
<212> TYPE: PRT
<213> ORGANISM: Ambrosia artemisiifolia

<400> SEQUENCE: 156

Val Val Asn Ser Asp Lys Thr Ile Asp Gly Arg Gly
1 5 10

<210> SEQ ID NO 157
<211> LENGTH: 12
<212> TYPE: PRT
<213> ORGANISM: Ambrosia artemisiifolia

<400> SEQUENCE: 157

Ser Asp Lys Thr Ile Asp Gly Arg Gly Val Lys Val
1 5 10

<210> SEQ ID NO 158
<211> LENGTH: 12
<212> TYPE: PRT
<213> ORGANISM: Ambrosia artemisiifolia

<400> SEQUENCE: 158

Thr Ile Asp Gly Arg Gly Val Lys Val Glu Ile Ile
1 5 10

<210> SEQ ID NO 159
<211> LENGTH: 12
<212> TYPE: PRT
<213> ORGANISM: Ambrosia artemisiifolia

<400> SEQUENCE: 159

Gly Glu Ala Ala Ile Lys Leu Thr Ser Ser Ala Gly
1 5 10

<210> SEQ ID NO 160
<211> LENGTH: 12
<212> TYPE: PRT
<213> ORGANISM: Ambrosia artemisiifolia

<400> SEQUENCE: 160

Ala Ile Lys Leu Thr Ser Ser Ala Gly Val Leu Ser
1 5 10

<210> SEQ ID NO 161
<211> LENGTH: 12
<212> TYPE: PRT
<213> ORGANISM: Ambrosia artemisiifolia

<400> SEQUENCE: 161

```
Leu Thr Ser Ser Ala Gly Val Leu Ser Cys Arg Pro
1               5                   10
```

<210> SEQ ID NO 162
<211> LENGTH: 12
<212> TYPE: PRT
<213> ORGANISM: Ambrosia artemisiifolia

<400> SEQUENCE: 162

```
Gly Ser Thr His Val Thr Ile Ser Asn Cys Lys Phe
1               5                   10
```

<210> SEQ ID NO 163
<211> LENGTH: 17
<212> TYPE: PRT
<213> ORGANISM: Ambrosia artemisiifolia

<400> SEQUENCE: 163

```
His Gly Phe Phe Gln Val Val Asn Asn Asn Tyr Asp Arg Gly Thr Tyr
1               5                   10                  15

Ala
```

<210> SEQ ID NO 164
<211> LENGTH: 12
<212> TYPE: PRT
<213> ORGANISM: Ambrosia artemisiifolia

<400> SEQUENCE: 164

```
Glu Thr Arg Arg Leu Thr Thr Ser Gly Ala Tyr Asn
1               5                   10
```

<210> SEQ ID NO 165
<211> LENGTH: 396
<212> TYPE: PRT
<213> ORGANISM: Ambrosia artemisiifolia

<400> SEQUENCE: 165

```
Met Gly Ile Lys His Cys Cys Tyr Ile Leu Tyr Phe Thr Leu Ala Leu
1               5                   10                  15

Val Thr Leu Leu Gln Pro Val Arg Ser Ala Glu Asp Leu Gln Glu Ile
            20                  25                  30

Leu Pro Val Asn Glu Thr Arg Arg Leu Thr Thr Ser Gly Ala Tyr Asn
        35                  40                  45

Ile Ile Asp Gly Cys Trp Arg Gly Lys Ala Asp Trp Ala Glu Asn Arg
    50                  55                  60

Lys Ala Leu Ala Asp Cys Ala Gln Gly Phe Gly Lys Gly Thr Val Gly
65                  70                  75                  80

Gly Lys Asp Gly Asp Ile Tyr Thr Val Thr Ser Glu Leu Asp Asp Asp
                85                  90                  95

Val Ala Asn Pro Lys Glu Gly Thr Leu Arg Phe Gly Ala Ala Gln Asn
            100                 105                 110

Arg Pro Leu Trp Ile Ile Phe Glu Arg Asp Met Val Ile Arg Leu Asp
        115                 120                 125
```

Lys Glu Met Val Val Asn Ser Asp Lys Thr Ile Asp Gly Arg Gly Ala
130 135 140

Lys Val Glu Ile Ile Asn Ala Gly Phe Thr Leu Asn Gly Val Lys Asn
145 150 155 160

Val Ile Ile His Asn Ile Asn Met His Asp Val Lys Val Asn Pro Gly
165 170 175

Gly Leu Ile Lys Ser Asn Asp Gly Pro Ala Ala Pro Arg Ala Gly Ser
180 185 190

Asp Gly Asp Ala Ile Ser Ile Ser Gly Ser Ser Gln Ile Trp Ile Asp
195 200 205

His Cys Ser Leu Ser Lys Ser Val Asp Gly Leu Val Asp Ala Lys Leu
210 215 220

Gly Thr Thr Arg Leu Thr Val Ser Asn Ser Leu Phe Thr Gln His Gln
225 230 235 240

Phe Val Leu Leu Phe Gly Ala Gly Asp Glu Asn Ile Glu Asp Arg Gly
245 250 255

Met Leu Ala Thr Val Ala Phe Asn Thr Phe Thr Asp Asn Val Asp Gln
260 265 270

Arg Met Pro Arg Cys Arg His Gly Phe Phe Gln Val Val Asn Asn Asn
275 280 285

Tyr Asp Lys Trp Gly Ser Tyr Ala Ile Gly Gly Ser Ala Ser Pro Thr
290 295 300

Ile Leu Ser Gln Gly Asn Arg Phe Cys Ala Pro Asp Glu Arg Ser Lys
305 310 315 320

Lys Asn Val Leu Gly Arg His Gly Glu Ala Ala Ala Glu Ser Met Lys
325 330 335

Trp Asn Trp Arg Thr Asn Lys Asp Val Leu Glu Asn Gly Ala Ile Phe
340 345 350

Val Ala Ser Gly Val Asp Pro Val Leu Thr Pro Glu Gln Ser Ala Gly
355 360 365

Met Ile Pro Ala Glu Pro Gly Glu Ser Ala Leu Ser Leu Thr Ser Ser
370 375 380

Ala Gly Val Leu Ser Cys Gln Pro Gly Ala Pro Cys
385 390 395

<210> SEQ ID NO 166
<211> LENGTH: 398
<212> TYPE: PRT
<213> ORGANISM: Ambrosia artemisiifolia

<400> SEQUENCE: 166

Met Gly Ile Lys His Cys Cys Tyr Ile Leu Tyr Phe Thr Leu Ala Leu
1 5 10 15

Val Thr Leu Leu Gln Pro Val Arg Ser Ala Glu Asp Val Glu Glu Phe
20 25 30

Leu Pro Ser Ala Asn Glu Thr Arg Arg Ser Leu Lys Ala Cys Glu Ala
35 40 45

His Asn Ile Ile Asp Lys Cys Trp Arg Cys Lys Ala Asp Trp Ala Asn
50 55 60

Asn Arg Gln Ala Leu Ala Asp Cys Ala Gln Gly Phe Ala Lys Gly Thr
65 70 75 80

Tyr Gly Gly Lys His Gly Asp Val Tyr Thr Val Thr Ser Asp Lys Asp
85 90 95

Asp Asp Val Ala Asn Pro Lys Glu Gly Thr Leu Arg Phe Ala Ala Ala
100 105 110

```
Gln Asn Arg Pro Leu Trp Ile Ile Phe Lys Arg Asn Met Val Ile His
        115                 120                 125

Leu Asn Gln Glu Leu Val Val Asn Ser Asp Lys Thr Ile Asp Gly Arg
    130                 135                 140

Gly Val Lys Val Asn Ile Val Asn Ala Gly Leu Thr Leu Met Asn Val
145                 150                 155                 160

Lys Asn Ile Ile Ile His Asn Ile Asn Ile His Asp Ile Lys Val Cys
                165                 170                 175

Pro Gly Gly Met Ile Lys Ser Asn Asp Gly Pro Pro Ile Leu Arg Gln
            180                 185                 190

Gln Ser Asp Gly Asp Ala Ile Asn Val Ala Gly Ser Ser Gln Ile Trp
        195                 200                 205

Ile Asp His Cys Ser Leu Ser Lys Ala Ser Asp Gly Leu Leu Asp Ile
    210                 215                 220

Thr Leu Gly Ser Ser His Val Thr Val Ser Asn Cys Lys Phe Thr Gln
225                 230                 235                 240

His Gln Phe Val Leu Leu Leu Gly Ala Asp Asp Thr His Tyr Gln Asp
                245                 250                 255

Lys Gly Met Leu Ala Thr Val Ala Phe Asn Met Phe Thr Asp His Val
            260                 265                 270

Asp Gln Arg Met Pro Arg Cys Arg Phe Gly Phe Phe Gln Val Val Asn
        275                 280                 285

Asn Asn Tyr Asp Arg Trp Gly Thr Tyr Ala Ile Gly Gly Ser Ser Ala
    290                 295                 300

Pro Thr Ile Leu Ser Gln Gly Asn Arg Phe Phe Ala Pro Asp Asp Ile
305                 310                 315                 320

Ile Lys Lys Asn Val Leu Ala Arg Thr Gly Thr Gly Asn Ala Glu Ser
                325                 330                 335

Met Ser Trp Asn Trp Arg Thr Asp Arg Asp Leu Leu Glu Asn Gly Ala
            340                 345                 350

Ile Phe Leu Pro Ser Gly Ser Asp Pro Val Leu Thr Pro Glu Gln Lys
        355                 360                 365

Ala Gly Met Ile Pro Ala Glu Pro Gly Glu Ala Val Leu Arg Leu Thr
    370                 375                 380

Ser Ser Ala Gly Val Leu Ser Cys His Gln Gly Ala Pro Cys
385                 390                 395
```

```
<210> SEQ ID NO 167
<211> LENGTH: 397
<212> TYPE: PRT
<213> ORGANISM: Ambrosia artemisiifolia

<400> SEQUENCE: 167

Met Gly Ile Lys Gln Cys Cys Tyr Ile Leu Tyr Phe Thr Leu Ala Leu
1               5                   10                  15

Val Ala Leu Leu Gln Pro Val Arg Ser Ala Glu Gly Val Gly Glu Ile
            20                  25                  30

Leu Pro Ser Val Asn Glu Thr Arg Ser Leu Gln Ala Cys Glu Ala Leu
        35                  40                  45

Asn Ile Ile Asp Lys Cys Trp Arg Gly Lys Ala Asp Trp Glu Asn Asn
    50                  55                  60

Arg Gln Ala Leu Ala Asp Cys Ala Gln Gly Phe Ala Lys Gly Thr Tyr
65                  70                  75                  80

Gly Gly Lys Trp Gly Asp Val Tyr Thr Val Thr Ser Asn Leu Asp Asp
```

85 90 95

Asp Val Ala Asn Pro Lys Glu Gly Thr Leu Arg Phe Ala Ala Ala Gln
100 105 110

Asn Arg Pro Leu Trp Ile Ile Phe Lys Asn Asp Met Val Ile Asn Leu
115 120 125

Asn Gln Glu Leu Val Val Asn Ser Asp Lys Thr Ile Asp Gly Arg Gly
130 135 140

Val Lys Val Glu Ile Ile Asn Gly Gly Leu Thr Leu Met Asn Val Lys
145 150 155 160

Asn Ile Ile Ile His Asn Ile Asn Ile His Asp Val Lys Val Leu Pro
165 170 175

Gly Gly Met Ile Lys Ser Asn Asp Gly Pro Pro Ile Leu Arg Gln Ala
180 185 190

Ser Asp Gly Asp Thr Ile Asn Val Ala Gly Ser Ser Gln Ile Trp Ile
195 200 205

Asp His Cys Ser Leu Ser Lys Ser Phe Asp Gly Leu Val Asp Val Thr
210 215 220

Leu Gly Ser Thr His Val Thr Ile Ser Asn Cys Lys Phe Thr Gln Gln
225 230 235 240

Ser Lys Ala Ile Leu Leu Gly Ala Asp Asp Thr His Val Gln Asp Lys
245 250 255

Gly Met Leu Ala Thr Val Ala Phe Asn Met Phe Thr Asp Asn Val Asp
260 265 270

Gln Arg Met Pro Arg Cys Arg Phe Gly Phe Phe Gln Val Val Asn Asn
275 280 285

Asn Tyr Asp Arg Trp Gly Thr Tyr Ala Ile Gly Gly Ser Ser Ala Pro
290 295 300

Thr Ile Leu Cys Gln Gly Asn Arg Phe Leu Ala Pro Asp Asp Gln Ile
305 310 315 320

Lys Lys Asn Val Leu Ala Arg Thr Gly Thr Gly Ala Ala Glu Ser Met
325 330 335

Ala Trp Asn Trp Arg Ser Asp Lys Asp Leu Leu Glu Asn Gly Ala Ile
340 345 350

Phe Val Thr Ser Gly Ser Asp Pro Val Leu Thr Pro Val Gln Ser Ala
355 360 365

Gly Met Ile Pro Ala Glu Pro Gly Glu Ala Ala Ile Lys Leu Thr Ser
370 375 380

Ser Ala Gly Val Phe Ser Cys His Pro Gly Ala Pro Cys
385 390 395

<210> SEQ ID NO 168
<211> LENGTH: 392
<212> TYPE: PRT
<213> ORGANISM: Ambrosia artemisiifolia

<400> SEQUENCE: 168

Met Gly Ile Lys His Cys Cys Tyr Ile Leu Tyr Phe Thr Leu Ala Leu
1 5 10 15

Val Thr Leu Leu Gln Pro Val Arg Ser Ala Glu Asp Leu Gln Gln Ile
20 25 30

Leu Pro Ser Ala Asn Glu Thr Arg Ser Leu Thr Thr Cys Gly Thr Tyr
35 40 45

Asn Ile Ile Asp Gly Cys Trp Arg Gly Lys Ala Asp Trp Ala Glu Asn
50 55 60

```
Arg Lys Ala Leu Ala Asp Cys Ala Gln Gly Phe Ala Lys Gly Thr Ile
65                  70                  75                  80

Gly Gly Lys Asp Gly Asp Ile Tyr Thr Val Thr Ser Glu Leu Asp Asp
                85                  90                  95

Asp Val Ala Asn Pro Lys Glu Gly Thr Leu Arg Phe Gly Ala Ala Gln
            100                 105                 110

Asn Arg Pro Leu Trp Ile Ile Phe Ala Arg Asp Met Val Ile Arg Leu
        115                 120                 125

Asp Arg Glu Leu Ala Ile Asn Asn Asp Lys Thr Ile Asp Gly Arg Gly
    130                 135                 140

Ala Lys Val Glu Ile Ile Asn Ala Gly Phe Ala Ile Tyr Asn Val Lys
145                 150                 155                 160

Asn Ile Ile Ile His Asn Ile Ile Met His Asp Ile Val Val Asn Pro
                165                 170                 175

Gly Gly Leu Ile Lys Ser His Asp Gly Pro Pro Val Pro Arg Lys Gly
            180                 185                 190

Ser Asp Gly Asp Ala Ile Gly Ile Ser Gly Gly Ser Gln Ile Trp Ile
        195                 200                 205

Asp His Cys Ser Leu Ser Lys Ala Val Asp Gly Leu Ile Asp Ala Lys
    210                 215                 220

His Gly Ser Thr His Phe Thr Val Ser Asn Cys Leu Phe Thr Gln His
225                 230                 235                 240

Gln Tyr Leu Leu Leu Phe Trp Asp Phe Asp Glu Arg Gly Met Leu Cys
                245                 250                 255

Thr Val Ala Phe Asn Lys Phe Thr Asp Asn Val Asp Gln Arg Met Pro
            260                 265                 270

Asn Leu Arg His Gly Phe Val Gln Val Val Asn Asn Asn Tyr Glu Arg
        275                 280                 285

Trp Gly Ser Tyr Ala Leu Gly Gly Ser Ala Gly Pro Thr Ile Leu Ser
    290                 295                 300

Gln Gly Asn Arg Phe Leu Ala Ser Asp Ile Lys Lys Glu Val Val Gly
305                 310                 315                 320

Arg Tyr Gly Glu Ser Ala Met Ser Glu Ser Ile Asn Trp Asn Trp Arg
                325                 330                 335

Ser Tyr Met Asp Val Phe Glu Asn Gly Ala Ile Phe Val Pro Ser Gly
            340                 345                 350

Val Asp Pro Val Leu Thr Pro Glu Gln Asn Ala Gly Met Ile Pro Ala
        355                 360                 365

Glu Pro Gly Glu Ala Val Leu Arg Leu Thr Ser Ser Ala Gly Val Leu
    370                 375                 380

Ser Cys Gln Pro Gly Ala Pro Cys
385                 390


<210> SEQ ID NO 169
<211> LENGTH: 11
<212> TYPE: PRT
<213> ORGANISM: Ambrosia artemisiifolia

<400> SEQUENCE: 169

Gly Met Ile Lys Ser Asn Asp Gly Pro Pro Ile
1               5                   10


<210> SEQ ID NO 170
<211> LENGTH: 11
<212> TYPE: PRT
<213> ORGANISM: Ambrosia artemisiifolia
```

<400> SEQUENCE: 170

Gly Leu Ile Lys Ser His Asp Gly Pro Pro Val
1 5 10

<210> SEQ ID NO 171
<211> LENGTH: 11
<212> TYPE: PRT
<213> ORGANISM: Ambrosia artemisiifolia

<400> SEQUENCE: 171

Gly Leu Ile Lys Ser Asn Asp Gly Pro Ala Ala
1 5 10

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
RGW02 peptide

<400> SEQUENCE: 172

Gly Ser Ser Gln Ile Trp Ile Asp His Ser Ser Leu Ser Lys Ser
1 5 10 15

<210> SEQ ID NO 173
<211> LENGTH: 15
<212> TYPE: PRT
<213> ORGANISM: Ambrosia artemisiifolia

<400> SEQUENCE: 173

Gly Ser Ser Gln Ile Trp Ile Asp His Cys Ser Leu Ser Lys Ser
1 5 10 15

<210> SEQ ID NO 174
<211> LENGTH: 15
<212> TYPE: PRT
<213> ORGANISM: Ambrosia artemisiifolia

<400> SEQUENCE: 174

Gly Gly Ser Gln Ile Trp Ile Asp His Cys Ser Leu Ser Lys Ala
1 5 10 15

<210> SEQ ID NO 175
<211> LENGTH: 14
<212> TYPE: PRT
<213> ORGANISM: Ambrosia artemisiifolia

<400> SEQUENCE: 175

Lys Asp Leu Leu Glu Asn Gly Ala Ile Phe Val Thr Ser Gly
1 5 10

<210> SEQ ID NO 176
<211> LENGTH: 13
<212> TYPE: PRT
<213> ORGANISM: Ambrosia artemisiifolia

<400> SEQUENCE: 176

Asp Val Phe Glu Asn Gly Ala Ile Phe Val Pro Ser Gly
1 5 10

<210> SEQ ID NO 177
<211> LENGTH: 14
<212> TYPE: PRT

<213> ORGANISM: Ambrosia artemisiifolia

<400> SEQUENCE: 177

Arg Asp Leu Leu Glu Asn Gly Ala Ile Phe Leu Pro Ser Gly
1 5 10

<210> SEQ ID NO 178
<211> LENGTH: 12
<212> TYPE: PRT
<213> ORGANISM: Ambrosia artemisiifolia

<400> SEQUENCE: 178

Lys Ala Gly Met Ile Pro Ala Glu Pro Gly Glu Ala
1 5 10

<210> SEQ ID NO 179
<211> LENGTH: 12
<212> TYPE: PRT
<213> ORGANISM: Ambrosia artemisiifolia

<400> SEQUENCE: 179

Ser Ala Gly Met Ile Pro Ala Glu Pro Gly Glu Ala
1 5 10

<210> SEQ ID NO 180
<211> LENGTH: 14
<212> TYPE: PRT
<213> ORGANISM: Ambrosia artemisiifolia

<400> SEQUENCE: 180

Lys Glu Gly Thr Leu Arg Phe Ala Ala Ala Gln Asn Arg Pro
1 5 10

<210> SEQ ID NO 181
<211> LENGTH: 14
<212> TYPE: PRT
<213> ORGANISM: Ambrosia artemisiifolia

<400> SEQUENCE: 181

Lys Glu Gly Thr Leu Arg Phe Gly Ala Ala Gln Asn Arg Pro
1 5 10

<210> SEQ ID NO 182
<211> LENGTH: 16
<212> TYPE: PRT
<213> ORGANISM: Ambrosia artemisiifolia

<400> SEQUENCE: 182

Val Val Asn Ser Asp Lys Thr Ile Asp Gly Arg Gly Val Lys Val Glu
1 5 10 15

<210> SEQ ID NO 183
<211> LENGTH: 16
<212> TYPE: PRT
<213> ORGANISM: Ambrosia artemisiifolia

<400> SEQUENCE: 183

Ala Ile Asn Asn Asp Lys Thr Ile Asp Gly Arg Gly Ala Lys Val Glu
1 5 10 15

<210> SEQ ID NO 184
<211> LENGTH: 12
<212> TYPE: PRT
<213> ORGANISM: Ambrosia artemisiifolia

<400> SEQUENCE: 184

Gly Ser Thr His Val Thr Ile Ser Asn Ser Lys Phe
1 5 10

<210> SEQ ID NO 185
<211> LENGTH: 12
<212> TYPE: PRT
<213> ORGANISM: Ambrosia artemisiifolia

<400> SEQUENCE: 185

Gly Ser Thr His Val Thr Ile Ser Asn Cys Lys Phe
1 5 10

<210> SEQ ID NO 186
<211> LENGTH: 12
<212> TYPE: PRT
<213> ORGANISM: Ambrosia artemisiifolia

<400> SEQUENCE: 186

Gly Ser Thr His Phe Thr Val Ser Asn Cys Leu Phe
1 5 10

<210> SEQ ID NO 187
<211> LENGTH: 12
<212> TYPE: PRT
<213> ORGANISM: Ambrosia artemisiifolia

<400> SEQUENCE: 187

Gly Ser Thr His Phe Thr Val Ser Asn Ser Leu Phe
1 5 10

<210> SEQ ID NO 188
<211> LENGTH: 12
<212> TYPE: PRT
<213> ORGANISM: Ambrosia artemisiifolia

<400> SEQUENCE: 188

Gly Thr Thr Arg Leu Thr Val Ser Asn Ser Leu Phe
1 5 10

<210> SEQ ID NO 189
<211> LENGTH: 13
<212> TYPE: PRT
<213> ORGANISM: Ambrosia artemisiifolia

<400> SEQUENCE: 189

Glu Thr Arg Arg Ser Leu Lys Thr Ser Gly Ala Tyr Asn
1 5 10

<210> SEQ ID NO 190
<211> LENGTH: 12
<212> TYPE: PRT
<213> ORGANISM: Ambrosia artemisiifolia

<400> SEQUENCE: 190

Phe Gly Phe Phe Gln Val Val Asn Asn Asn Tyr Asp
1 5 10

<210> SEQ ID NO 191
<211> LENGTH: 12
<212> TYPE: PRT
<213> ORGANISM: Ambrosia artemisiifolia

<400> SEQUENCE: 191

-continued

```
His Gly Phe Phe Gln Val Val Asn Asn Asn Tyr Asp
1               5                   10


<210> SEQ ID NO 192
<211> LENGTH: 12
<212> TYPE: PRT
<213> ORGANISM: Ambrosia artemisiifolia

<400> SEQUENCE: 192

Val Asn Asn Asn Tyr Asp Arg Trp Gly Thr Tyr Ala
1               5                   10


<210> SEQ ID NO 193
<211> LENGTH: 12
<212> TYPE: PRT
<213> ORGANISM: Ambrosia artemisiifolia

<400> SEQUENCE: 193

Val Asn Asn Asn Tyr Asp Lys Trp Gly Ser Tyr Ala
1               5                   10


<210> SEQ ID NO 194
<211> LENGTH: 12
<212> TYPE: PRT
<213> ORGANISM: Ambrosia artemisiifolia

<400> SEQUENCE: 194

Val Asn Asn Asn Tyr Glu Arg Trp Gly Ser Tyr Ala
1               5                   10


<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate

<400> SEQUENCE: 195

Glu Leu Val Asp Ser Ala Ser Gln His Gly
1               5                   10
```